United States Patent
Zhang et al.

(10) Patent No.: US 6,566,358 B2
(45) Date of Patent: May 20, 2003

(54) CYCLOCARBAMATE DERIVATIVES AS PROGESTERONE RECEPTOR MODULATORS

(75) Inventors: Puwen Zhang, Audubon, PA (US); Eugene A. Terefenko, Quakertown, PA (US); Andrew Fensome, Wayne, PA (US); Jay E. Wrobel, Lawrenceville, NJ (US); Horace Fletcher, III, Pottstown, PA (US); Lin Zhi, San Diego, CA (US); Todd K. Jones, Solana Beach, CA (US); James P. Edwards, San Diego, CA (US); Christopher M. Tegley, Thousand Oaks, CA (US)

(73) Assignees: Wyeth, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/948,309

(22) Filed: Sep. 6, 2001

(65) Prior Publication Data

US 2002/0049204 A1 Apr. 25, 2002

Related U.S. Application Data

(62) Division of application No. 09/552,633, filed on Apr. 19, 2000, now abandoned.
(60) Provisional application No. 60/183,012, filed on May 4, 1999, now abandoned.

(51) Int. Cl.$^7$ ............................................. A61K 31/536
(52) U.S. Cl. ............................ 514/230.5; 514/228.2; 514/212.02; 514/212.08
(58) Field of Search .................... 544/92; 514/230.5, 514/228.2, 212.08, 212.02

(56) References Cited

U.S. PATENT DOCUMENTS

| | | | |
|---|---|---|---|
| 3,635,964 A | 1/1972 | Skorcz | 260/247.1 |
| 3,917,592 A | 11/1975 | Kobzina | 260/244 |
| 4,093,730 A | 6/1978 | Butti | |
| 4,440,785 A | 4/1984 | Walsh | 424/317 |
| 4,666,913 A | 5/1987 | Kuhla | 514/259 |
| 4,670,566 A | 6/1987 | Walsh | 548/405 |
| 4,721,721 A | 12/1988 | Kuhla | |
| 4,822,794 A | 4/1989 | Spada | |
| 4,831,027 A | 5/1989 | Narr | 514/212 |
| 4,853,473 A | 8/1989 | Fischer | 549/326 |
| 5,007,952 A | 4/1991 | Kume | 71/73 |
| 5,171,851 A | 12/1992 | Kim | 544/50 |
| 5,414,088 A | 5/1995 | von der Saal | 546/158 |
| 5,453,516 A | 9/1995 | Fischer | 548/543 |
| 5,475,020 A | 12/1995 | Johnson | 514/414 |
| 5,521,166 A | 5/1996 | Grubb | 514/170 |
| 5,681,817 A | 10/1997 | Hodgen | 514/12 |
| 5,688,808 A | 11/1997 | Jones | 514/285 |
| 5,688,810 A | 11/1997 | Jones | 514/311 |
| 5,693,646 A | 12/1997 | Jones | 514/285 |
| 5,693,647 A | 12/1997 | Jones | 514/285 |
| 5,696,127 A | 12/1997 | Jones | 514/285 |
| 5,696,130 A | 12/1997 | Jones | 514/291 |
| 5,696,133 A | 12/1997 | Jones | 514/314 |
| 5,719,136 A | 2/1998 | Chwalisz | 514/170 |
| 5,733,902 A | 3/1998 | Schneider | |
| 5,808,139 A | 9/1998 | Pathirana | |
| 5,874,430 A | 2/1999 | Christ | |
| 6,077,840 A | 6/2000 | Kurihara | |
| 6,306,851 B1 | 10/2001 | Santilli | |

FOREIGN PATENT DOCUMENTS

DE 3633861 4/1988

(List continued on next page.)

OTHER PUBLICATIONS

R. Evans, "The Steroid and Thyroid Hormone Receptor Superfamily", Science, 240:889 (May 13, 1988).

(List continued on next page.)

*Primary Examiner*—John M. Ford
(74) *Attorney, Agent, or Firm*—Howson and Howson

(57) ABSTRACT

This invention provides compounds of Formula (I):

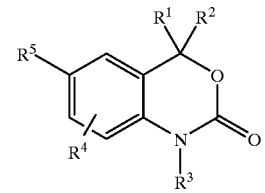

wherein $R^1$ and $R^2$ may be single substituents or fused to form spirocyclic or hetero-spirocyclic rings; $R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, $COR^C$; $R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is H, halogen, CN, $NO_2$, $C_1$ to $C_6$ alkyl, substituted $C_1$ to $C_6$ alkyl, alkynyl, or substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl; and $R^5$ is selected from a trisubstituted benzene ring of a five or six membered ring with 1, 2, or 3 heteroatoms from the group including O, S, SO, $SO_2$ or $NR^6$ and containing one or two independent substituents from the group including H, halogen, CN, $NO_2$, amino, and $C_1$ to $C_3$ alky, $C_1$ to $C_3$ alkoxy, $C_1$ to $C_3$ aminoalkyl, $COR^F$, or $NR^GCOR^F$; or pharmaceutically acceptable salt thereof, as well as pharmaceutical compositions and methods using the compounds as antagonists of the progesterone receptor.

46 Claims, No Drawings

FOREIGN PATENT DOCUMENTS

| | | |
|---|---|---|
| DE | 4330234 | 3/1995 |
| DE | 4344463 | 6/1995 |
| EP | 022317 | 1/1981 |
| EP | 208510 | 1/1987 |
| EP | 311135 | 4/1989 |
| EP | 385850 | 9/1990 |
| EP | 483077 | 9/1991 |
| EP | 454330 | 10/1991 |
| EP | 535529 | 9/1992 |
| EP | 510235 | 10/1992 |
| EP | 947507 | 10/1999 |
| EP | 978279 | 2/2000 |
| JP | 63112584 | 5/1988 |
| WO | WO86/03749 A1 | 7/1986 |
| WO | WO91/06545 A1 | 7/1986 |
| WO | WO91/04974 A1 | 4/1991 |
| WO | WO91/06545 A1 | 5/1991 |
| WO | WO93/12085 A1 | 6/1993 |
| WO | WO94/14434 A1 | 7/1994 |
| WO | WO94/29272 A1 | 12/1994 |
| WO | WO4330234 A1 | 3/1995 |
| WO | WO95/11013 A1 | 4/1995 |
| WO | WO4344463 A1 | 6/1995 |
| WO | WO95/20389 A1 | 8/1995 |
| WO | WO95/20972 A1 | 8/1995 |
| WO | WO95/33746 A1 | 12/1995 |
| WO | WO96/15794 A1 | 5/1996 |
| WO | WO96/19458 A1 | 6/1996 |
| WO | WO96/19997 A1 | 7/1996 |
| WO | WO97/13767 A1 | 4/1997 |
| WO | WO97/49407 A1 | 12/1997 |
| WO | WO98/14436 A1 | 4/1998 |
| WO | WO98/27059 A1 | 6/1998 |
| WO | WO98/55116 A1 | 12/1998 |
| WO | WO99/10325 A1 | 3/1999 |
| WO | WO99/11264 A1 | 3/1999 |
| WO | WO99/15500 A1 | 4/1999 |
| WO | WO99/44608 A1 | 9/1999 |

OTHER PUBLICATIONS

A. Ulmann et al, "Clinical Uses of Mifepristone (MFP)", Ann. N.Y. Acad. Sci., 261:248 (Jun. 12, 1995).

R. Kekkonen et al, "Sequential Regiment of the Antiprogesterone RU486 and Synthetic Progestin for Contraception", Fertility and Sterility, 60(4):610 (Oct., 1993).

K. Horwitz et al, "Progestin, Progesterone Receptors, and Breast Cancer", Horm. Cancer, publisher; Birkhaeuser, Boston, Mass., ed. Vedeckis, pp. 283–306 (1996) (abstract only).

A. Murphy et al, "Regression of Uterine leiomyomata in Response to the Antiprogesterone RU486", J. Clin. Endo. Metab., 76(2):513 (Feb., 1993).

L. Kettel et al, "Endocrine Responses to Long–Term Administration of the Antiprogesterone RU486 in Patients with Pelvic Endometriosis", Fertility and Sterility, 56(3):402 (Sep., 1991).

H. Michna et al, "Differentiation Therapy with Progesterone Antagonists", Ann. N.Y. Acad. Sci., 761:224 (Jun., 1995).

L. Zhi et al, "5–Aryl–1,2–Dihydrochromeno[3,4–f]quinolines: A Novel Class of Nonsteroidal Human Progesterone Receptor Agonists", J. Med. Chem., 41(3):291 (Oct. 22, 1998).

D. Combs et al, "Nonsteroidal Progesterone Receptor Ligands. 2. High–Affinity Ligands with Selectivity for Bone Cell Progesterone Receptors", J. Med. Chem., 38:4880 (Dec. 8, 1995).

K. Perlman et al, "20–Oxopregnacalciferols: Vitamin D Compounds that Bind the Progesterone Receptor", Tet. Letters, 35(15)2295 (1994).

L. Hamann et al, "Synthesis and Biological Activity of Novel Nonsteroidal Progesterone Receptor Antagonists", Ann. N.Y. Acad. Sci., 761:383 (Jun. 12, 1995).

R. Chen et al, "Synthesis and SAR of a Novel Series of Spirobenzothlzaepine Derivatives with Antiprogestin Activity", POI–37, 16$^{th}$ Int. Cong. Het. Chem., Montana (1997).

B. Narr et al, "Preparation, Testing, and Formulation of Imidazobenzoxazinones as Cardiotonics", Chemical Abstracts, 109:22973 (1988).

R. Hartmann et al, "Effects of Brofoxine, A New Anxiolytic on Experimentally Induced Conflict in Rats", Proc. West. Pharmacol. Soc., 21:51–55 (1978).

B. Singh et al, "Novel cAMP PDE III Inhibitor" Imidazo [4,5–b]pyridin–2(3H)–ones and Thiazolo[4,5–b]pyridin–2(3H)–ones and their Analogs, J. Med. Chem., 37:248 (Jan. 21, 1994).

A. Andreani et al, "Potential Antitumor Agents XVII (1). Cytotoxic Agents from Indole Derivatives and their Intermediates", Acta. Pharm. Nord., 2(6):407 (1990).

Sakata et al, "Silver Halide Photographic Materials Useful for Platemaking", Chemical Abstracts, 123:301431 (1993).

P. Pflegel et al, "Polarografie con 7–Chlor–5–phenyl–2–thioxo–1H–2,3–dihydro–1,3,4–benzotriazepinen", Pharmazie, 37(10):714–717 (1982).

E. Barengolts et al, "Progesterone Antagonist RU486 has Bone–Sparing Effects in Ovariectomized Rats", Bone, 17(1):21 (Jul., 1995).

E. Gromachevskaya et al, "Studies of 4H–3, 1–Benzoxazines", Chem. Heterocycl. Cmpds., 33(10):1209–1214 (1997).

D. Chiarino et al, "2,1–Benzisothiazoline 2,2–Dioxide and Derivatives", J. Heterocycl. Chem., 23(6):1645–1649 (Nov.–Dec., 1986).

A. Turck et al, "On the Metabolism of 3–Substituted and 3,6–Disubstituted Pyridazines", Tetrahedron, 49(3):599–606 (1993).

V. Kumar et al, "Synthesis of 7–Azaindole and 7–Azaoxindole Derivatives through a Palladium–Catalyzed Cross–Coupling Reaction", J. Org. Chem., 57(25):6995–6998 (1992).

P. Canonne et al, "Spirocyclization of 1–(o–Aminophenyl)-cycloalkanols and 1–(2'–Amino–3'–pyridinyl)cycloalkanols", J Heterocyclic Chem., 26:113 (Jan.–Feb., 1989).

M–C. Forest et al, "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", J. Med. Chem., 35:163–172 (Jan., 1992).

D. Combs et al, "Heteroatom Analogues of Bemoradan: Chemistry and Cardiotonic Activity of 1,4–Benzothiazinylpyridazinones", J. Med. Chem., 35:172–176 (Jan., 1992).

Kurihari et al., "Synthesis of (±)–PF1092A, B, and C; New Nonsteroidal Progesterone Receptor Ligands", J. Antibiotics, 50(4):360 (Apr., 1997).

A. Kende et al., "Regioselective C–3 Alkylation of Oxindole Dianion", Synth. Commun. 12(1):1 (1982).

T. Tucker et al., "Synthesis of a Series of 4–(Arylethylnyl)–6–Chloro–4–Cyclopropyl–3,4–dihydroquinazolin–2(1H)–ones as Novel Non–Nucleoside HIV–1 Reverse Transcriptase Inhibitors", J. Med. Chem., 37:2347–2444 (Jul. 22, 1994).

J. Edwards et al., "5–Aryl–1,2–Dihydro–5H–Chromeno[3,4–f]Quinolines as Potent, Orally Active, Nonsteroidal Progesterone Receptor Agonists: The Effect of D–Ring Substituents", J. Med. Chem., 41:303–310 (Jan. 29, 1998).

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

V. Mamaev et al., "Synthesis of 4H–Thieno [3,2–B] Pyrrol–5(6H)–One" Bulletin of the Academy of Sciences on the USSR. Division of Chemical Science, US, Consultants Bureau. New York. vol. 9, p. 1549–1553, (1966).

K. Kolasa et al., "Preliminary Pharmacological Studies of the Central Action of Phenyl and Piperidinomethyl Derivatives of 2–Benzoxazolone", Chemical Abstracts, vol. 99, No. 1, Abst. No. 157a (Jul. 4, 1983).

N. Meanwell et al., "Regiospecific Functionalization of 1,3–dihydro–2H–Benzimidazol–2–One and Structurally Related Cyclic Urea Derivatives", J. Organic Chem., 60(6):1565–82 (Mar. 24, 1995).

B. Singh et al., "An Efficient and Novel Synthesis of Fused Thiazol–2(3H)–ones" Heterocycles, 36(1):133–134, p. 136, compounds 16a, 18a (Jan. 1993).

G. Vernin et al., "Etude Dans la Serie des Radicaux heterocycliques. Partie XV. Decomposition aprotique de 1'amino–6–ethyl–2–benzothiazole dans des substrats aromatiques et Heteroaromatiques: preparation des mesityl–6– et furyl–6–ethyl–2–benzothiazoles, des sels quaternaires et des spiropyrannes correspondants", Helvetica Chimica Acta, 62(1/3):21–30 (Jan. 24, 1979).

CYCLOCARBAMATE DERIVATIVES AS PROGESTERONE RECEPTOR MODULATORS

CROSS-REFERENCE TO RELATED APPLICATIONS

This application is a divisional of U.S. patent application Ser. No. 09/552,633, filed Apr. 19, 2000, which claims the benefit of U.S. Patent Application No. 60/183,012, filed May 4, 1999, now abandoned.

FIELD OF THE INVENTION

This invention relates to compounds that antagonists of the progesterone receptor, their preparation and utility.

BACKGROUND OF THE INVENTION

Intracellular receptors (IR) form a class of structurally related gene regulators known as "ligand dependent transcription factors" (R. M. Evans, Science, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR antagonists may be used in contraception. In this context they may be administered alone (Ulmann, et al, Ann. N.Y. Acad. Sci., 261, 248, 1995), in combination with a PR agonist (Kekkonen, et al, Fertility and Sterility, 60, 610, 1993) or in combination with a partial ER antagonist such as tamoxifen (WO 96/19997 A1 Jul. 4, 1996).

PR antagonists may also be useful for the treatment of hormone dependent breast cancers (Horwitz, et al, Horm. Cancer, 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, J. Clin. Endo. Metab., 76, 513, 1993) and endometriosis (Kettel, et al, Fertility and Sterility, 56, 402, 1991).

PR antagonists may also be useful in hormone replacement therapy for post menopausal patients in combination with a partial ER antagonist such as tamoxifen (U.S. Pat. No. 5,719,136).

PR antagonists, such as mifepristone and onapristone, have been shown to be effective in a model of hormone dependent prostate cancer, which may indicate their utility in the treatment of this condition in men (Michna, et al, Ann. N.Y. Acad. Sci., 761, 224, 1995).

The compounds of this invention have been shown to act as competitive inhibitors of progesterone binding to the PR and act as antagonists in functional models, either/or in-vitro and in-vivo. These compounds may be used for contraception, in the treatment of fibroids, endometriosis, breast, uterine, ovarian and prostate cancer, and post menopausal hormone replacement therapy.

Compounds of the prior art are described by Jones, et al, (U.S. Pat. No. 5,688,810) is the PR antagonist dihydroquinoline 1.

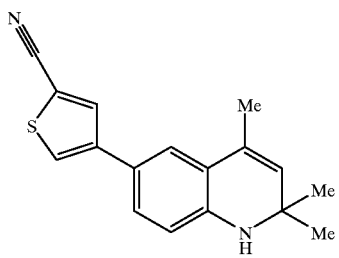

Jones, et al, described the enol ether 2 (U.S. Pat. No. 5,693,646) as a PR ligand.

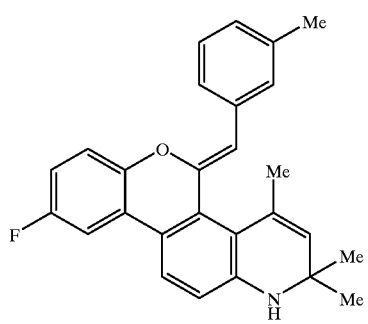

Jones, et al, described compound 3 (U.S. Pat. No. 5,696,127) as a PR ligand.

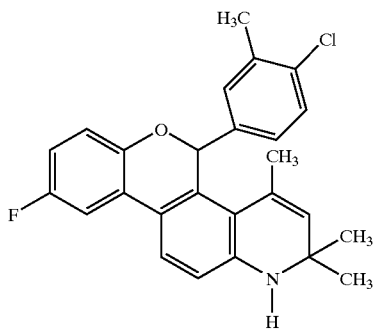

Zhi, et al, described lactones 4, 5 and 6 as PR antagonists (J. Med. Chem., 41, 291, 1998).

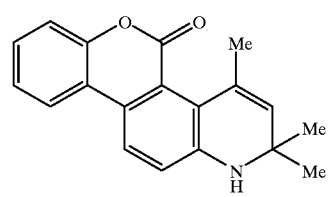

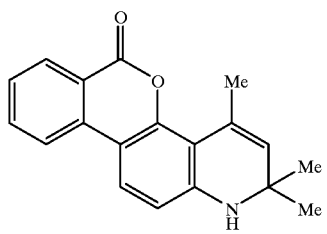

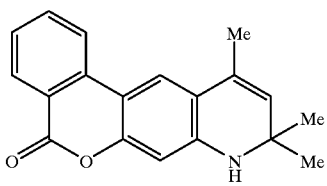

Zhi, et al, described the ether 7 as a PR antagonist (*J. Med. Chem.*, 41, 291, 1998).

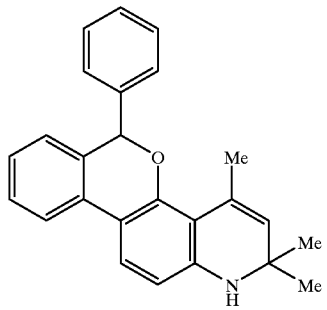

Combs, et al., disclosed the amide 8 as a ligand for the PR (*J. Med. Chem.*, 38, 4880, 1995).

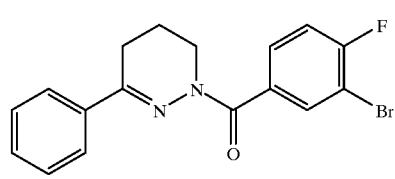

Perlman, et. al., described the vitamin D analog 9 as a PR ligand (*Tet. Letters*, 35, 2295, 1994).

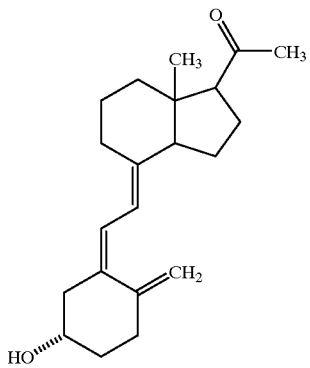

Hamann, et al, described the PR antagonist 10 (*Ann. N.Y. Acad. Sci.*, 761, 383, 1995).

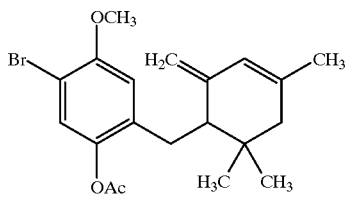

Chen, et al, described the PR antagonist 11 (Chen, et al, POI-37, 16$^{th}$ Int. Cong. Het. Chem., Montana, 1997).

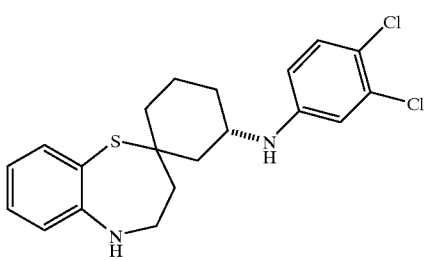

Kurihari, et. al., described the PR ligand 12 (*J. Antibiotics*, 50, 360, 1997).

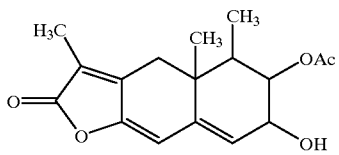

Narr et al. (German Patent, DE 3633861, CA 109:22973) claimed that imidazobenzoxazinones, e.g. A, as cardotonics; Benzoxazin-2-ones, such as brofoxine (B), being active as an anxiolytic was reported by Hartmann et al. (*Proc. West. Pharmacol. Soc.* 21, 51–55 (1978)); More recently, a number of patents (e.g. Young et al. WO95/20389; Christ et al. WO98/14436) claimed quinazolin-2-ones and benzoxazin-2-ones such as compound C1 and C2 as inhibitors of HIV reverse transcriptase.

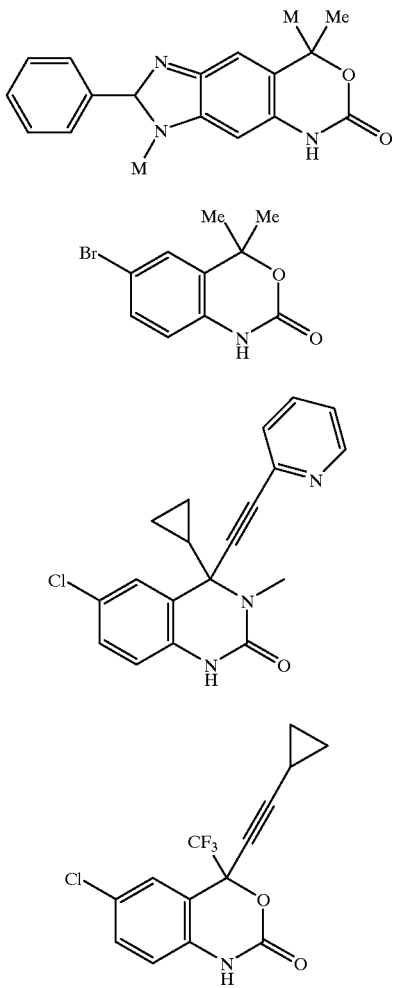

The compounds in the present invention contain a pendent aromatic substituent. The aromatic substituents proved to be critical for the resultant compounds being active as progesterone receptor modulators and have broad structural diversity which may consist of aryl, substituted aryl, heteroaryl or substituted heteroaryl group.

DESCRIPTION OF THE INVENTION

This invention provides compounds of Formula (I):

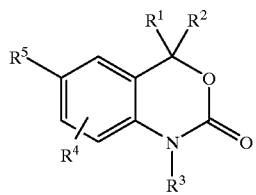

wherein:

$R^1$ and $R^2$ are independent substituents selected from the group of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

or $R^1$ and $R^2$ are fused to form:

a) an optionally substituted 3 to 8 membered spirocyclic alkyl ring;

b) an optionally substituted 3 to 8 membered spirocyclic alkenyl; or c) an optionally substituted 3 to 8 membered heterocyclic ring containing one to three heteroatoms from the group including O, S and N; the spirocyclic rings of a), b) and c) being optionally substituted by from 1 to 4 groups selected from fluorine, $C_1$ to $C_6$ alkyl, $C_1$ to $C_6$ alkoxy, $C_1$ to $C_6$ thioalkyl, —$CF_3$, —OH, —CN, $NH_2$, —NH($C_1$ to $C_6$ alkyl), or —N($C_1$ to $C_6$ alkyl)$_2$;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, $COR^C$;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is H, halogen, CN, $NO_2$, $C_1$ to $C_6$ alkyl, substituted $C_1$ to $C_6$ alkyl, alkynyl, or substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is selected from a) or b)

a) $R^5$ is a trisubstituted benzene ring containing the substituents X, Y and Z as shown below:

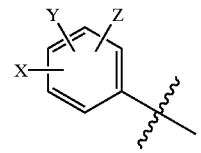

wherein:

X is taken from the group including halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, $COR^D$, $OCOR^D$, or $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents taken from the group including H, halogen, CN, $NO_2$, amino, aminoalkyl, $C_1$ to $C_3$ alkoxy, $C_1$ to $C_3$ alkyl, or $C_1$ to $C_3$ thioalkoxy; or b) $R^5$ is a five or six membered ring with 1, 2, or 3 heteroatoms from the group including O, S, SO, $SO_2$ or NR⁶ and containing one or two independent substituents from the group including H, halogen, CN, NO₂, amino, and C₁ to C₃ alkyl, C₁ to C₃ alkoxy, C₁ to C₃ aminoalkyl, COR^F, or NR^G COR^F;

R^F is H, C₁ to C₃ alkyl, substituted C₁ to C₃ alkyl, aryl, substituted aryl, C₁ to C₃ alkoxy, substituted C₁ to C₃ alkoxy, C₁ to C₃ aminoalkyl, or substituted C₁ to C₃ aminoalkyl;

R^G is H, C₁ to C₃ alkyl, or substituted C₁ to C₃ alkyl;

R⁶ is H or C₁ to C₃ alkyl;

or pharmaceutically acceptable salt thereof.

Preferred compounds of this invention include those of Formula I

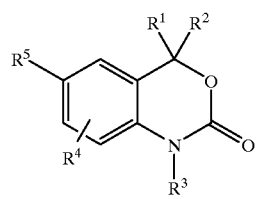

wherein:

R¹ is H, C₁ to C₆ alkyl, substituted C₁ to C₆ alkyl, C₃ to C₈ cycloalkyl, substituted C₃ to C₈ cycloalkyl, aryl, substituted aryl, heterocyclic, substituted heterocyclic, COR^A, or NR^B COR^A;

R² is H, C₁ to C₆ alkyl, substituted C₁ to C₆ alkyl, C₂ to C₆ alkenyl, substituted C₂ to C₆ alkenyl, C₃ to C₁ cycloalkyl, substituted C₃ to C₈ cycloalkyl, aryl, substituted aryl, heterocyclic, substituted heterocyclic, COR^A, or NR^B COR^A; or R¹ and R² are fused to form spirocyclic alkyl as a 3 to 8 membered spirocyclic ring, substituted spirocyclic alkyl constructed by fusing R¹ and R² to form a 3 to 8 membered spirocyclic ring, spirocyclic alkenyl constructed by fusing R¹ and R² to form a 3 to 8 membered spirocyclic ring, substituted spirocyclic alkenyl constructed by fusing R¹ and R² to form a 3 to 8 membered spirocyclic ring, spirocyclic alkyl constructed by fusing R¹ and R² to form a 3 to 8 membered spirocyclic ring and containing one to three heteroatoms from the group including O, S and N; substituted spirocyclic alkyl constructed by fusing R¹ and R² to form a 3 to 8 membered spirocyclic ring and containing one to three heteroatoms from the group including O, S and N; the spirocyclic rings made by fusing R¹ and R² being optionally substituted by from 1 to 4 groups selected from fluorine, C₁ to C₆ alkyl, C₁ to C₆ alkoxy, C₁ to C₆ thioalkyl, —CF₃, —OH, —CN, NH₂, —NH(C₁ to C₆ alkyl), or —N(C₁ to C₆ alkyl)₂;

R^A is H, C₁ to C₃ alkyl, substituted C₁ to C₃ alkyl, aryl, substituted aryl, C₁ to C₃ alkoxy, substituted C₁ to C₃ alkoxy, C₁ to C₃ aminoalkyl, or substituted C₁ to C₃ aminoalkyl;

R^B is H, C₁ to C₃ alkyl, or substituted C₁ to C₃ alkyl;

R³ is H, OH, NH₂, C₁ to C₆ alkyl, substituted C₁ to C₆ alky, C₃ to C₆ alkenyl, substituted C₁ to C₆ alkenyl, alkynyl, or substituted alkynyl, COR^C;

R^C is H, C₁ to C₄ alkyl, substituted C₁ to C₄ alkyl, aryl, substituted aryl, C₁ to C₄ alkoxy, substituted C₁ to C₄ alkoxy, C₁ to C₄ aminoalkyl, or substituted C₁ to C₄ aminoalkyl;

R⁴ is H, halogen, CN, NO₂, C₁ to C₆ alkyl, substituted C₁ to C₆ alkyl, C₁ to C₆ alkoxy, substituted C₁ to C₆ alkoxy, amino, C₁ to C₆ aminoalkyl, or substituted C₁ to C₆ aminoalkyl;

R⁵ is a trisubstituted benzene ring containing the substituents X, Y and Z as shown below:

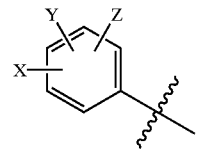

X is taken from the group including halogen, CN, C₁ to C₃ alkyl, substituted C₁ to C₃ alkyl, C₁ to C₃ alkoxy, substituted C₁ to C₃ alkoxy, C₁ to C₃ thioalkoxy, substituted C₁ to C₃ thioalkoxy, amino, C₁ to C₃ aminoalkyl, substituted C₁ to C₃ aminoalkyl, NO₂, C₁ to C₃ perfluoroalkyl, 5 membered heterocyclic ring containing 1 to 3 heteroatoms, COR^D, OCOR^D, or NR^E COR^D;

R^D is H, C₁ to C₃ alkyl, substituted C₁ to C₃ alkyl, aryl, substituted aryl, C₁ to C₃ alkoxy, substituted C₁ to C₃ alkoxy, C₁ to C₃ aminoalkyl, or substituted C₁ to C₃ aminoalkyl;

R^E is H, C₁ to C₃ alkyl, or substituted C₁ to C₃ alkyl;

Y and Z are independent substituents taken from the group including H, halogen, CN, NO₂, C₁ to C₃ alkoxy, C₁ to C₃ alkyl, or C₁ to C₃ thioalkoxy;

or

R⁵ is a five or six membered ring with 1, 2, or 3 heteroatoms from the group including O, S, SO, SO₂ or NR⁶ and containing one or two independent substituents from the group including H, halogen, CN, NO₂, amino, and C₁ to C₃ alkyl, or C₁ to C₃ alkoxy;

R⁶ is H, or C₁ to C₃ alkyl;

or pharmaceutically acceptable salt thereof.

Other preferred compounds are those of Formula I

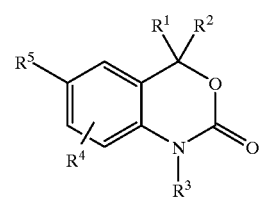

wherein:

R¹=R² and are selected from the group which includes C₁ to C₃ alkyl, substituted C₁ to C₃ alkyl, spirocyclic alkyl constructed by fusing R¹ and R² to form a 3 to 6 membered spirocyclic ring;

R³ is H, OH, NH₂, C₁ to C₆ alkyl, or substituted C₁ to C₆ alkyl, COR^C;

R^C is H, C₁ to C₄ alkyl, or C₁ to C₄ alkoxy;

R⁴ is H, halogen, CN, NO₂, C₁ to C₃ alkyl, substituted C₁ to C₃ alkyl, C₁ to C₃ alkoxy, or substituted C₁ to C₃ alkoxy;

R⁵ is a disubstituted benzene ring containing the substituents X, and Y as shown below:

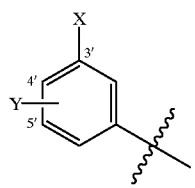

X is taken from the group including halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, $C_1$ to $C_3$ thioalkoxy;

Y is a substituent from the group including H, halogen, CN, $NO_2$, $C_1$ to $C_3$ alkoxy, $C_1$ to $C_4$ alkyl, $C_1$ to $C_3$ thioalkoxy;

or $R^5$ is a five membered ring with the structure

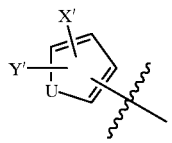

U is O, S, or $NR^6$, $R^6$ is H, or $C_1$ to $C_3$ alkyl, or $C_1$ to $C_4$ $CO_2$alkyl;

X' is from the group including halogen, CN, $NO_2$, or $C_1$ to $C_3$ alkyl and $C_1$ to $C_3$ alkoxy, provided that when U is $NR^6$, then X' is not CN;

Y' is from the group including H and $C_1$ to $C_4$ alkyl;

or $R^5$ is a six membered ring with the structure:

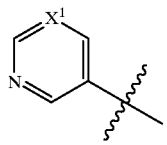

$X^1$ is N or $CX^2$;

$X^2$ is halogen, CN, alkoxy, or $NO_2$;

or pharmaceutically acceptable salt thereof

Further preferred compounds are those of Formula I

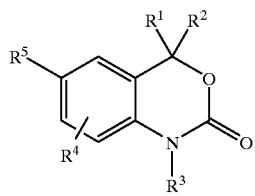

I wherein:

$R^1=R^2$ and are selected from the group which includes $CH_3$ and spirocyclic alkyl constructed by fusing $R^1$ and $R^2$ to form a 6 membered spirocyclic ring $R^3$ is H, OH, $NH_2$, $CH_3$, substituted methyl, or $COR^C$;

$R^C$ is H, $C_1$ to $C_3$ alkyl, or $C_1$ to $C_4$ alkoxy;

$R^4$ is H, halogen, $NO_2$, CN, or $C_1$ to $C_3$ alkyl;

$R^5$ is a disubstituted benzene ring containing the substituents X and Y as shown below:

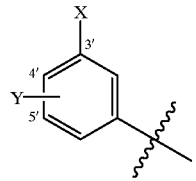

X is taken from the group including halogen, CN, methoxy, $NO_2$, or 2-thiazole;

Y is H or F;

or $R^5$ is a five membered ring with the structure:

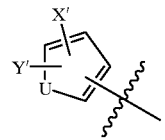

U is O, S, or NH,

X' is halogen, CN, or $NO_2$, provided that when U is $NR^6$, X' is not CN;

Y' is H or $C_1$ to $C_4$ alkyl and pharmaceutically acceptable salts.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having one to eight carbon atoms, preferably one to six carbon atoms; "alkenyl" is intended to include both straight- and branched-chain alkyl group with at least one carbon-carbon double bond and two to eight carbon atoms, preferably two to six carbon atoms; "alkynyl" group is intended to cover both straight- and branched-chain alkyl group with at least one carbon-carbon triple bond and two to eight carbon atoms, preferably two to six carbon atoms.

The terms "substituted alkyl", "substituted alkenyl", and "substituted alkynyl" refer to alkyl, alkenyl, and alkynyl as just described having from one to three substituents selected from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but not limited to phenyl, naphthyl, biphenyl, anthryl, tetrahydronaphthyl, phenanthryl.

The term "substituted aryl" refers to aryl as just defined having one to four substituents from the group including halogen, CN, OH, NO$_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one to four substituents selected from the group which includes halogen, CN, OH, NO$_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atom. The term "halogen" refers to Cl, Br, F, or I.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "prodrug" forms, which, when administered in such form, convert to the active moiety in vivo.

This invention includes pharmaceutical compositions comprising one or more compounds of this invention and a pharmaceutically acceptable carrier or excipient. The invention also includes methods of treatment which comprise administering to a mammal a pharmaceutically effective amount of one or more compounds as described above as antagonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The compounds of this invention can be prepared following the Schemes illustrated below:

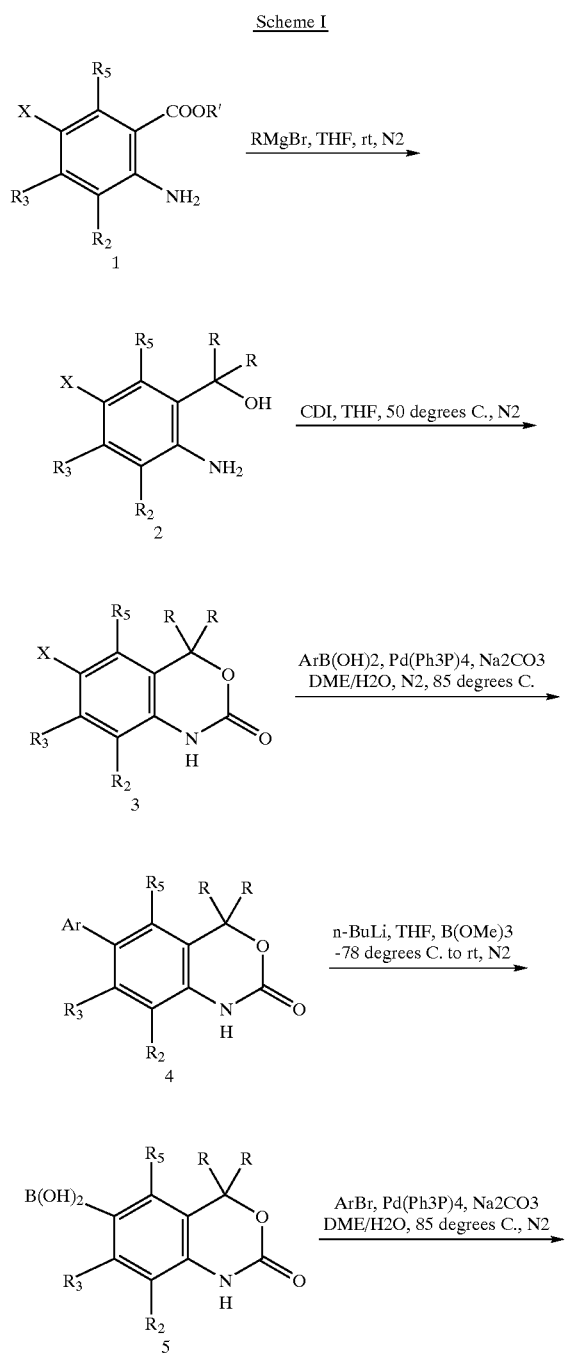

Scheme I

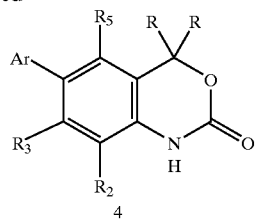

4

As demonstrated in Scheme I, the compounds of this invention are generally prepared by employing the suitable coupling reaction as a final step. An appropriately substituted ortho-amino benzoic acid or its derivatives such as ethyl ester (X=Br, I, Cl, or a latent coupling precursor such as alkoxy group which can be converted into OTf group suitable in the coupling reaction.) was treated with a suitable organo metallic reagent, e.g. Grignard reagent, in appropriate nonprotic solvents which include but not limited to THF or ether to give ortho-amino carbinol 2 under an inert atmosphere such as argon or nitrogen at −78° C. to room temperature. Ring closure of carbinol 2 to yield benzoxazin-2-ones 3 is commonly effected by a condensing agent such as carbonyldiimidazole, phosgene, dimethylcarbonate, or diethylcarbonate in a suitable nonprotic solvent such as THF at temperatures ranging from room temperature to 65° C. The arylation of benzoxazin-2-ones 3 to yield 4 can be effected by various coupling reactions including Suzuki, Stille reactions. These reactions are commonly performed in the presence of transition metallic catalyst, e.g., palladium or nickel complex often with phosphino ligands, e.g., $Ph_3P$, 1,1'-bis(diphenylphosphino)ferrocene, 1,2-bis (diphenylphosphino)ethane or palladium salt such as palladium acetate. Under this catalytic condition, an appropriately substituted nucleophilic reagent, e.g., aryl boronic acid, arylstannane, or aryl zinc compound, is coupled with benzoxazinones 3 to give 4. If a base is needed in the reaction, the commonly used bases include but not limited to sodium bicarbonate, sodium carbonate, potassium phosphate, barium carbonate, potassium acetate, or cesium fluoride. The most commonly used solvents in these reactions include benzene, DMF, isopropanol, toluene, ethanol, DME, ether, acetone or a mixture of any one of these solvent and water. The coupling reaction is generally executed under an inert atmosphere such as nitrogen or argon at temperatures ranging from room temperature to the boiling point of the solvent or solvent system or mixture.

Benzoxazinones 3 can be converted into a nucleophile such as boronic acid which can be coupled with an appropriate electrophile, e.g., aryl bromide or aryl iodide, to yield 4 employing the coupling reaction condition as described above. The transformation of 3 into 5 can be effected by treating 3 with an organo metallic reagent, e.g., n-BuLi, in a nonprotic solvent such as THF or ether followed by quenching the reaction solution with a suitable electrophile such as trimethyl borate, triisopropyl borate, bishexalkyl tin reagent, or zinc chloride at temperatures ranging from −78° C. to reflux temperature under an inert atmosphere such as argon or nitrogen.

Scheme Ia

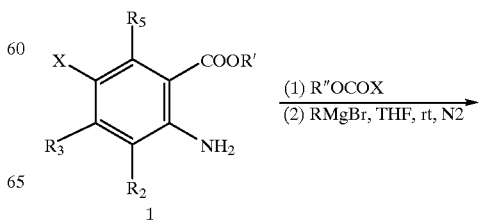

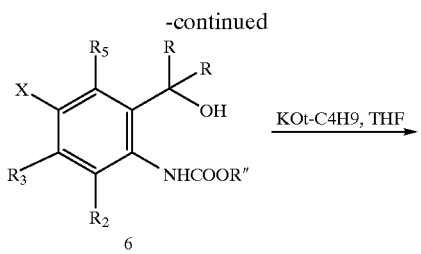

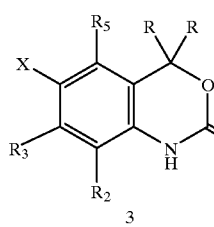

Scheme Ia illustrates an alternative approach leading to the benzoxazinones 3. Thus, an appropriate aniline 1 is protected with a suitable alkoxy carbonyl protective group including but not limited to allyloxy carbonyl, t-butoxy carbonyl, benzoxy carbonyl, ethoxy carbonyl, or methoxy carbonyl in a suitable solvent such as THF, acetonitrile, with or without presence of a base either as a catalyst or as an acid scavenger. The protected aniline is then treated with a suitable organo metallic reagent such as organo lithium agent or Grignard reagent in the same fashion as to prepare compound 2 to give the carbinol 6. The treatment of 6 with a suitable base such as potassium t-butoxide, n-butyl lithium, potassium hydroxide in an appropriate solvent such as toluene, THF, alcohol under an inert atmosphere such as nitrogen or argon at the temperature ranging from room temperature to the boiling point of the relevant solvent to afford benzoxazinones 3.

Scheme II describes the procedures to prepare benzoxazinones bearing two different substituents at position-4. The Weinreb amide 8 can be prepared from an appropriately substituted isatoic anhydride 7 when treated with N-, O-dimethylhydroxyl-amine hydrochloride salt in a protic solvent such as ethanol, isopropanol at reflux under an inert atmosphere such as argon or nitrogen. Coupling of amide 8 with an aryl electrophile such as aryl boronic acid or arylstannane to give 9 can be effected by employing a typical coupling reaction such as Suzuki, Stille coupling procedure in a similar fashion as described for the preparation of benzoxazinones 4. Treatment of Weinreb amide 9 with organo metallic compounds, e.g., alkyllithium, alkynyllithium, aryllithium, or their Grignard counterpart in a nonprotic solvent such as THF or ether under an inert atmosphere such as argon or nitrogen at −78° to room temperature affords amino ketone 10. Conversion of ketone 10 to carbinol 11 can be effected by treatment of 10 with an organo metallic reagent such as alkyl, alkynyl, or aryl Grignard compound in a nonprotic solvent such as THF or ether under an inert atmosphere such as argon or nitrogen at −78° C. to room temperature. Conversion of ketone 10 to carbinol 11 can also be effected by reduction of ketone group of 10 to the carbinol moiety of 11 using an appropriate reducing reagent such as lithium aluminum hydride, sodium borohydride in a suitable solvent such as THF, ether, or anhydrous alcohol under an inert atmosphere in the temperature ranging from 0° C. to the boiling point of the solvent. Ring closure of carbinol 11 to produce the compounds of this invention can be accomplished with condensing agents such as carbonyldiimidazole, phosgene, dimethylcarbonate, or diethylcarbonate in a suitable nonprotic solvent such as THF at temperatures ranging from room temperature to 65° C.

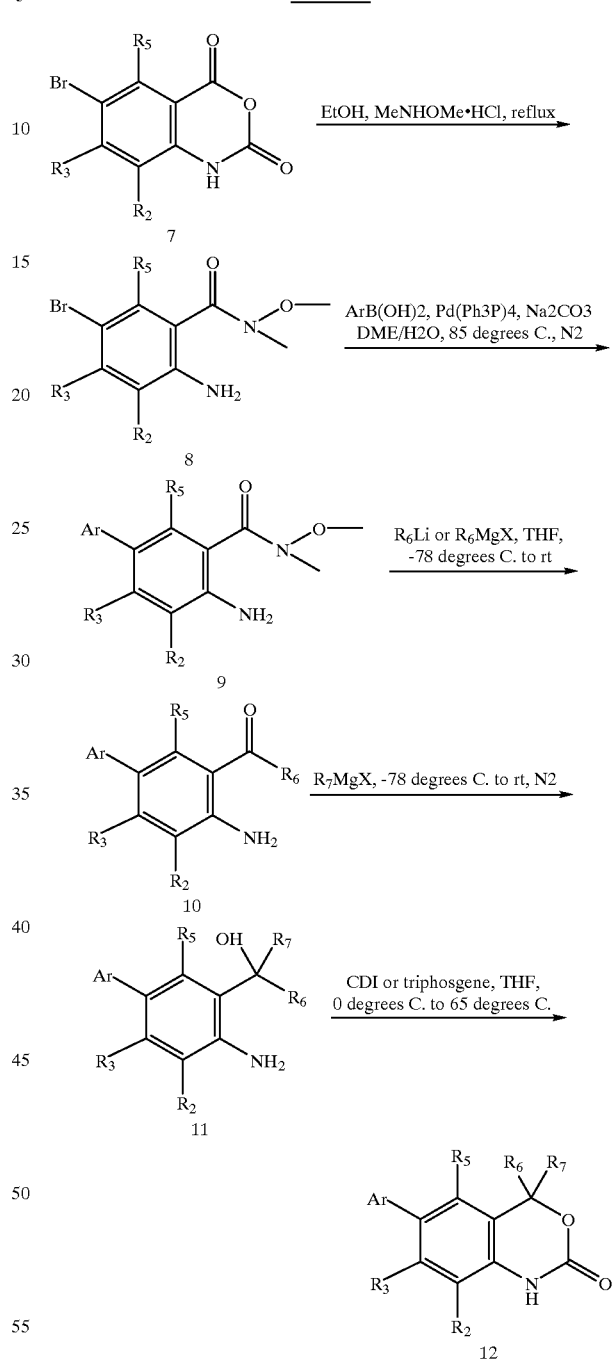

Alternatively, ortho-amino ketone 10 can be prepared by treatment of ortho-amino benzonitrile 14 with an organo metallic compound such as organo lithium reagent or Grignard reagent in a suitable solvent such as THF or ether under an inert atmosphere such as argon or nitrogen at temperatures ranging from −78° C. to room temperature as illustrated in Scheme III. Benzonitrile 14 can be readily prepared from an appropriately substituted benzonitrile such as bromobenzonitrile 13 using a suitable coupling reaction such as Stille or Suzuki protocol carried out in a similar fashion as described for the preparation of the Weinreb amide 9.

Scheme III

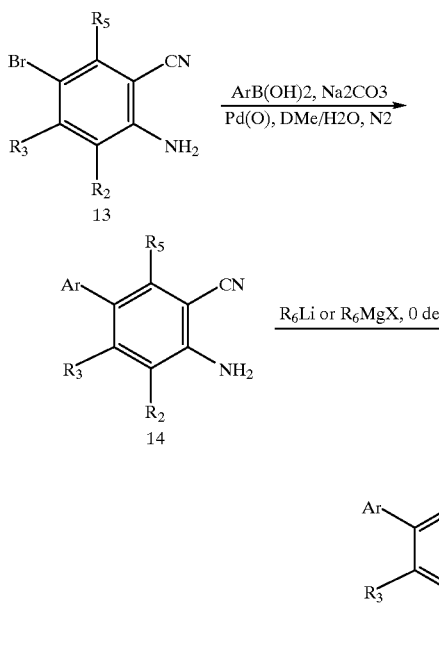

Scheme IV depicts an approach to prepare benzoxazinones with a low perfluoroalkyl substituent at position-4, e.g. $R_6$ is trifluorormethyl group. An appropriately substituted chloroaniline 15 was protected with a suitable protective reagent such as pivaloyl chloride or di-tert-butyl pyrocarbonate to give protected aniline 16 in a suitable solvent such as acetonitrile, acetone, THF, methylene chloride, or a mixture of solvent such as methylene chloride and water under an inert atmosphere such as argon or nitrogen at temperatures ranging from 0° C. to 70° C. A suitable base such as sodium carbonate, sodium bicarbonate, or potassium carbonate may be needed when the reaction produces an acid as a side-product such as hydrochloride. Treatment of 16 with an appropriate alkyllithium such as n-butyllithium or s-butyllithium followed by reaction with a low perfluorocarboxy derivatives, e.g., trifluoroacetyl chloride, 1-(trifluoroacetyl)-imidazole, or ethyl trifluoroacetate in a nonprotic solvent such as ether or THF under an inert atmosphere such as argon or nitrogen at −78° C. to ambient temperature gives the protective ortho-amino ketones. Subsequent removal of the protecting group can be effected by reaction of protected amino ketones with a suitable acid such as TFA, 3N aqueous hydrochloride solution in a suitable solvent such as methylene chloride or water at 0° C. to boiling point of the solvent to afford ortho-amino ketone 17. The preparation of 6-chlorobenzoxazinones 19 from 17 can be accomplished in the same fashion as described for the synthesis of benzoxazinone 12 from ketone 10. Coupling of 19 with an aryl group to yield the compounds of this invention, 12 as shown in scheme IV can be effected by a nickel complex catalyzed coupling reaction. The palladium catalysts proved not to be an efficient catalyst in this coupling process. The coupling reaction of 19 with an appropriate aryl boronic acid can be accomplished in the presence of a suitable base such as potassium phosphate and a catalyst of nickel (0 or II) complex, e.g. a nickel complex of dppe, dppf, or triphenylphosphine. The most commonly used solvents in the reaction include dioxane or THF. The coupling reaction is generally executed under an inert atmosphere such as nitrogen or argon at temperatures ranging from ambient temperature to 95° C.

Scheme IV

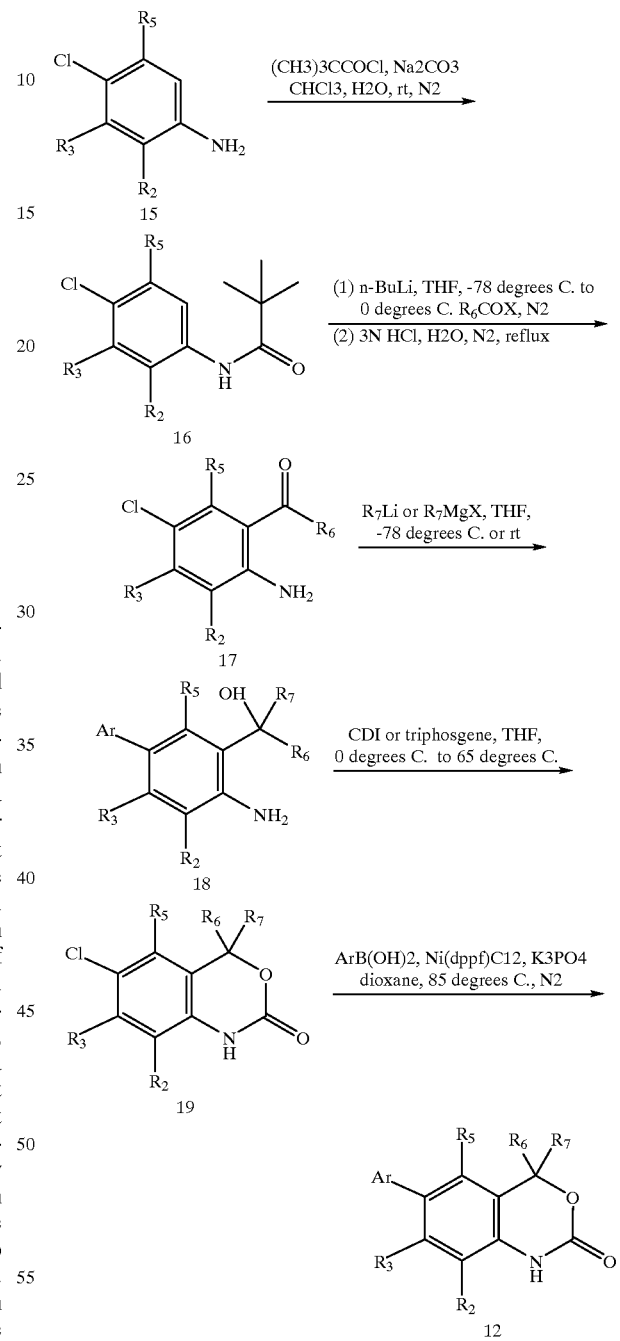

As illustrated in Scheme V, the compounds 6 or 12 can be further derivatized at position-1 via numerous approaches leading to a variety of novel cyclocarbamate derivatives including 1-alkyl, 1-substituted alkyl, 1-carbonyl, 1-substituted carbonyl, 1-carboxy, substituted 1-carboxy derivatives. For examples, alkyl or substituted alkyl derivatives 20 can be formed by treatment of carbamate 12 or 6 with a suitable base such as sodium hydride in suitable solvent such as DMF under an inert atmosphere such as argon or nitrogen followed by addition of an appropriate electrophile such as alkyl or substituted alkyl bromide, iodide, or triflate. Such a transformation of 12 or 6 at position-1 can also be effected using biphasic conditions as indicated in scheme V in which alkylation is executed using a biphasic catalyst such as tributylammonium bromide in a suitable solvent such as acetonitrile. Another example of this type of modification includes, but is not limited to, the one depicted in scheme V where heating 12 or 6 with triethyl orthoformate affords 1-substituted derivatives of compound 12 or 6.

Scheme V

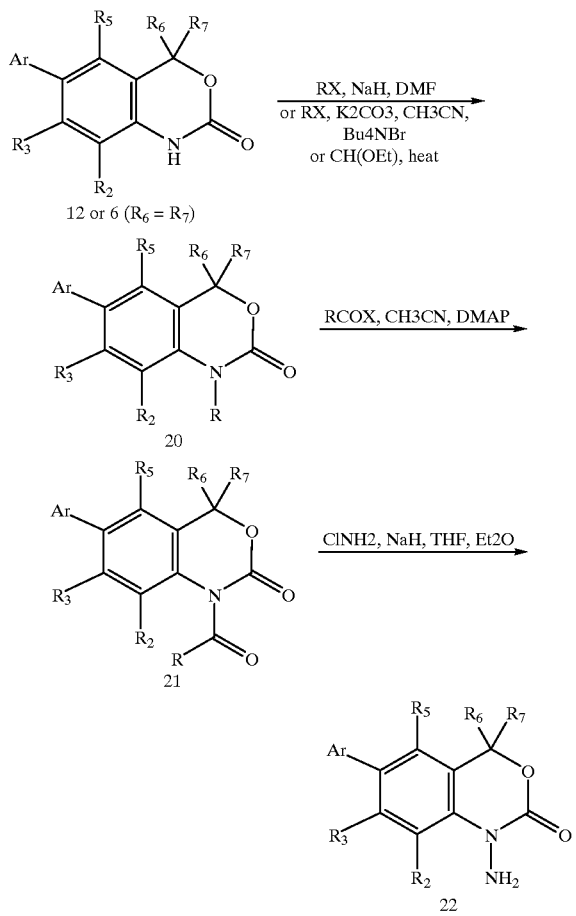

The acylation or carboxylation of the compound 12 or 6 at position-1 to give compound 21 can be readily effected by treatment of 12 or 6 with a suitable acylating or carboxylating reagent such as di-t-butyl dicarbonate in the presence of a suitable basic catalyst such as DMAP in a suitable solvent such as acetonitrile under an inert atmosphere such as argon or nitrogen. The amination of position-1 of compound 12 or 6 to give 22 can be accomplished using a suitable aminating reagent such as chloroamine in the presence of a suitable base, such as sodium hydride, in a suitable solvent, such as THF or diethyl ether, following literature procedures (Metlesics et al. *J. Org. Chem.* 30, 1311(1965).)

EXAMPLE 1

2-(2-Amino-5-bromophenyl)propan-2-ol

A solution of 2-amino-5-bromobenzoic acid (10 g, 46 mmol) in dry THF (200 mL) was treated at −78° C. under nitrogen with a solution of methylmagnesium bromide in ether (3.0 M, 90 mL, 270 mmol). The reaction mixture was slowly warmed to ambient temperature, kept stirring for 48 hours under nitrogen and then poured into a cold 0.5 N aqueous hydrochloride solution (300 mL). The mixture was neutralized with aqueous 1 N sodium hydroxide solution and ethyl acetate (300 mL) was added. The organic layer was separated and aqueous layer was extracted with ethyl acetate (3×100 mL). The combined organic layers were washed with brine and dried (MgSO$_4$). After removal of solvent in vacuo, the residue was purified by a silica gel flash chromatography (hexane:ethyl acetate/3:2) to give 2-(2-amino-5-bromophenyl)propan-2-ol as off-white solid (6 g, 57%): mp 62–63° C.; $^1$H-NMR (CDCl$_3$) δ7.19 (d, 1H, J=2.3 Hz), 7.12 (dd, 1H, J=8.4, 2.3 Hz), 6.51 (d, 1H, J=8.4 Hz), 4.70 (s, 2H), 1.82 (s, 1H), 1.65 (s, 6H).

EXAMPLE 2

6-Bromo-4,4-dimethyl-1,4-dihydro-benzo[d][1,3]oxazin-2-one

To a solution of 2-(2-amino-5-bromophenyl)propan-2-ol (18 g, 78 mmol) in dry THF (150 mL) was added 1,1'-carbonyldiimidazole (15.5 g, 94 mmol) under nitrogen. The reaction solution was heated at 50° C. overnight. The solvent was removed in vacuo and the residue was dissolved in ethyl acetate (100 mL). The solution was washed with 1N aqueous hydrochloride solution (2×40 mL), brine (20 mL), and dried with MgSO$_4$. After removal of solvent in vacuo, 6-bromo-4,4-dimethyl-1,4-dihydro-benzo[d][1,3]oxazin-2-one was obtained as a white solid (20 g, 100%): mp 199–200° C.; $^1$H-NMR (DMSO-d$_6$) δ10.32 (s, 1H, D$_2$O exchangeable), 7.48 (d, 1H, J=2.1 Hz), 7.43 (dd, 1H, J=8.5, 2.1 Hz), 6.84 (d, 1H, J=8.4 Hz), 161 (s, 6H).

EXAMPLE 3

6-Iodo-4,4-dimethyl-1,4-dihydro-benzo[d][1,3]oxazin-2-one

The product was prepared, from 2-amino-5-iodobenzoic acid following the procedures of Example 1 and 2, as a white solid: mp 196–197° C.; $^1$H-NMR (DMSO-d$_6$)δ10.30 (s, 1H, D$_2$O exchangeable), 7.58 (m, 2H), 6.71 (d, 1H, J=8.4 Hz), 158 (s, 6H). MS (EI) m/z 326 ([M+Na]$^+$, 100%). Anal. Calc. For C$_{10}$H$_{10}$INO$_2$: C, 39.63, H, 3.33, N, 4.62. Found: C, 39.25, H, 3.24, N, 4.49.

EXAMPLE 4

(1,4-Dihydro-4,4-dimethyl-2-oxo-2H-3,1-benzoxazin-6-yl)boronic acid

To a solution of 6-bromo-4,4-dimethyl-1,4-dihydro-benzo[d][1,3]oxazin-2-one (2 g, 7.8 mmol) in anhydrous THF (60 mL) was added a solution of n-BuLi in hexane (10 M, 2.4 mL, 24 mmol) at −78° C. under nitrogen. After stirring at −78° C. for 30 minutes, a slurry was obtained and treated with triisopropyl borate (6.5 mL, 28 mmol). The reaction medium was slowly warmed to ambient temperature and quenched with 1N aqueous hydrochloric acid solution (60 mL). Ethyl acetate (100 mL) was added and organic layer was separated, and aqueous layer was extracted with ethyl acetate (3×60 mL). The combined organic layer was washed with brine and dried with MgSO$_4$. The solvent was removed in vacuo and the residue was purified by a silica gel flash chromatography (ethyl acetate:hexane/2: 1) to afford (1,4-dihydro-4,4-dimethyl-2-oxo-2H-3,1-benzoxazin-6-yl)

boronic acid as a white solid (1.4 g, 81%): mp 249–250° C.; $^1$H-NMR (DMSO-d$_6$) δ10.21 (s, 1H, D$_2$O exchangeable), 7.90–7.95 (br s, 2H, D$_2$O exchangeable ), 7.67 (m, 2H), 6.79 (d, 1H, J=7.8 Hz), 1.61 (s, 6H); MS (ESI) m/z 222 ([M+H]$^+$, 87%).

EXAMPLE 5

6-(3-Chlorophenyl)-4,4-dimethyl-1,4-dihydrobenzo[d][1,3]oxazin-2-one (Procedure A)

A mixture of 6-bromo4,4-dimethyl-1,4-dihydro-benzo[d][1,3]oxazin-2-one (1.5 g, 5.9 mmol), 3-chlorophenyl boronic acid (1.83 g, 11.7 mmol), tetrakis(triphenylphosphine)-palladium (0) (0.35 g, 0.3 mmol), and sodium carbonate (2.48 g, 23.4 mmol) in a mixture of DME and water (40 mL/10 mL) was degassed to remove the oxygen and then heated at 85° C. under a blanket of nitrogen for 3 hours. The reaction mixture was cooled to ambient temperature and quenched with a saturated aqueous ammonium chloride solution (20 mL). Ethyl acetate (50 mL) was added and organic layer was separated. The aqueous layer was extracted with ethyl acetate (3×5 mL). The combined organic layers were washed with brine and dried with MgSO$_4$. The solvent was removed in vacuo and the residue was purified by a silica gel flash chromatography (hexane:ethyl acetate/2:1) to afford 6-(3-chlorophenyl)4,4-dimethyl-1,4-dihydrobenzo[d][1,3]oxazin-2-one as a yellowish solid (1.4 g, 82%): mp 158–159° C.; $^1$H-NMR (DMSO-d$_6$) δ10.31 (s, 1H, D$_2$O exchangeable), 7.75 (s, 1H), 7.61 (m, 3H), 7.46 (t, 1H, J=7.9 Hz), 7.39 (dd, 1H, J=7.0, 1.1 Hz), 6.96 (d, 1H, J=8.6 Hz), 1.68 (s, 6H); Anal. Calc. For C$_{16}$H$_{14}$ClNO$_2$.0.1 H$_2$O: C, 66.37, H, 4.94, N, 4.84. Found: C, 66.14, H, 4.61, N, 4.71.

EXAMPLE 6

6-(3-Methoxy-phenyl)4,4-dimethyl-1,4-dihydro-benzo[d][1,3]-oxazin-2one

Prepared according to Procedure A from 6-bromo-4,4-dimethyl-1,4-dihydro-benzo[d][1,3]oxazin-2-one and 3-methoxyphenyl boronic acid. Yellow solid: mp 164–165° C.; $^1$H-NMR (DMSO-d$_6$) δ10.3 (s, 1H), 7.56 (m, 2H), 7.36 (t, 1H, J=7.89 Hz), 7.20 (m, 2H), 6.96 (d, 1H, J=8.88 Hz), 6.91 (dd, 1H, J=8.13, 2.35 Hz), 3.8 (s, 3H), 1.7 (s, 6H); MS (ESI) m/z 284 ([M+H]$^+$, 30%); Anal. Calc. For C$_{17}$H$_{17}$NO$_3$: C, 72.07, H, 6.05, N, 4.94. Found: C, 70.58, H, 5.73, N, 4.67

EXAMPLE 7

6-(2-Chloro-phenyl)4,4-dimethyl-1,4-dihydro-benzo[d][1,3]oxazin-2-one

Prepared according to Procedure A from 6-bromo-4,4-dimethyl-1,4-dihydro-benzo[d][1,3]oxazin-2-one and 2-chlorophenyl boronic acid. White solid: mp 181–182° C.; MS (ESI) m/z 288 ([M+H]$^+$, 70%); Anal. Calc. For C$_{16}$H$_{14}$ClNO$_2$: C, 66.79 H, 4.90, N, 4.87. Found: C, 66.78, H, 4.82, N, 4.55

EXAMPLE 8

6-(4-Chloro-phenyl)-4,4-dimethyl-1,4-dihydro-benzo[d][1,3]-oxazin-2-one

Prepared according to Procedure A from 6-bromo-4,4-dimethyl-1,4-dihydro-benzo[d][1,3]oxazin-2-one and 4-chlorophenyl boronic acid. White solid: mp 255–257° C.; $^1$H-NMR (DMSO-d$_6$) δ10.3 (s, 1H), 7.7 (d, 2H, J=8.52 Hz), 7.55 (m, 2H), 7.5 (d, 2H, J=8.52 Hz), 6.96 (d, 1H, J=8.52 Hz), 1.7 (s, 6H); MS (ESI) m/z 288 ([M+H]$^+$, 70%); Anal. Calc. For C$_{16}$H$_{14}$ClNO$_2$: C, 66.79, H, 4.90, N, 4.87. Found: C, 66.34, H, 4.76, N, 4.75

EXAMPLE 9

6-(3-Chloro-phenyl)4-methyl-1,4-dihydro-benzo[d][1,3]oxazin-2-one

To a solution of 1-(4-amino-3'-chloro-biphenyl-3-yl)-ethanone (see example 35, 0.15 g, 0.61 mmol) in anhydrous methanol was added sodium borohydride (0.07 g, 1.03 mmol) at room temperature (rt) under nitrogen. After 15 minutes, the reaction mixture was treated with ice-water. Ethyl acetate (30 mL) was then added, the organic layer was separated, and aqueous layer was extracted with ethyl acetate (3×20 mL). The combined organic layers were washed with brine (10 mL) and dried over MgSO$_4$. After removal of solvent, the residue obtained was crystallized from toluene to afford 1-(4-amino-3'-chloro-biphenyl-3-yl)-ethanol as a white solid (0.087 g, 58%): $^1$H-NMR (DMSO-d$_6$) δ7.55 (t, 1H, J=1.4 Hz), 7.50 (d, 1H, J=7.8 Hz), 7.44 (d, 1H, J=2.1 Hz), 7.39 (t, 1H, J=8.2 Hz), 7.31–7.21 (m, 2H), 6.68 (d, 1H, J=8.1 Hz), 5.25 (s, 2H), 5.20 (m, 1H), 4.83 (m, 1H), 1.35 (d, 3H, J=8.8 Hz); MS (EI) m/z 247 (M$^+$).

A mixture of 1-(4-amino-3'-chloro-biphenyl-3-yl)-ethanol (0.03 g, 0.13 mmol) and triphosgene (0.01 g, 0.04 mmol) in dry THF (3 mL) was stirred under a blanket of nitrogen for 10 minutes. The solvent was removed to give 6-(3-chloro-phenyl)-4-methyl-1,4-dihydro-benzo[d][1,3]oxazin-2-one as a white solid (0.031 g, 91%): mp 155–156° C.; $^1$H-NMR (DMSO-d$_6$) δ10.3 (s, 1H), 7.72 (m, 1H), 7.62 (m, 2H), 7.56 (m, 1H), 7.47 (t, 1H, J=8.00 Hz), 7.39 (d, 1H, J=8.0 Hz), 6.98 (d, 1H, J=8.0 Hz), 5.50 (q, 1H, J=6.82 Hz), 1.6 (d, 3H, J=6.82 Hz); MS (APCI) m/z 274 ([M+H]$^+$, 100%).

EXAMPLE 10

6-(3-Chloro-phenyl)4-ethyl-1,4-dihydro-benzo[d][1,3]oxazin-2-one

Prepared according to the procedure of Example 9 from 1-(4-amino-3'-chloro-biphenyl-3-yl)-propanol and triphosgene. White solid: mp 146–148° C.; $^1$H-NMR (DMSO-d$_6$) δ10.3 (s, 1H), 7.70 (m, 1H), 7.60 (m, 3H), 7.47 (t, 1H, J=8.22 Hz), 7.39 (d, 1H, J=8.28 Hz), 6.97 (d, 1H, J=8.22 Hz), 5.4 (t, 1H, J=10.9 Hz), 1.9 (m, 2H), 0.97 (t, 3H, J=7.68 Hz); MS (ESI) m/z 286 ([M−H]$^−$, 100%)

EXAMPLE 11

6-(3-Chloro-phenyl)4-phenyl-1,4-dihydro-benzo[d][1,3]oxazin-2-one

Prepared from 1-(4-amino-3'-chloro-biphenyl-3-yl)-benzyl alcohol and triphosgene according to the procedure of Example 9. Off-white solid: mp 177–178° C.; $^1$H-NMR (DMSO-d$_6$) δ10.5 (s, 1H), 7.68 (dd, 1H, J=8.7, 1.7 Hz), 7.62 (t, 1H, J=1.74 Hz), 7.54–7.5 (m, 1H), 7.48–7.34 (m, 8H), 7.04 (d, 1H, J=8.7 Hz), 6.6 (s,1H); MS (ESI) m/z 336 ([M+H]$^+$, 30%).

EXAMPLE 12

3-(4,4-Dimethyl-2-oxo-1,4-dihydro-2H-benzo[d][1,3]oxazin-6-yl)-benzonitrile (Procedure B)

A mixture of (1,4-dihydro4,4-dimethyl-2-oxo-2H-3,1-benzoxazin-6-yl)boronic acid (2.22 g, 10 mmol), 3-bromobenzonitrile (2.18 g, 12 mmol), tetrakis(triphenylphosphine)palladium (0) (0.6 g, 0.52 mmol), and sodium carbonate (2.2 g, 21 mmol) in a mixture of DME and water (70 mL/15 mL) was degassed to remove the oxygen and then heated at 85° C. under a blanket of nitrogen for 3 hours. The reaction mixture was cooled to ambient temperature and quenched with a saturated aqueous ammonium chloride solution (20 mL). Ethyl acetate (100 mL) was added and organic layer was separated. The aqueous layer was extracted with ethyl acetate (3×30 mL). The combined organic layers were washed with brine and dried with $MgSO_4$. The solvent was removed in vacuo and the residue was purified by a silica gel flash chromatography (hexane:ethyl acetate/1;1) to give 3-(4,4-dimethyl-2-oxo-1,4-dihydro-2H-benzo[d][1,3]oxazin-6-yl)-benzonitrile as an off-white solid (0.7 g, 25%): mp 236–237° C.; $^1$H-NMR (DMSO-$d_6$) δ10.34 (s, 1H, $D_2O$ exchangeable), 8.21 (s, 1H), 8.02 (d, 1H, J=8.1 Hz), 7.79 (d, 1H, J=7.7 Hz), 7.60–7.70 (m, 3H), 6.98 (d, 1H, J=8.2 Hz), 1.71 (s, 6H); Anal. Calc. For $C_{17}H_{14}N_2O_2.0.1 H_2O$: C, 72.89, H, 5.11, N, 10.00. Found: C, 72.75, H, 5.05, N, 9.65.

EXAMPLE 13

4,4-Dimethyl-6-(3-nitrophenyl)-1,4-dihydrobenzo[d][1,3]oxazin-2-one

Prepared from 6-iodo4,4-dimethyl-1,4-dihydro-benzo[d][1,3]oxazin-2-one and 3-nitrophenyl boronic acid according to Procedure A. Yellowish solid: mp 244–245° C.; $^1$H-NMR (DMSO-$d_6$) δ10.38 (s, 1H, $D_2O$ exchangeable), 8.47 (s, 1H), 8.14–8.20 (m, 2H), 7.70–7.76 (m, 3H), 7.01 (d, 1H, J=8.1 Hz), 1.68 (s, 6H); MS (EI) m/z 297([M–H]$^{31}$, 100%). Anal. Calc. For $C_{16}H_{14}N_2O_4$: C, 64.42, H, 4.73, N, 9.39. Found: C, 63.93, H, 4.91, N, 8.71.

EXAMPLE 14

6-(3-Bromo-5-fluorophenyl)-4,4-dimethyl-1,4-dihydrobenzo[d][1,3]oxazin-2-one

Prepared from (1,4-dihydro-4,4-dimethyl-2-oxo-2H-3,1-benzoxazin-6-yl)boronic acid and 1,3-dibromo-5-fluorobenzene following Procedure B. White solid: mp 182–183° C.; $^1$H-NMR (DMSO-$d_6$) δ10.36 (s, 1H, $D_2O$ exchangeable), 7.78 (s, 1H), 7.58–7.65 (m, 3H), 7.49 (dd, 1H, J=8.3, 1.8 Hz), 6.96 (d, 1H, J=8.5 Hz), 1.69 (s, 6H); $^{19}$F-NMR (DMSO-$d_6$) δ–112.46 (m, 1F); MS (CI) m/z 352 ([M+H]$^+$, 78%), 350 ([M+H]$^+$, 75%). Anal. Calc. For $C_{16}H_{13}BrFNO_2$: C, 54.88, H, 3.74, N, 4.00. Found: C, 54.83, H, 3.82, N, 3.95.

EXAMPLE 15

3-(4,4-Dimethyl-2-oxo-1,4-dihydro-2H-benzo[d][1,3]oxazin-6-yl)-5-fluorobenzonitrile A mixture of 6-(3-bromo-5-fluorophenyl)4,4-dimethyl-2H-benz[d][1,3]oxazin-2-one (1 g, 2.8 mmol), zinc cyanide (0.2 g, 1.7 mmol), and tetrakis(triphenylphosphine)-palladium (0) (0.2 g, 0.17 mmol) in dry DMF (20 mL) was degassed to remove oxygen and then was heated at 85° C. under a blanket of nitrogen for 6.5 hours. The reaction solution was cooled to room temperature and poured onto a cold saturated aqueous ammonium chloride solution (100 mL). The white precipitate appeared and was collected on a filter. The white solid was washed with the distilled water (3×20 mL) and dissolved in a mixture of ethyl acetate (10 mL) and methanol (10 mL). The solution was applied on a pad of silica gel and eluted with a mixture of ethyl acetate and hexane (1:1). After evaporation, 3-(4,4-dimethyl-2-oxo-1,4-dihydro-2H-benzo[d][1,3]oxazin-6-yl)-5-fluorobenzonitrile was obtained as a white solid (0.7 g, 84%): mp 253–254° C.; $^1$H-NMR (DMSO-$d_6$) δ10.4 (s, 1H, $D_2O$ exchangeable), 8.13 (s, 1H), 7.92 (m, 1H), 7.82 (m, 1H), 7.73 (m, 2H), 6.98 (d, 1H, J=8.2 Hz), 1.68 (s, 6H); $^{19}$F-NMR (DMSO-$d_6$) δ–112.25 (m, 1F); MS (EI) m/z 296 (M$^+$, 65%); Anal. Calc. For $C_{17}H_{13}FN_2O_2$: C, 68.91, H, 4.42, N, 9.45. Found: C, 68.85, H, 4.58, N, 9.14.

EXAMPLE 16

5-(4,4-Dimethyl-2-oxo-1,4-dihydro-2H-benzo[d][1,3]oxazin-6-yl)-nicotinonitrile

Prepared from (1,4-dihydro-4,4-dimethyl-2-oxo-2H-3,1-benzoxazin-6-yl) boronic acid and 3-bromo-5-cyanopyridine according to Procedure B. Off-white solid: mp 290–291° C.; $^1$H-NMR (DMSO-$d_6$) δ10.41 (s, 1H, $D_2O$ exchangeable), 9.21 (d, 1H, J=2.2 Hz), 8.97 (d, 1H, J=1.7 Hz), 8.68 (t, 1H, J=2.1 Hz), 7.76 (m, 2H), 7.01 (d, 1H, J=8.2 Hz), 1.70 (s, 6H); MS (ESI) m/z 278(M–H, 96%). Anal. Calc. For $C_{16}H_{13}N_3O_2.0.2 H_2O$: C, 67.94, H, 4.77, N, 14.85. Found: C, 68.04, H, 4.70, N, 14.58.

EXAMPLE 17

4-(4,4-Dimethyl-2-oxo-1,4-dihydro-2H-benzo[d][1,3]oxazin-6-yl)-thiophene-2-carbonitrile Prepared from (1,4-dihydro-4,4-dimethyl-2-oxo-2H-3,1-benzoxazin-6-yl)boronic acid and 4-bromo-2-thiophenecarbonitrile according to Procedure B. Yellowish solid: mp 230–231° C. (decomposed); $^1$H-NMR (CDCl$_3$) δ8.32 (s, 1H, $D_2O$ exchangeable), 7.83 (d, 1H, J=1.5 Hz), 7.61 (d, 1H, J=1.4 Hz), 7.43 (dd, 1H, J=8.2, 1.9 Hz), 7.29 (d, 1H, J=1.8 Hz), 6.85 (d, 1H, J'8.2 Hz), 1.78 (s, 6H); MS (EI) m/z 283(M–H, 100%). Anal. Calc. For $C_{15}H_{12}N_2O_2S.0.2 H_2O$: C, 62.57, H, 4.34, N, 9.73. Found: C, 62.48, H, 4.31, N, 9.64.

EXAMPLE 18

5-Bromo-2-thiophenecarbonitrile

A mixture of 5-bromo-2-thiophenecarboxaldehyde (96.0 g, 500 mmol), hydroxylamine hydrochloride (11.9 g, 500 mmol), pyridine (500 mL), and ethanol (500 mL) was heated under nitrogen at reflux for two hours. The reaction mixture was cooled to ambient temperature and concentrated in vacuo to give an oil. The crude product was triturated twice with ice water and the solid obtained was collected on a filter. A mixture of a portion of the above solid (44.31 g, 215 mmol), copper (II) acetate monohydrate (4.2 g, 21 mmol) in acetonitrile (1.4L) was heated at reflux for three hours. The solvent was removed in vacuo and the residue was dissolved in ethyl acetate. The solution was washed with 5% aqueous sulfuric acid (2×30 mL), water (2×30 mL), brine (20 mL), and dried (MgSO$_4$). The solvent was removed in vacuo and the residue was dissolved in a minimum amount of chloroform (1L) and allowed to crystallize. The crystal obtained was collected on a filter and the filtrate was concentrated and purified by a chromatography (silica gel, chloroform) to give the title compound as an off-white solid (31.5 g combined, 58%). IR (film) cm$^{-1}$ 2200. $^1$H-NMR (CDCl$_3$) δ7.39–7.38 (d, 1H, J=4.1 Hz), 7.10 (d, 1H, J=4.0 Hz); MS (EI) m/z 187 (M$^+$, 98%) 189(M$^+$, 100%).

EXAMPLE 19

5-Bromo-4-methyl-2-thiophene carboxaldehyde

To a solution of diethylamine (28 g, 0.383 mol) in anhydrous THF (400 mL) was added a solution of n-BuLi (2.5 M, 153 mL, 0.383 mol) in hexane. The solution was then stirred at −40° C. under nitrogen for 30 minutes, cooled to −78° C. and treated dropwise with a solution of 2-bromo-3-methylthiophene (45 g, 0.254 mol) in anhydrous THF (450 mL). The reaction solution was stirred at −78° C. for 30 minutes and treated with anhydrous DMF (100 mL). The mixture was allowed to warm to ambient temperature and was quenched with 1N aqueous hydrochloride solution (1L). The product was extracted with ethyl acetate (3×450 mL). The extracts were washed with water, brine and dried ($MgSO_4$). After removal of solvent in vacuo, the title compound was obtained as a white solid (46 g, 88.3%). A sample of the product was crystallized from hexane: mp 63–65° C.; IR (KBr) 1654 $cm^{-1}$. $^1$H-NMR ($CDCl_3$) δ9.75 (S, 1H), 7.45 (S, 1H), 2.26 (S, 3H); MS (EI) m/z 204/206 ($M^+$). Anal. Calc. For $C_6H_5BrOS$: C, 35.14; H, 2.46. Found: C, 35.00; H, 2.44.

EXAMPLE 20

5-Bromo-4-methyl-2-thiophenecarbonitrile

Prepared from 5-bromo-4-methyl-2-thiophene carboxaldehyde using the procedure of Example 18. White solid: mp 40–42° C.; IR (KBr) 2200 $cm^-$; $^1$H-NMR ($CDCl_3$) δ7.29 (S, 1H), 2.21 (S, 3H). MS (EI) m/z 201/203 ($M^+$, 98%/100%); Anal. Calc. For $C_6H_4BrNS$: C, 35.66; H, 1.99; N, 6.93. Found: C, 36.00; H, 2.14; N, 6.76.

EXAMPLE 21

5-(4,4-Dimethyl-2-oxo-1,4-dihydro-2H-benzo[d][1,3]oxazin-6-yl)-thiophene-2-carbonitrile Prepared according to Procedure B from 5-bromo-2-thiophenecarbonitrile and (1,4-dihydro-4,4-dimethyl-2-oxo-2H-3,1-benzoxazin-6-yl)boronic acid. Off-white solid: mp 264–266° C. $^1$H-NMR (DMSO-$d_6$) δ10.3 (s, 1H), 7.97 (d, 1H, J=7.9 Hz), 7.60–7.66 (m, 3H). 6.96 (d, 1H, J=8.1 Hz), 1.65 (S, 6H). MS (APCI) m/z 285 $(M+H)^+$, 302 $(M+NH_4)^+$. Anal. Calc. For $C_{15}H_{12}N_2O_2S$: C, 63.36; H, 4.25; N, 9.85. Found: C, 63.01; H, 4.36; N, 9.39.

EXAMPLE 22

5-(4, 4-Dimethyl-2-oxo-1,4-dihydro-2H-benzo[d][1,3]oxazin-6-yl)-4-methyl-thiophene2-carbonitrile Prepared according to Procedure B from (1,4-dihydro-4,4-dimethyl-2-oxo-2H-3,1-benzoxazin-6-yl)boronic acid and 5-bromo-4-methyl-2-thiophenecarbonitrile. Off-white solid: mp 195–200° C. $^1$H-NMR (DMSO-$d_6$) δ10.2 (s, 1H), 8.32 (s, 1H), 7.41–7.44 (m, 2H), 7.01 (d, 1H, J=8.8 Hz), 2.28 (S, 3H), 1.64 (S, 6H); MS (APCI) m/z 299 $[M+H]^+$. Anal. Calc. For $C_{16}H_{14}N_2O_2S$; C, 64.41; H, 4.75; N, 8.89. Found: C, 64.64; H, 4.62; N, 9.39.

EXAMPLE 23

4-(4,4-Dimethyl-2-oxo-1,4-dihydro-2H-benzo[d][1,3]oxazin-6-yl)-furan-2-carbonitrile Prepared from (1,4-dihydro-4,4-dimethyl-2-oxo-2H-3,1-benzoxazin-6-yl)boronic acid and 4-bromo-2-furancarbonitrile according to Procedure B. Off-white solid: mp 255–256° C. $^1$H-NMR (DMSO-$d_6$) δ10.32 (s, 1H, $D_2O$ exchangeable), 8.57 (s, 1H), 8.15 (s, 1H), 7.61 (s, 1H), 7.55 (dd, 1H, J=8.3, 1.5 Hz), 6.92 (d, 1H, J=8.2 Hz), 1.65 (s, 6H); MS (ESI) m/z 269(M+H, 72%). Anal. Calc. For $C_{15}H_{12}N_2O_3$: C, 67.16, H, 4.51, N, 10.44. Found: C, 67.14, H, 4.59, N, 10.07.

EXAMPLE 24

4,4-Diethyl-6-(3-nitrophenyl)-1,4-dihydrobenzo[d][1,3]oxazin-2-one

Prepared from 4,4-diethyl-6-iodo-1,4-dihydrobenzo[d][1,3]oxazin-2-one and 3-nitrophenyl boronic acid according to Procedure A. Off-white solid: mp 193–194 ° C. $^1$H-NMR ($CDCl_3$) δ9.19 (s, 1H, $D_2O$ exchangeable), 8.38 (t, 1H, J=1.9 Hz), 8.20 (m, 1H), 7.83 (m, 1H), 7.61 (t, 1H, J=8.0 Hz), 7.50 (dd, 1H, J=8.2, 2.0 Hz), 7.23 (d, 1H, J=1.7 Hz), 6.99 (d, 1H, J=8.3 Hz), 2.09 (q, 4H, J=7.4 Hz), 0.96 (t, 6H, J=8.3 Hz); MS (EI) m/z 325 ($[M-H]^-$, 100%). Anal. Calc. For $C_{18}H_{18}N_2O_4 \cdot 0.3 H_2O$: C, 65.17, H, 5.65, N, 8.44. Found: C, 65.31, H, 5.60, N, 8.10.

EXAMPLE 25

6-(3-Chlorophenyl)4,4-diethyl-1,4-dihydrobenzo[d][1,3]oxazin-2-one

Prepared from 4,4-diethyl-6-iodo-1,4-dihydrobenzo[d][1,3]oxazin-2-one and 3-chlorophenyl boronic acid according to Procedure A. White solid: mp 150–151° C. $^1$H-NMR ($CDCl_3$) δ8.52 (s, 1H, $D_2O$ exchangeable), 7.50 (s, 1H), 7.31–7.44 (m, 4H) 7.16 (d, 1H, J=1.5 Hz), 6.89 (d, 1H, J=8.2 Hz), 2.03 (m, 4H), 0.94 (t, 6H, J=7.4 Hz); MS (EI) m/z 315($M^+$, 53%). Anal. Calc. For $C_{18}H_{18}ClNO_2$: C, 68.46, H, 5.75, N, 4.44. Found: C, 68.16, H, 5.81, N, 4.32.

EXAMPLE 26

1-(2-Amino-5-bromo-phenyl) cyclohexanol

Prepared according to the procedure of Example 1 from 2-amino-5-bromobenzoic acid and the Grignard reagent prepared from 1,5-dibromopentane. A clear oil: $^1$H-NMR (DMSO-$d_6$) δ7.07 (d, 1H, J=2.3 Hz), 7.03 (dd, 1H, J=8.4, 2.4 Hz), 6.55 (d, 1H, J=8.6 Hz), 5.49 (s, 2H, $D_2O$ exchangeable), 5.00 (s, 1H, $D_2O$ exchangeable), 2.01 (d, 2H, J=1.8 Hz), 1.66–1.77 (m, 2H), 1.44–1.61 (m, 4H), 1.16–1.34 (m, 2H). MS (ESI) m/z 270/272 ($[M+H]^+$, 98%/100%).

EXAMPLE 27

6-Bromo-spiro[4H-3,1-benzoxazine-4,1'-cyclohexane-2-(1H)-one

Prepared from 1-(2-amino-5-bromo-phenyl) cyclohexanol and carbonyl diimidazole according to the procedure of Example 2. Off-white solid: mp 208–210° C. $^1$H-NMR (DMSO-$d_6$) δ10.26 (s, 1H), 7.45 (d, 1H, J=2.2 Hz), 7.39 (dd, 1H, J=8.2, 2.2 Hz), 6.81 (d, 1H, J=8.3 Hz), 1.90–1.97 (m, 2H), 1.80–1.85 (m, 5H), 1.25–1.35 (m, 1H); MS (APC1) m/z 296 ($[M+H]^+$, 68%)

EXAMPLE 28

Spiro-(4,1'-cyclohexane-1,4-dihydro-2-oxo-2H-3,1-benzoxazin-6-yl) boronic acid Prepared according to the procedure of Example 4 from 6-bromo-spiro[4H-3, 1-benzoxazine-4,1'-cyclohexane-2-(1H)-one. Off-white solid: mp 223–225° C. $^1$H-NMR (DMSO-$d_6$) δ10.17 (s, 1H, $D_2O$ exchangeable), 7.92 (s, 2H, $D_2O$ exchangeable), 7.67 (S, 1H), 7.63 (dd, 1H, J=8.0, 1.1 Hz), 6.81 (d, 1H, J=7.9 Hz), 1.96(s, 1H), 1.93 (s, 1H), 1.57–1.88 (m, 7H), 1.24–1.34 (m, 2H); MS (ESI) m/z 262 $(M+H)^+$.

EXAMPLE 29

6-(3-Chlorophenyl)-spiro[4H-3,1-benzoxazine-4,1'-cyclohexane-2-(1H)-one

Prepared according to Procedure A from 6-bromo-spiro [4H-3,1-benzoxazine-4,1'-cyclohexane]-2(1H)-one and 3-chlorophenyl boronic acid. Off-white solid: mp 165–168° C. $^1$H-NMR (DMSO-d$_6$) δ10.25 (S, 1H), 7.74 (t, 1H, J=1.9 Hz), 7.50–7.67 (m, 3H), 7.42–7.49 (m, 1H), 7.35–7.38 (m 1H), 6.93–6.95 (d, 1H, J=4.2 Hz), 1.91–1.98 (m, 4H), 1.64–1.76 (m, 3H), 1.60 (m, 2H), 1.29–1.39 (m, 1H); MS (APCI) m/z 328 ([M+H]$^+$, 80%)

EXAMPLE 30

6-Bromo-spiro-[4H-3, 1-benzoxazine-4,1'-cyclopentane-2-(1H)-one

Prepared according to the procedure of Example 26 and 27 from 2-amino-5-bromobenzoic acid and the Grignard reagent prepared from 1,4-dibromobutane. Off-white solid: mp 180–185° C. $^1$H-NMR (DMSO-d$_6$) δ10.29 (s, 1H, D$_2$O exchangeable), 7.45 (d, 1H, J=2.2 Hz), 7.41 (dd, 1H, J=8.1, 2.1 Hz), 6.82 (d, 1H, J=8.0 Hz), 1.96–2.09 (m, 4H), 1.76–1.87 (m, 4H); MS (EI) m/z 281 (M$^+$, 98%). Anal. Calc. For C$_{12}$H$_{12}$BrNO$_2$: C 51.08; H, 4.29; N, 4.96. Found: C, 50.53; H, 4.21; N, 4.85

EXAMPLE 31

6-(3-Chlorophenyl)-spiro-[4H-3, 1-benzoxazine4,1'-cyclopentane]-2(1H)-one

Prepared from 6-bromo-spiro-[4H-3, 1-benzoxazine-4,1'-cyclopentane-2-(1H)-one and 3-chlorophenyl boronic acid according to Procedure A. Off-white solid: mp 140–145° C. $^1$H-NMR (DMSO-d$_6$) δ10.27 (s, 1H), 7.75 (t, 1H, J=1.8 Hz), 7.53–7.63 (m, 3H), 7.44 (t, 1H, J=7.9 Hz), 7.36 (m, 1H), 6.95 (d, 1H, J =8.6 Hz), 2.09–2.15 (m, 4H), 1.81–1.89 (m, 4H). MS (ESI) m/z 314 [M+H]$^+$. Anal. Calc. For C$_{18}$H$_{16}$ClNO$_2$: C, 68.90; H, 5.14; N, 4.46. Found: C,60.94; H, 4.94; N, 3.78.

EXAMPLE 32

6-(3-Nitrophenyl)-spiro [4H-3,1-benzoxazine-4,1'-cyclohexan]-2(1H)-one

Prepared from 6-bromo-spiro[4H-3,1-benzoxazine-4,1'-cyclohexane]-2(1H)-one and 3-nitrophenyl boronic acid according to Procedure A. Off-white solid: mp 245–246° C. $^1$H-NMR (CDCl$_3$) δ8.39 (t, 1H, J=1.9 Hz), 8.20 (dd, 1H, J=8.2, 1.4 Hz), 8.11 (s, 1H, D$_2$O exchangeable), 7.86 (d, 1H, J=8.0 Hz), 7.62 (t, 1H, J=8.1 Hz), 7.50 (dd, 1H, J=8.2, 1.9 Hz), 7.39 (d, 1H, J=1.8 Hz), 6.93 (d, 1H, J=8.2 Hz), 2.25 (d, 2H, J=12.7 Hz), 1.60–1.99 (m, 7H), 1.31–1.42 (m, 1H); MS (EI) m/z 337 ([M–H]$^-$, 100%). Anal. Calc. For C$_{19}$H$_{18}$N$_2$O$_4$.0.35H$_2$O: C, 66.21, H, 5.47, N, 8.13. Found: C, 66.22, H, 5.43, N, 7.86.

EXAMPLE 33

2-Amino-5-bromo-N-methoxy-N-methylbenzamide

To a mixture of N, O-dimethylhydroxylamine hydrochloride (9.42 g, 96 mmol) and triethyl amine (13.5 mL, 96 mmol) in ethanol and water (100 mL/10 mL) was added a solution of 5-bromoisatoic anhydride (20 g, 74 mmol) in ethanol and water (100 mL/10 mL) at ambient temperature under nitrogen. The reaction mixture was heated at reflux for 3 hours. The solvent was removed in vacuo and the residue was dissolved in ethyl acetate (100 mL), washed with 1N aqueous sodium hydroxide solution (2×20 mL), brine (30 mL), and dried with MgSO$_4$. After removal of the solvent, the residue was purified by a silica gel flash chromatography (hexane:ethyl acetate/3:2) to give 2-amino-5-bromo-N-methoxy-N-methylbenzamide as an off-white solid (13 g, 68%): mp 80–81° C.; $^1$H-NMR (CDCl$_3$) δ7.49 (d, 1H, J=2.1 Hz), 7.26 (dd, 1H, J=8.3, 2.0 Hz), 6.59 (d, 1H, J=8.4 Hz), 4.69 (br, 2H), 3.58 (s, 3H), 3.34 (s, 3H); Anal. Calc. For C$_9$H$_{11}$BrN$_2$O$_2$: C, 41.72, H, 4.28, N, 10.81. Found: C, 41.99, H, 4.16, N, 10.82.

EXAMPLE 34

4-Amino-3'-chloro-biphenyl-3-carbonitrile

Prepared from 2-amino-5-bromobenzonitrile and 3-chlorophenyl boronic acid according to procedure A. Off-white solid: mp 118–119° C.; $^1$H-NMR (DMSO-d$_6$) δ7.80 (d, 1H, J=2.3 Hz), 7.65–7.72 (m, 2H), 7.57 (d, 1H, J=8.0 Hz), 7.42 (t, 1H, J=7.9 Hz), 7.31 (m, 1H), 6.87 (d, 1H, J=8.7 Hz), 6.29 (br, 2H); Anal. Calc. For C$_{13}$H$_9$ClN$_2$: C, 68.28, H, 3.97, N, 12.25. Found: C, 67.68, H, 4.06, N, 11.89.

EXAMPLE 35

1-(4-Amino-3'-chloro-biphenyl-3-yl)-ethanone

A mixture of 2-amino-5-bromo-N-methoxy-N-methylbenzamide (7.78 g, 30 mmol), 3-chlorophenyl boronic acid (5.63 g, 36 mmol), tetrakis(triphenylphosphine) palladium (0) (1.73 g, 1.5 mmol), and sodium carbonate (7.63 g, 72 mmol) in a mixture of DME and water (150 mL/30 mL) was degassed to remove the oxygen and heated at 85° C. under nitrogen for 3 hours. The reaction mixture was cooled to room temperature and treated with brine (30 mL) and ethyl acetate (100 mL). The organic layer was separated and aqueous layer was extracted with ethyl acetate (3×40 mL). The combined organic layers were washed with brine and dried with MgSO$_4$. After removal of solvent, the residue was purified by a flash chromatography (silica gel, hexane:ethyl acetate/1:1) to give 5-(3-chlorophenyl)-N-methoxy-N-methylbenzamide as a brown oil (5 g, 57%). To a solution of this benzamide (5 g, 17.2 mmol) in anhydrous THF was added in a dropwise fashion a solution of methyllithium in ether (1.4M, 28.6 mL, 40 mL) at –78° C. under nitrogen. After stirring for 30 minutes, the reaction mixture was treated with a saturated aqueous ammonium chloride solution (50 mL) at –78° C. Ethyl acetate (100 mL) was added, organic layer was separated, and aqueous layer was extracted with ethyl acetate (3×20 mL). The combined organic layers were washed (brine) and dried (MgSO$_4$). After removal of solvent, the residue was purified by a flash chromatography (silica gel, hexane:ethyl acetate/2:1) to afford 1-(4-amino-3'-chloro-biphenyl-3-yl)-ethanone as a yellow solid (2 g, 47%): mp 89–90° C.; $^1$H-NMR (CDCl$_3$) δ7.89 (d, 1H, J=2.0 Hz), 7.51 (m, 2H), 7.25–7.40 (m, 3H), 6.73 (d, 1H, J=8.6 Hz), 6.38 (br, 2H), 2.65 (s, 3H); MS (EI) m/z 268([M+Na]$^+$, 60%); Anal. Calc. For C$_{14}$H$_{12}$ClNO: C, 68.44, H, 4.92, N, 5.70. Found: C, 68.40, H, 4.89, N, 5.61.

EXAMPLE 36

4-Allyl-6-(3-chlorophenyl)-4-methyl-1,4-dihydro-benzo[d][1,3]oxazin-2-one (Procedure C)

To a solution of 1-(4-amino-3'-chloro-biphenyl-3-yl)-ethanone (0.2 g, 0.82 mmol) in anhydrous THF (10 mL) was added a solution of allylmagnesium bromide in ether (1.0 M, 3 mL, 3 mmol) at 0° C. under nitrogen. The reaction solution was slowly warmed to ambient temperature and stirred under nitrogen for 1 hour. A saturated aqueous ammonium chloride solution (10 mL) was added, followed by addition of ethyl acetate (50 mL). The organic layer was separated and aqueous layer was extracted with ethyl acetate (3×10 mL). The combined organic layers were washed with brine and dried with $MgSO_4$. After removal of solvent, the residue was purified by flash chromatography (silica gel, hexane-:ethyl acetate/3:1) to afford an amino carbinol intermediate which was used without further purification.

To a solution of above amino carbinol in anhydrous THF was added CDI (0.38 g, 2.3 mmol) at ambient temperature under nitrogen. The reaction solution was heated at 55° C. for 12 hours and then cooled to room temperature. The solvent was removed in vacuo and the residue was purified by flash chromatography (silica gel, hexane:ethyl acetate/2:1) to yield 4-allyl-6-(3-chlorophenyl)-4-methyl-1,4-dihydro-benzo[d][1,3]oxazin-2-one as a white solid (130 mg from two steps, 52%): mp 128–129° C.; $^1$H-NMR ($CDCl_3$) δ8.68 (s, 1H, $D_2O$ exchangeable), 7.50 (s, 1H), 7.44 (dd, 1H, =8.2, 1.9 Hz), 7.31–7.40 (m, 3H), 7.25 (d, 1H, J=1.6 Hz), 6.92 (d, 1H, J=8.2 Hz), 5.70–5.85 (m, 1H), 5.17 (m, 2H), 2.76 (m, 2H), 1.79 (s, 3H); MS (ESI) m/z 314 ([M+H]$^+$, 40%); Anal. Calc. For $C_{18}H_{16}ClNO_2$: C, 68.90, H, 5.14, N, 4.46. Found: C, 68.90, H, 5.18, N, 4.43.

EXAMPLE 37

6-(3-Chlorophenyl)-4-methyl-4-propyn-1-yl-1,4-dihydro-benzo[d][1,3]oxazin-2-one

Prepared from 1-(4-amino-3'-chloro-biphenyl-3-yl)-ethanone and propynyl-magnesium bromide followed by treatment with CDI according to Procedure C. White solid: mp 184–185° C.; $^1$H-NMR ($CDCl_3$) δ8.18 (s, 1H, $D_2O$ exchangeable), 7.53 (t, 1H, J=1.7 Hz), 7.49 (s, 1H), 7.31–7.48 (m, 4H), 6.92 (d, 1H, J=8.1 Hz), 2.02 (s, 3H), 1.87 (s, 3H); MS (ESI) m/z 304([M–H]$^-$, 100%); Anal. Calc. For $C_{18}H_{14}ClNO_2$: C, 69.35, H, 4.53, N, 4.49. Found: C, 69.19, H, 4.37, N, 4.41.

EXAMPLE 38

6-(3-Chlorophenyl)-4-ethynyl-4-methyl-1,4-dihydro-benzo[d][1,3]oxazin-2-one

Prepared from 1-(4-amino-3'-chloro-biphenyl-3-yl)-ethanone (0.2 g, 0.82 mmol) and ethynylmagnesium bromide followed by treatment with CDI according to procedure C. Off-white solid: mp 185–186° C.; $^1$H-NMR ($CDCl_3$) δ8.18 (s, 1H, $D_2O$ exchangeable), 7.53 (t, 1H, J=1.7 Hz), 7.49 (s, 1H), 7.31–7.48 (m, 4H), 6.92 (d, 1H, J=8.1 Hz), 2.81 (s, 1H), 1.87 (s, 3H); MS (ESI) m/z 304 ([M–H]$^-$, 100%); Anal. Calc. For $C_{17}H_{12}ClNO_2$: C, 68.58, H, 4.06, N, 4.70. Found: C, 68.24, H, 3.94, N, 4.65.

EXAMPLE 39

6-(3-Chlorophenyl)-4-methyl4-phenyl-1,4-dihydro-benzo[d][11,3]oxazin-2-one

Prepared from 1-(4-amino-3'-chloro-biphenyl-3-yl)-ethanone (0.2 g, 0.82 mmol) and phenylmagnesium bromide followed by treatment with CDI according to Procedure C. White solid: mp 179–180° C.; $^1$H-NMR ($CDCl_3$) δ8.27 (s, 1H, $D_2O$ exchangeable), 7.51–7.57 (m, 2H), 7.28–7.45 (m, 9H), 6.92 (d, 1H, J=8.4 Hz), 2.12 (s, 3H); MS (ESI) m/z 348 ([M–H]$^-$, 100%); Anal. Calc. For $C_{21}H_{16}ClNO_2$: C, 72.10, H, 4.61, N, 4.00. Found: C, 71.72, H, 4.86, N, 3.91.

EXAMPLE 40

4-Benzyl-6-(3-chloro-phenyl)4-methyl-1,4-dihydro-benzo[d][1,3]oxazin-2-one

A mixture of 1-(4-amino-3'-chloro-biphenyl-3-yl)-1-benzyl-ethanol (prepared using 1-(4-amino-3'-chloro-biphenyl-3-yl)-ethanone and benzylmagnesium bromide according to Procedure C, 0.14 g, 0.42 mmol) and triphosgene (0.04 g, 0.14 mmol) in dry THF (10 mL) was stirred under a blanket of nitrogen for 10 minutes. Upon completion of the reaction, the THF was removed and the residue purified via flash chromatography (silica gel, 35% ethyl acetate/hexane) to give 4-benzyl-6-(3-chloro-phenyl)-4-methyl-1,4-dihydro-benzo[d][1,3]oxazin-2-one (0.045 g, 30%) as an off-white solid: mp 187–188° C.; $^1$H-NMR (DMSO-$d_6$) δ10.1 (s, 1H), 7.70 (t, 1H, J=2.3 Hz), 7.6 (d, 1H, J=8.0 Hz), 7.58–7.53 (m, 2H), 7.46 (t, 1H, J=8.0 Hz), 7.38 (d, 1H, J=8.0 Hz), 7.22–7.17 (m, 3H), 7.06–7.0 (m, 2H), 6.84 (d, 1H, J=9.14 Hz), 3.24 (d, 1H, J=14.3 Hz), 3.06 (d, 1H, J=14.3 Hz), 1.68 (s, 3H); MS (ESI) m/z 364 ([M+H]$^+$, 100%); Anal. Calc. For $C_{22}H_{18}ClNO_2$: C,72.63; H, 4.99; N, 3.85. Found: C, 71.82; H,5.09; N,3.58.

EXAMPLE 41

6-(3-Chloro-phenyl)-4-cyclopropyl-4-methyl-1,4-dihydro-benzo[d][1,3]oxazin-2-one To a solution of cyclopropylmagnesium bromide in anhydrous THF (prepared using cyclopropyl bromide and magnesium metal, 70 mmol) at 52° C. was added under nitrogen 4-amino-3'-chloro-biphenyl-3-carbonitrile (5.2 g, 22.7 mmol). The reaction mixture was stirred at 52° C. for 1 hour, cooled to rt, and quenched with 1N aqueous HCl solution (100 mL). Ethyl acetate (100 mL) was added and the aqueous layer was extracted with ethyl acetate (3×40 mL). The combined organic layers were washed with brine and dried over $MgSO_4$. The solvent was removed and the residue was purified via silica gel column (hexane:ethyl acetate/20:1) to give the (4-amino-3'-chloro-biphenyl-3-yl)-cyclopropyl-methanone: $^1$H-NMR (hydrogen chloride salt, DMSO-$d_6$) δ8.30 (d, 1H, J=2.1 Hz), 7.76 (t, 1H, J=1.7 Hz), 7.68–7.63 (m, 2H), 7.43 (t, 1H, J=7.9 Hz), 7.32 (m, 1H), 6.88 (d, 1H, J=8.7 Hz), 4.50 (bs, 3H), 3.07 (m, 1H), 0.98 (m, 4H); (MS ((+)ESI) m/z 272/274 (M$^+$).

To a solution of (4-amino-3'-chloro-biphenyl-3-yl)-cyclopropyl-methanone (0.67 g, 2.5 mmol) in anhydrous THF (10 mL) at −78° C. was added a solution of methylmagnesium bromide (3.0 M in diethyl ether, 2.5 mL, 7.5 mmol) under nitrogen. The reaction mixture was slowly warmed to rt, stirred under nitrogen for 12 hours, and quenched with a saturated aqueous ammonium chloride solution (40 mL). Ethyl acetate (50 mL) was added, the organic layer was separated, and dried ($MgSO_4$). After removal of the solvent, the residue was purified via silica gel chromatography (hexane:ethyl acetate/7: 1) to afford 1-(4-amino-3'-chloro-biphenyl-3-yl)-1-cyclopropyl-ethanol as yellow oil: MS (EI) m/z 287/289 (M$^+$).

The title compound was prepared from 1-(4-amino-3'-chloro-biphenyl-3-yl)-1-cyclopropyl-ethanol and 1,1'carbonyldiimidazole according to Procedure C. Off-white solid: mp 158–159° C.; $^1$H-NMR (DMSO-d6) δ10.3 (s, 1H), 7.74 (t, 1H, J=1.71 Hz), 7.67–7.57 (m, 3H), 7.47 (t, 1H, J=7.88 Hz), 7.39 (d, 1H, J=8.1 Hz), 6.95 (d, 1H, J=8.12 Hz), 1.7 (s, 3H), 1.45 (m, 1H), 0.48 (m, 2H), 0.28 (m, 2H); MS (APCI) m/z 314 ([M+H]$^+$, 100%); Anal. Calc. For $C_{18}H_{16}ClNO_2$: C, 68.9; H, 5.14; N, 4.46. Found: C, 68.13; H, 5.01; N, 4.36.

EXAMPLE 42

6-(3-Chloro-phenyl)-4-cyclopropyl-4-propyn-1-yl-1,4-dihydro-benzo[d][1,3]oxazin-2-one 1-(4-Amino-3'-chloro-biphenyl-3-yl)-1-cyclopropyl-1-propynyl-methanol was prepared from (4-amino-3'-chlorobiphenyl-3-yl)-cyclopropyl-methanone and propynylmagnesium bromide according to Example 41.

A mixture of 1-(4-amino-3'-chloro-biphenyl-3-yl)-1-cyclopropyl-1-propynyl-methanol (0.02 g, 0.064 mmol) and 1,1'-carbonyldiimidazole (0.016 g, 0.096 mmol) in dry THF (10 mL) was stirred under a blanket of nitrogen for 10 minutes. Upon completion of the reaction, the THF was removed and the residue purified via flash chromatography (silica gel, 40% ethyl acetate/hexane) to give 6-(3-chlorophenyl)-4-cyclopropyl-4-prop-1-ynyl-1,4-dihydro-benzo[d][1,3]oxazin-2-one (0.014 g, 56%) as a light yellow solid: mp 178–179° C.; $^1$H-NMR (DMSO-d$_6$) δ10.6 (s, 1H), 7.68 (m, 2H), 7.64 (bs, 1H), 7.59 (d, 1H, J=7.72 Hz), 7.49 (t, 1H, J=7.82 Hz), 7.42 (d, 1H, J=7.95 Hz), 7.02 (d, 1H, J=8.0 Hz), 1.86 (s, 3H), 1.66 (m, 1H), 0.82 (m, 1H), 0.66 (m, 3H); MS (ESI) m/z 336 ([M–H]$^-$, 100%).

EXAMPLE 43

6-(3-Chloro-phenyl)4,4-dicyclopropyl-1,4-dihydro-benzo[d][1,3]oxazin-2-one (4-Amino-3'-chloro-biphenyl-3-yl)-dicylopropyl-methanol (mp 90–92° C.; MS ((+)ESI) m/z 314 (M+H)$^+$.) was prepared from (4-amino-3'-chloro-biphenyl-3-yl)-cyclopropyl-methanone and cyclopropylmagnesium bromide according to Example 41.

The title compound was prepared according to Example 41 from (4-amino-3'-chloro-biphenyl-3-yl)-dicylopropyl-methanol and 1,1'-carbonyldiimidazole. Yellow solid: mp 198–200° C.; $^1$H-NMR (DMSO-d$_6$) δ10.3 (s, 1H), 7.72 (bs, 1H), 7.67 (bs, 1H), 7.62 (m, 2H), 7.48 (t, 1H, J=7.88 Hz), 7.40 (d, 1H, J=8.04 Hz), 6.94 (d, 1H, J=8.27 Hz), 1.55 (m, 2H), 0.5 (m, 6H), 0.28 (m, 2H); MS (EI) m/z 339 (M$^+$, 40%); Anal. Calc. For C$_{20}$H$_{18}$ClNO$_2$: C, 70.69; H, 5.34 N, 4.12. Found: C, 69.38; H, 5.07; N, 4.02.

EXAMPLE 44

6-(3-Chloro-phenyl)-4,4-dipropyn-1-yl-1,4-dihydrobenzo[d][1,3]oxazin-2-one

Following the procedure of Example 41, (4-amino-3'-chloro-biphenyl-3-yl)-propynyl-methanone (mp 112–114° C.; MS ((+) ESI) m/z 270/272 (M+H)$^+$) was treated with propynylmagnesium bromide to give (4-amino-3'-chloro-biphenyl-3-yl)-dipropynyl-methanol which was reacted with 1,1'-carbonyldiimidazole to afford the title compound. Yellow solid: mp 151° C. (decomposed); $^1$H-NMR (DMSO-d$_6$) δ10.8 (s, 1H), 7.71 (dd, 1H, J=8.52,1.94 Hz), 7.69 (m, 2H), 7.61 (d, 1H, J=7.64 Hz), 7.50 (t, 1H, J=7.85 Hz), 7.43 (d, 1H, J=7.99 Hz), 7.06 (d, 1H, J=8.23 Hz), 2.0 (s, 6H); MS (APCI) m/z 336 ([M+H]$^+$, 20%).

EXAMPLE 45

6-(3-Bromo-5-fluorophenyl)-1,4,4-trimethyl-1,4-dihydrobenzo[d][1,3]oxazin-2-one

To a solution of 6-(3-bromo-5-fluorophenyl)-4,4-dimethyl-1,4-dihydrobenzo[d][1,3]oxazin-2-one (0.34 g, 0.99 mmol) in dry DMF (10 mL) was added under nitrogen at room temperature sodium hydride (80 mg, 2.0 mmol) in one portion. The mixture was stirred at ambient temperature for 30 minutes, treated with iodomethane (1 mL, excess), and stirred for 2 hours. To the reaction mixture was added a cold saturated ammonium chloride solution (30 mL) and the white precipitate obtained was collected on a filter, washed with the distilled water to afford the title compound as a white solid (0.31 g, 87%): mp 157–158° C.; $^1$H-NMR (DMSO-d$_6$) δ7.83 (s, 1H), 7.76 (dd, 1H, J=8.5, 2.0 Hz), 7.67 (m, 2H), 7.53 (dt, 1H, J=8.3, 1.9 Hz), 7.18 (d, 1H, J=8.5 Hz), 3.33 (s, 3H), 1.67 (s, 6H); $^{19}$F-NMR (DMSO-d$_6$) δ–111.01 (m, 1F); MS (APCI) m/z 364 ([M+H]$^+$, 96%), 366 ([M+H]$^+$, 100%).

EXAMPLE 46

1-(2-Amino-5-chloro-phenyl)-2,2,2-trifluoro-ethanone

To a solution of N-(4-chlorophenyl)-2,2-dimethylpropanamide (6.7 g, 30 mmol) in anhydrous THF (100 mL) under nitrogen at 0° C. was added a solution of n-BuLi (2.5M, 30 mL, 70 mmol) in hexane in a dropwise fashion. After addition, the solution was kept stirring at 0° C. for 40 minutes and treated with a solution of 1-(trifluoroacetyl)imidazole (9 mL, 78 mmol) in anhydrous THF (10 mL). The reaction mixture was warmed to ambient temperature and kept for 18 hours. To the reaction solution was added a saturated aqueous ammonium chloride solution (50 mL) followed by addition of ethyl acetate (100 mL). The organic layer was separated and the solvent was removed in vacuo. The residue obtained was suspended in 3N aqueous hydrochloric acid solution (50 mL) and heated at reflux overnight. The reaction solution was cooled to room temperature and treated with a cold ammonium hydroxide solution to a pH above 8. The aqueous mixture was extracted with ethyl acetate (3×50 mL) and the organic layers were washed with brine and dried (MgSO$_4$). After removal of solvent, the residue was purified by a flash chromatography (silica gel, hexane:ethylacetate/4:1) to afford the title compound as a yellow solid (1 g, 15%): mp 93–94° C.; $^1$H-NMR (CDCl$_3$) δ7.70 (m, 1H), 7.33 (dd, 1H, J=9.0, 2.3 Hz), 6.70 (d, 1H, J=9.1 Hz), 6.45 (bs, 2H); MS (ESI) m/z 222(M–H, 100%), 224(M–H, 33%).

EXAMPLE 47

6-Chloro-4-methyl-4-trifluoromethyl-1,4-dihydro-benzo[d][1,3]oxazin-2-one

Prepared from 1-(2-amino-5-chloro-phenyl)-2,2,2-trifluoro-ethanone by addition of methylmagnesium bromide followed by treatment of the resultant carbinol with 1,1'-carbonyldiimidazole according to the procedure of Example 2. White solid: mp 216–216° C.; $^1$H-NMR (DMSO-d$_6$) δ10.91 (bs, 1H, D$_2$O exchangeable), 7.64 (d, 1H, J=1.6 Hz), 7.49 (dd, 1H, J=8.6, 2.3 Hz), 6.95 (d, 1H, J=8.6 Hz), 1.91 (s, 3H); $^{19}$F-NMR (DMSO-d6) δ–82.0 (s, 1F); MS (EI) m/z 264 ([M–H]$^-$, 100%), 266 ([M–H]$^{31}$, 33%). Anal. Calc. For C$_{10}$H$_7$ClF$_3$NO$_2$: C, 45.22, H, 2.66, N, 5.27. Found: C, 45.32, H, 2.77, N, 4.83.

EXAMPLE 48

6-(3-Methoxyphenyl)-4-methyl-4-trifluoromethyl-1,4-dihydro-benzo[d][1,3]oxazin-2-one A mixture of 6-chloro-4-methyl-4-trifluoromethyl-1,4-dihydro-benzo[d][1,3]-oxazin-2-one (0.2 g, 0.75 mmol), 3-methoxyphenyl boronic acid (0.13 g, 0.9 mmol), potassium phosphate (0.23 g, 1.1 mmol), and nickel (II) (diphenylphosphino)ferrocenyl dichloride (52 mg, 0.076 mmol) in anhydrous dioxane was subject to a blanket of nitrogen to remove oxygen and heated at 95° C. under nitrogen for 48 hours. Another portion of 3-methoxyphenyl boronic acid (0.13 g, 0.9 mmol) and nickel (II)

(diphenylphosphino)ferrocenyl dichloride (52 mg, 0.076 mmol) was added and the reaction solution was heated at 95° C. under nitrogen for 48 hours. The reaction solution was cooled to room temperature. Saturated aqueous ammonium chloride solution (30 mL) and ethyl acetate (50 mL) was added. The organic layer was separated and the aqueous layer was extracted with ethyl acetate (3×20 mL). The combined organic layer was washed with brine and dried (MgSO$_4$). After removal of solvent, the residue was purified by a flash chromatography (silica gel, hexane:ethyl acetate/ 4:1) to afford the title compound as a white solid (50 mg, 20%): mp 178–179° C.; $^1$H-NMR (DMSO-d$_6$) δ10.85 (bs, 1H, D$_2$O exchangeable), 7.73 (m, 2H), 7.38 (t, 1H, J=7.9 Hz), 7.23 (d, 1H, J=7.7 Hz), 7.19 (d, 1H, J=1.9 Hz), 7.02 (d, 1H, J=8.2 Hz), 6.94 (dd, 1H, J=8.2, 2.4 Hz), 3.88 (s, 3H), 1.98 (s, 3H); $^{19}$F-NMR (DMSO-d$_6$) □–81.88 (s, 1F); Anal. Calc. For C$_{17}$H$_{14}$F$_3$NO$_3$: C, 60.54, H, 4.18, N, 4.15. Found: C, 60.58, H, 4.44, N, 4.19.

EXAMPLE 49

7-(3-Methoxy-phenyl)-4,4-dimethyl-1,4-dihydro-benzo[d][1,3]-oxazin-2-one

A mixture of 7-chloro-4,4'-dimethylbenzoxazin-2-one (0.197 g, 0.93 mmol), 3-methoxyphenyl boronic acid (0.21 g, 1.4 mmol), Ni(dppf)Cl$_2$ (0.095 g, 0.14 mmol), and potassium phosphate (0.59 g, 2.79 mmol) in dioxane (10 mL) was subject to a blanket of nitrogen for 15 minutes at 50° C. and then was heated at 95° C. for 48 hours. The reaction mixture was cooled to room temperature and ethyl acetate (100 mL) was added. The organics were washed twice with aqueous ammonium chloride (30 mL), once with brine (30 mL), and dried over magnesium sulfate. The residue was purified via flash chromatography (silica gel, 40% ethyl acetate/hexane) to give 7-(3-methoxy-phenyl)-4,4-dimethyl-1,4-dihydro-benzo[d][1,3]oxazin-2-one (0.090 g, 35%) as a clear oil. The oil was triturated with ether (25 ml) to furnish a white solid: mp 167–168° C.; $^1$H-NMR (DMSO-d$_6$) δ10.3 (s, 1H), 7.42–7.28 (m, 3H), 7.14 (d, 1H, J=8.11 Hz), 7.11 (bs, 2H), 6.96 (dd, 1H, J=8.11 Hz), 3.56 (s, 3H), 1.52 (s, 6H); MS (EI) m/z 283 ([M+H]$^+$, 90%); Anal. Calc. For C$_{17}$H$_{17}$NO$_3$: C, 72.07, H, 6.05, N, 4.94. Found: C, 71.59, H, 6.08, N, 4.79.

EXAMPLE 50

6-(3-Acetyl-phenyl)4,4-dimethyl-1,4-dihydro-benzo[d][1,3]-oxazin-2-one 3-(4,4-Dimethyl-2-oxo-1,4-dihydro-2H-benzo[d][1,3] oxazin-6-yl)benzonitrile (0.25 g, 0.9 mmol) was dissolved in THF (10 mL) and cooled to 0° C. To this solution, methylmagnesium bromide (3.0 M in ether, 1.8 mL, 5.4 mmol) was added and the reaction mixture was heated to reflux under nitrogen. Upon completion of the reaction, the reaction mixture was quenched with 1 N aqueous HCl solution after cooled to rt. The mixture was extracted with ethyl acetate (100 mL), dried over MgSO$_4$ and concentrated. Purification of the residue obtained via chromatography (silica gel, 50% ethyl acetate/ hexane) gave 6-(3-acetyl-phenyl)-4,4-dimethyl-1,4-dihydro-benzo[d][1,3]oxazin-2-one as a white solid (0.031 g, 12%): mp 178–179° C.; $^1$H-NMR (CDCl$_3$) δ8.15 (t, 1H, J=1.71 Hz), 8.04 (s, 1H), 7.95 (dt, 1H, J=8.85, 1.13 Hz), 7.76 (dt, 1H, J=7.90, 1.43 Hz), 7.57 (t, 1H, J=7.72 Hz), 7.52 (dd, 1H, J=8.28, 2.11 Hz), 7.39 (d, 1H, J=1.81 Hz), 6.93 (d, 1H, J=8.19 Hz), 2.69 (s, 3H), 1.81 (s, 6H); MS (EI) m/z 295 ([M+H]$^+$, 40%)

EXAMPLE 51

6-(3-Benzoyl-phenyl)4,4-dimethyl-1,4-dihydro-benzo[d][1,3]-oxazin-2-one

Prepared from 3-(4,4-dimethyl-2-oxo-1,4-dihydro-2H-benzo[d][1,3]oxazin-6-yl)benzonitrile and phenylmagnesium bromide according to the procedure of Example 50. A white solid: mp 156–157° C.; $^1$H-NMR (DMSO-d$_6$) δ10.33 (s, 1H), 8.0–7.96 (m, 2H), 7.80 (m, 2H), 7.73–7.56 (m, 7H), 6.99 (d, 1H, J=8.06 Hz), 1.67 (s, 6H); MS (EI) m/z 357 ([M+H]$^+$, 40%); Anal. Calc. For C$_{23}$H$_{19}$NO$_3$: C, 77.29, H, 5.36, N, 3.92 Found: C, 75.7, H, 5.28, N, 3.86

EXAMPLE 52

4,4-Dimethyl-6-[3-(1H-tetrazol-5-yl)-phenyl]-1,4-dihydrobenzo[d][1,3]oxazin-2-one A mixture of 3-(4,4-dimethyl-2-oxo-1,4-dihydro-2H-benzo[d][1,3]oxazin-6-yl)benzonitrile (0.77 g, 2.8 mmol), trimethylsilyl azide (0.68 g, 5.6 mmol), and dibutyl tin oxide (0.071 g, 0.28 mmol) in dioxane (20 mL) was heated at reflux under a blanket of nitrogen. Upon completion of the reaction, the dioxane was removed, the organics taken up in ethyl acetate (100 mL), and washed with NaHCO$_3$ (100 mL). The aqueous layer was acidified with 1 N aqueous HCl and extracted with ethyl acetate (100 mL). The organic layer was dried over MgSO$_4$, and concentrated. Crystallization from ether (20 mL) gave 4,4-dimethyl-6-[3-(1H-tetrazol-5-yl)-phenyl]-1,4-dihydrobenzo[d][1,3]-oxazin-2-one as a light yellow solid (0.23 g, 26%): mp 238–240° C.; $^1$H-NMR (DMSO-d$_6$) δ10.4 (s, 1H), 8.3 (bs, 1H), 8.02 (d, 1H, J=7.66 Hz), 7.9 (d, 1H, J=7.91 Hz), 7.72–7.65 (m, 3H), 7.03 (d, 1H, J=8.75 Hz), 1.70 (s, 6H); MS (ESI) m/z 320 ([M–H]$^-$, 100%); Anal. Calc. For C$_{17}$H$_{15}$N$_5$O$_2$: C, 63.54, H, 4.71, N, 21.79. Found: C, 62.16, H, 4.67, N, 21.31.

EXAMPLE 53

4-(4,4-Dicyclopropyl-2-oxo-1,4-dihydro-2H-benzo[d][1,3]oxazin-6-yl)-thiophene-2-carbonitrile (4,4-Dicyclopropyl-1,4-dihydro-2-oxo-2H-3,1-benzoxazin-6-yl)boronic acid was prepared from 2-amino-5-bromobenzoic acid according to Example 1, 2, and 4. A white solid: mp 240–242° C.; $^1$H-NMR (DMSO-d$_6$) δ10.13 (s, 1H), 8.01 (s, 2H), 7.85 (s, 1H), 7.64 (d, 1H, J=7.9 Hz), 6.77 (d, 1H, J=7.9 Hz), 1.38 (m, 2H), 0.52 (m, 2H), 0.39 (m, 4H), 0.22 (m, 2H).

The title compound was prepared according to Procedure B from (4,4-dicyclopropyl-1,4-dihydro-2-oxo-2H-3,1-benzoxazin-6-yl)boronic acid and 4-bromo-2-thiophene carbonitrile. A white solid: mp 244–245° C.; $^1$H-NMR (DMSO-d$_6$) δ10.25 (s, 1H), 8.49 (d, 1H, J=0.87 Hz), 8.33 (s, 1H), 7.74 (d, 1H, J=1.44 Hz), 7.67 (dd, 1H, J=8.28, 1.54 Hz), 6.90 (d, 1H, J=8.28 Hz), 1.53 (m, 2H), 0.59–0.41 (m, 6H), 0.31–0.24 (m, 2H); MS (ESI) m/z 335 ([M–H]$^-$, 100%); Anal. Calc. For C$_{19}$H$_{16}$N$_2$O$_2$S: C, 67.84, H, 4.79, N, 8.33. Found: C, 64.92, H, 4.66, N, 7.71.

EXAMPLE 54

6-(3-Bromo-5-fluoro-phenyl)4,4-dicyclopropyl-1,4-dihydrobenzo-[d][1,3]oxazin-2-one Prepared according to Procedure B from (4,4-dicyclopropyl-1,4-dihydro-2-oxo-2H-3,1-benzoxazin-6-yl) boronic acid and 1,3-dibromo-5-fluorobenzene. A white solid: mp 228–229° C.; $^1$H-NMR (DMSO-d$_6$) δ10.3 (s, 1H), 7.76–7.72 (m, 2H), 7.65 (dd, 1H, J=8.32, 1.74 Hz), 7.60 (d, 1H, J=10.36 Hz), 7.51 (d, 1H, J=8.3 Hz), 6.93 (d, 1H, J=8.31 Hz), 1.63–1.54 (m, 2H), 0.58–0.41 (m, 6H), 0.30–0.28 (m, 2H); MS (APCI) m/z 402/404 ([M–H]$^-$, 100%); Anal. Calc. For C$_{20}$H$_{17}$BrFNO$_2$: C, 58.48, H, 4.17, N, 3.41. Found: C, 58.77, H, 4.23, N, 3.32.

EXAMPLE 55

3-(4,4-Dicyclopropyl-2-oxo-1,4-dihydro-2H-benzo[d][1,3]oxazin-6-yl)-5-fluoro-benzonitrile A mixture of 6-(3-bromo-5-fluoro-phenyl)-4,4-dicyclopropyl-1,4-dihydro-benzo-[d][1,3]oxazin-2-one (0.4 g, 1.0 mmol), $Zn(CN)_2$ (0.71 g, 0.61 mmol), and tetrakis(triphenylphosphine)-palladium (0) (0.07 g, 0.06 mmol) in DMF (20 mL) was subject to a blanket of nitrogen for 15 minutes at 50° C. and then was heated at 85° C. for 1 hour. After cooling to room temperature, the reaction mixture was poured into $NH_4Cl$ (100 mL) and extracted with ethyl acetate (3×50 mL). The organic layers were washed with brine, dried over $MgSO_4$, and concentrated. The clear oil obtained was triturated with ether (30 ml) to give a white solid. Recrystallization of the solid from ethyl acetate gave 3-(4,4-dicylopropyl-2-oxo-1,4-dihydro-2H-benzo[d][1,3]oxazin-6-yl)-5-fluoro-benzonitrile (0.016 g, 4.6%): mp 250–252° C.; $^1$H-NMR (DMSO-$d_6$) δ10.3 (s, 1H), 8.12 (s, 1H), 7.97 (d, 1H, J=10.54 Hz), 7.81–7.79 (m, 2H), 7.73 (dd, 1H, J=8.3, 1.59 Hz), 6.94 (d, 1H, J=8.34 Hz), 1.59 (m, 2H), 0.58–0.42 (m, 6H), 0.30–0.28 (m, 2H); MS (ESI) m/z 347 ([M–H]$^-$, 100%); Anal. Calc. For $C_{21}H_{17}FN_2O_2$: C, 72.4, H, 4.92, N, 8.04 Found: C, 72.4, H, 4.74, N, 7.61

EXAMPLE 56

6-(3-Bromo-5-methyl-phenyl)-4,4-dimethyl-1,4-dihydrobenzo-[d][1,3]oxazin-2-one

Prepared from (4,4-dimethyl-1,4-dihydro-2-oxo-2H-3,1-benzoxazin-6-yl)boronic acid and 3,5-dibromotoluene according to Procedure B. White solid: mp 231–233° C.; $^1$H-NMR (DMSO-$d_6$) δ10.4 (s, 1H), 7.66 (s, 1H), 7.58–7.56 (m, 2H), 7.50 (s, 1H), 7.37 (s, 1H), 6.95 (d, 1H, J=8.67 Hz), 2.37 (s, 3H), 1.67 (s, 6H); MS (ESI) m/z 344/346 ([M–H]$^-$, 100%); Anal. Calc. For $C_{17}H_{16}BrNO_2$: C, 58.98, H, 4.66, N, 4.05. Found: C, 58.82, H, 4.62, N, 3.94.

EXAMPLE 57

6-(3-Bromo-5-trifluoromethoxy-phenyl)4,4-dimethyl-1,4-dihydrobenzo[d][1,3]-oxazin-2-one Prepared from (4,4-dimethyl-1,4-dihydro-2-oxo-2H-3,1-benzoxazin-6-yl)boronic acid and 1, 3-dibromo-5-trifluoromethoxybenzene according to Procedure B. White solid: mp 214–216° C.; $^1$H-NMR (DMSO-$d_6$) δ10.4 (s, 1H), 7.99 (s, 1H), 7.73 (s, 1H), 7.68–7.62 (m, 3H), 6.97 (d, 1H, J=8.0 Hz), 1.68 (s, 6H); MS (ESI) m/z 414 ([M–H]$^-$, 100%); Anal. Calc. For $C_{17}H_{13}BrF_3NO_3$: C, 49.06, H, 3.15, N, 3.37. Found: C, 49.16, H, 3.05, N, 3.30.

EXAMPLE 58

3-(4,4-Dimethyl-2-oxo-1,4-dihydro-2H-benzo[d][1,3]oxazin-6-yl)-5-methyl-benzonitrile Prepared from 6-(3-bromo-5-methyl-phenyl)-4,4-dimethyl-1,4-dihydrobenzo-[d][1,3]oxazin-2-one according to the procedure of example 55. White solid: mp 256–258° C.; $^1$H-NMR (DMSO-$d_6$) δ10.4 (s, 1H), 7.99 (s, 1H), 7.86 (s, 1H), 7.67–7.62 (m, 3H), 6.97 (d, 1H, J=8.11 Hz), 2.42 (s, 3H), 1.68 (s, 6H); MS (APCI) m/z 293 ([M+H]$^+$, 100%); Anal. Calc. For $C_{18}H_{16}N_2O_2$: C, 73.96, H, 5.52, N, 9.58. Found: C, 73.26, H, 5.46, N, 9.24.

EXAMPLE 59

3-(4,4-Dimethyl-2-oxo-1,4-dihydro-2H-benzo[d][1,3]oxazin-6-yl)-5-trifluoromethoxy-benzonitrile Prepared from 6-(3-bromo-5-trifluoromethoxy-phenyl)-4,4-dimethyl-1,4-dihydrobenzo[d][1,3]oxazin-2-one according to the procedure of example 55. White solid: mp 227–228° C.; $^1$H-NMR (DMSO-$d_6$) δ10.4 (s, 1H), 8.32 (s, 1H), 8.09 (s, 1H), 7.97 (s, 1H), 7.75–7.72 (m, 3H), 6.99(d, 1H, J=8.11 Hz), 1.7 (s, 6H); MS (APCI) m/z 363 ([M+H]$^+$, 80%); Anal. Calc. For $C_{18}H_{13}F_3N_2O_3$: C, 59.67, H, 3.62, N, 7.73. Found: C, 59.63, H, 3.55, N, 7.58.

EXAMPLE 60

6-(3,5-difluoro-phenyl)4,4-dimethyl-1,4-dihydrobenzo-[d][1,3]oxazin-2-one

Prepared according to procedure B from (4,4-dimethyl-1,4-dihydro-2-oxo-2H-3,1-benzoxazin-6-yl)boronic acid and 1-bromo-3,5-difluorobenzene. A white solid: mp 218–219° C.; $^1$H-NMR (DMSO-$d_6$) δ10.4 (s, 1H), 7.67–7.65 (m, 2H), 7.49 (d, 2H, J=7.73 Hz), 7.19 (t, 1H, J=9.29 Hz), 6.96 (d, 1H, J=8.88 Hz), 1.7 (s, 6H); MS (APCI) m/z 290 ([M+H]$^+$, 100%); Anal. Calc. For $C_{16}H_{13}F_2NO_2$: C, 66.43, H, 4.53, N, 4.84. Found: C, 66.01, H, 4.46, N, 4.67.

EXAMPLE 61

6-(3,5-dichloro-phenyl)4,4-dimethyl-1,4-dihydrobenzo-[d][1,3]oxazin-2-one

Prepared from 6-bromo-4,4-dimethyl-1,4-dihydro-benzo[d][1,3]oxazin-2-one and 3,5-dichlorophenyl boronic acid according to Procedure A. A white solid: mp 245–246° C.; $^1$H-NMR (DMSO-$d_6$) δ10.4 (s, 1H), 7.77 (m, 2H), 7.67–7.64 (m, 2H), 7.56 (bs, 1H), 6.96 (d, 1H, J=7.98 Hz), 1.7 (s, 6H); MS (EI) m/z 321 ([M+H]$^+$, 40%); Anal. Calc. For $C_{16}H_{13}Cl_2NO_2$: C, 59.32, H, 4.11, N, 4.32. Found: C, 59.13, H, 4.29 N, 4.17.

EXAMPLE 62

6-(3,5-Bis-trifluoromethyl-phenyl)-4,4-dimethyl-1,4-dihydrobenzo[d][1,3]oxazin-2-one Prepared from 6-bromo-4,4-dimethyl-1,4-dihydro-benzo[d][1,3]oxazin-2-one and bis-trifluoromethylphenyl boronic acid according to Procedure A. A white solid: mp 258–260° C.; $^1$H-NMR (DMSO-$d_6$) δ10.4 (s, 1H), 8.35 (s, 2H), 8.05 (s, 1H), 7.79–7.76 (m, 2H), 7.01 (d, 1H, J=8.01 Hz), 1.7 (s, 6H); MS (ESI) m/z 390 ([M+H]$^+$, 20%); Anal. Calc. For $C_{18}H_{13}F_6NO_2$: C, 55.54, H, 3.37, N, 3.6. Found: C, 55.5, H, 3.54, N, 3.47.

EXAMPLE 63

3-(4,4-Dimethyl-2-oxo-1,4-dihydro-2H-benzo[d][1,3]oxazin-6-yl)-5-methoxy-benzonitrile A mixture of (4,4-dimethyl-1,4-dihydro-2-oxo-2H-3,1-benzoxazin-6-yl)boronic acid (4.2 g, 19.0 mmol), 3-cyano-5-methoxyphenyltriflate (5.1 g, 19.0 mmol), tetrakis(triphenylphosphine)-palladium (0) (1.1 g, 0.95 mmol), sodium carbonate (4.0 g, 38.0 mmol), and lithium bromide (5 g, 57 mmol) in DME (50 mL) and water (25 mL) was subject to a blanket of nitrogen for 15 minutes at 50° C. and then was heated at 85° C. for 1 hour. The reaction was cooled to room temperature and ethyl acetate (100 mL) was added. The organic layers were washed twice with aqueous ammonium chloride (100 mL) and once with brine (100 mL), dried over magnesium sulfate and concentrated. Purification via chromatography (silica gel, 40% ethyl acetate/ hexane) gave 3-(4,4-dimethyl-2-oxo-1,4-dihydro-2H-benzo[d][1,3]oxazin-6-yl)-5-methoxy-benzonitrile as a white solid (0.69 g, 53%): mp 254–255° C.; $^1$H-NMR (DMSO-$d_6$) δ10.4 (s, 1H), 7.84 (s, 1H), 7.67–7.61 (m, 2H), 7.55 (bs, 1H), 7.4 (bs 1H) 6.99 (d, 1H, J=7.94 Hz), 3.88 (s, 3H), 1.67 (s, 6H,); MS (EI) m/z 308 ([M+H]$^+$, 30%); Anal. Calc. For $C_{18}H_{16}N_2O_3$: C, 68.13, H, 5.40, N, 8.83. Found: C, 68.03, H, 5.22, N, 8.46.

EXAMPLE 64

6-(3-Fluoro-phenyl)-4,4-dimethyl-1,4-dihydro-benzo[d][1,3]-oxazin-2-one

Prepared from 6-bromo-4,4-dimethyl-1,4-dihydro-benzo[d][1,3]oxazin-2-one 1-bromo-3-fluorobenzene according to Procedure A. A light yellow solid: mp 181–182° C.; $^1$H-NMR (DMSO-d$_6$) δ10.4 (s, 1H), 7.62–7.44 (m, 5H), 7.16 (t, 1H, J=2.22 Hz), 6.97 (d, 1H, J=8.83), 1.67 (s, 6H); MS (EI) m/z 271 ([M+H]$^+$, 40%); Anal. Calc. For $C_{16}H_{14}FNO_2$: C, 69.91, H, 5.3, N, 5.1. Found: C, 70.0, H, 5.32, N, 4.92.

EXAMPLE 65

6-(3-Chloro-4-fluoro-phenyl)-4,4-dimethyl-1,4-dihydro-benzo[d][1,3]oxazin-2-one

Prepared from 6-bromo-4,4-dimethyl-1,4-dihydro-benzo[d][1,3]oxazin-2-one and 1-bromo-3-chloro-4-fluorobenzene according to Procedure A. White solid: mp 211–212° C.; $^1$H-NMR (DMSO-d$_6$) δ10.4 (s, 1H), 7.92 (dd, 1H, J=7.13, 2.19 Hz), 7.71–7.66 (m, 1H), 7.60–7.57 (m, 2H), 7.49 (t, 1H, J=8.95 Hz), 6.96 (d, 1H, J=8.01 Hz), 1.67 (s, 6H); MS (EI) m/z 305 ([M+H]$^+$, 20%); Anal. Calc. For $C_{16}H_{13}ClFNO_2$: C, 62.86, H, 4.29, N, 4.58. Found: C, 62.52, H, 4.45, N, 4.42.

EXAMPLE 66

3-(1-Diethoxymethyl-4,4-dimethyl-2-oxo-1,4-dihydro-2H-benzo[d][1,3]oxazin-6-yl)-5-fluoro-benzonitrile A mixture of 3-(4,4-Dimethyl-2-oxo-1,4-dihydro-2H-benzo[d][1,3]oxazin-6yl)-5-fluoro-benzonitrile (0.25 g, 0.84 mmol) and triethylorthoformate (50 mL) was heated at 160° C. for 12 hours. The excess triethylorthoformate was removed in vacuo and purification via chromatography (silica gel, 20% ethyl acetate/hexane) gave 3-(1-diethoxymethyl-4,4-dimethyl-2-oxo-1,4-dihydro-2H-benzo[d][1,3]oxazin-6-yl)-5-fluoro-benzonitrile (0.116 g, 33%) as a white solid: mp 123–124° C.; $^1$H-NMR (DMSO-d$_6$) δ7.97 (d, 1H, J=8.68 Hz), 7.66 (bs, 1H), 7.53–7.44 (m, 2H), 7.35–7.32 (m, 2H), 6.65 (s, 1H), 3.88–3.78 (m, 2H), 3.73–3.61 (m, 2H), 1.77 (s, 6H), 1.27 (t, 6H, J=7.05 Hz); MS (ESI) m/z 295 ([M–H]$^-$, 100%, lower MW ion consistent with loss of diethyl acetal); Anal. Calc. For $C_{22}H_{23}FN_2O_4$: C, 66.32, H, 5.82, N, 7.03. Found: C, 65.89, H, 5.92, N, 6.66.

EXAMPLE 67

3-Fluoro-5-(1-methoxymethyl-4,4-dimethyl-2-oxo-1,4-dihydro-2H-benzo[d][1,3]oxazin-6-yl)-benzonitrile A solution of 3-(4,4-dimethyl-2-oxo-1,4-dihydro-2H-benzo[d][1,3]oxazin-6-yl)-5-fluorobenzonitrile (0.150 g, 0.51 mmol) in DMF (5 mL) was treated at rt with sodium hydride (0.061 g, 1.53 mmol). The mixture was stirred for 30 minutes and treated with chloromethyl methylether (0.062 g, 7.7 mmol). Upon completion of the reaction, the reaction mixture was quenched with water (25 mL) and extracted with ethyl acetate (3×30 mL), dried over MgSO$_4$, and concentrated. The residue was purified via chromatography (silica gel, 25% ethyl acetate/hexane) to give 3-fluoro-5-(1-methoxymethyl4,4-dimethyl-2-oxo-1,4-dihydro-2H-benzo[d][1,3]oxazin-6-yl)-benzonitrile as a white solid (0.11 g, 65%): mp 169–171° C.; $^1$H-NMR (DMSO-d$_6$) δ8.17 (bs, 1H), 8.03 (dt, 1H, J=10.4, 2.13 Hz), 7.85–7.77 (m, 3H), 7.31 (d, 1H, J=8.49 Hz), 5.33 (s, 2H), 3.35 (s, 3H), 1.7 (s, 6H); MS (APCI) m/z 341 ([M+H]$^+$, 50%); Anal. Calc. For $C_{19}H_{17}FN_2O_3$: C, 65.32, H, 5.19, N, 8.02. Found: C, 64.92, H, 4.96, N, 7.73.

EXAMPLE 68

Phosphoric acid 6-(3-cyano-5-fluoro-phenyl)-4,4-dimethyl-4H-benzo[d][1,3]oxazin-2-yl ester diethyl ether To a solution of 3-(4,4-dimethyl-2-oxo-1,4-dihydro-2H-benzo[d][1,3]oxazin-6-yl)-5-fluorobenzonitrile (0.25 g, 0.84 mmol) in DMF (5 mL) was added sodium hydride (60% in oil, 0.101 g, 2.53 mmol). After stirred for 30 minutes, the reaction mixture was treated with diethyl chlorophosphate (0.22 mL, 1.52 mmol). Upon completion of the reaction, the reaction solution was quenched with water (25 mL) and the product extracted with ethyl acetate (2×50 mL), dried over MgSO$_4$, and concentrated. The residue was purified via chromatography (silica gel, 25% ethyl acetate/hexane) to give phosphoric acid 6-(3-cyano-5-fluoro-phenyl)-4,4-dimethyl-4H-benzo[d][1,3]oxazin-2-yl ester diethyl ether as a white solid (0.064 g, 18%): mp 196–198° C.; $^1$H-NMR (DMSO-d$_6$) δ8.19 (bs, 1H), 8.05 (d, 1H, J=10.4 Hz), 7.9–7.8 (m, 3H), 7.51 (d, 1H, J=8.41 Hz), 4.33–4.41 (m, 4H), 1.76 (s, 6H), 1.27 (t, 6H, J=7.05 Hz); MS (APCI) m/z 433 ([M+H]$^+$, 80%); Anal. Calc. For $C_{21}H_{22}FN_2O_5P$: C, 58.33, H, 5.13, N, 6.48. Found: C, 58.1, H, 5.11, N, 6.25.

EXAMPLE 69

3-(4,4-Dimethyl-2-oxo-1,4-dihydro-2H-benzo[d][1,3]oxazin-6-yl)-4-fluoro-benzonitrile Prepared from (1,4-dihydro-4,4-dimethyl-2-oxo-2H-3,1-benzoxin-6-yl)boronic acid and 5-bromo-2-fluorobenzonitrile according to Procedure B. White solid: mp 229–230° C.; $^1$H-NMR (DMSO-d$_6$) δ10.4 (s, 1H), 8.15 (dd, 1H, J=7.39, 2.12 Hz), 7.95–7.89 (m, 1H), 7.59–7.48 (m, 3H), 6.99 (d, 1H, J=8.1 Hz), 1.7 (s,6H); MS (APCI) m/z 297 ([M+H]$^+$, 100%); Anal. Calc. For $C_{17}H_{13}FN_2O_2$: C, 68.91, H, 4.42, N, 9.45. Found: C, 68.74, H, 4.83, N, 9.10.

EXAMPLE 70

8-Fluoro4,4-dimethyl-dihydro-benzo[d][1,3]oxazin-2-one

N-(tert-Butoxycarbonylamino)-3-fluorobenzoic acid (Takagishi et al. *Synlett* 4, 360–2 (1992); mp 159–161° C.) was deprotected using trifluoroacetic acid to give o-amino benzoic acid which was treated with methylmagnesium bromide to afford o-amino dimethyl carbinol. The o-amino dimethyl carbinol (2.23 g, 13.2 mmol) was treated with 1,1'-carbonyldiimidizole (2.8 g, 17.2 mmol) in THF (20 mL) at 50° C. for 12 hours. Upon completion of reaction, it was cooled to rt and ethyl acetate (100 mL) added. The organic layer was washed with 10% aqueous HCl solution (2×25 mL), dried over MgSO$_4$ and concentrated. The residue was purified via chromatography (silica gel, 10% ethyl acetate/hexane) to give 8-fluoro-4,4-dimethyl-dihydro-benzo[d][1,3]oxazin-2-one as a white solid (1.3 g, 50%): mp 127–128°

C.; $^1$H-NMR (DMSO-d$_6$) δ10.4 (s, 1H), 7.22–7.12 (m, 2H), 7.07–7.00 (m, 2H), 1.6 (s, 6H); MS (APCI) m/z 196 ([M+H]$^+$, 100%); Anal. Calc. For C$_{10}$H$_{10}$FNO$_2$: C, 61.53, H, 5.16, N, 7.18. Found: C, 61.27, H, 5.37, N, 7.02.

EXAMPLE 71

6-(3-Chloro-4-fluoro-phenyl)-8-fluoro4,4-dimethyl-1,4-dihydrobenzo[d][1,3]-oxazin-2-one To a solution of 8-fluoro-4,4-dimethyl-dihydro-benzo[d][1,3]oxazin-2-one (0.15 g, 0.77 mmol) in acetic acid (5 mL) was added dropwise a solution of bromine (0.37 g, 2.31 mmol) in acetic acid (5 mL) under nitrogen at rt. After stirred for 10 minutes, the mixture was concentrated and the residue obtained was purified by a silica gel column (hexane:ethyl acetate/4:1) to afford 6-bromo-8-fluoro-4,4-dimethyl-dihydro-benzo[d][1,3]oxazin-2-one as an off-white solid (0.176 g, 84%) which was used in next step without further purification.

A mixture of 6-bromo-8-fluoro-4,4-dimethyl-dihydro-benzo[d][1,3]oxazin-2-one (0.176 g, 0.64 mmol), 4-fluoro-3-chlorophenyl boronic acid (0.15 g, 0.84 mmol), tetrakis (triphenylphosphine)-palladium (0) (0.04 g, 0.032 mmol), and sodium carbonate (0.20 g, 1.92 mmol) in DME (10 mL) and water (5 mL) was subject to a blanket of nitrogen for 15 minutes at 50° C. and then was heated at 85° C. for 1 hour. The reaction mixture was cooled to room temperature and ethyl acetate (100 mL) was added. The organic layer was washed twice with aqueous ammonium chloride (100 mL) and once with brine (100 mL), dried over magnesium sulfate and concentrated. The residue was purified via chromatography (silica gel, 25% ethyl acetate/hexane) to give6-(3-chloro-4-fluoro-phenyl)-8-fluoro-4,4-dimethyl-1,4-dihydrobenzo[d][1,3]-oxazin-2-one as a white solid ((0.13 g, 66%): mp 246–248 ° C.; $^1$H-NMR (DMSO-d$_6$) δ10.5 (s, 1H), 8.00 (dd, 1H, J=7.09, 2.32 Hz), 7.78–7.73 (m, 1H), 7.62 (dd, 1H, J=11.86, 1.77 Hz), 7.7 (t, 2H, J=9 Hz), 1.7 (s, 6H); MS (APCI) m/z 324 ([M+H]$^+$, 100%); Anal. Calc. For C$_{16}$H$_{12}$F$_2$NO$_2$ 0.5 H$_2$O C, 57.76, H, 3.94, N, 4.21. Found: C, 57.49, H, 3.69, N, 4.03.

EXAMPLE 72

6-(3-Bromo-phenyl)-4,4-dimethyl-1,4-dihydro-benzo[d][1,3]-oxazin-2-one

Prepared from (1,4-dihydro-4,4-dimethyl-2-oxo-2H-3,1-benzoxin-6-yl)boronic acid and 1,3-dibromobenzene according to procedure B. A white solid: mp 174–175° C.; $^1$H-NMR (DMSO-d$_6$) δ10.35 (s, 1H), 7.88 (bs, 1H), 7.68 (d, 1H, J=7.5 Hz), 7.6–7.51 (m, 3H), 7.4 (t, 1H, J=7.5 Hz), 6.97 (d, 1H, J=8.57 Hz), 1.64 (s, 6H); MS (EI) m/z 331([M$^+$], 60%), 333([M$^+$], 60%); Anal. Calc. For C$_{16}$H$_{14}$BrNO$_2$: C, 57.85, H, 4.25, N, 4.22. Found: C, 57.7, H, 4.36, N, 4.09.

EXAMPLE 73

4,4-Dimethyl-6-(3-trimethylsilanylethynyl-phenyl)-1,4-dihydro-benzo[d][1,3]oxazin-2-one A mixture of 6-(3-bromo-phenyl)-4,4-dimethyl-1,4-dihydro-benzo[d][1,3]oxazin-2-one (0.8 g, 2.4 mmol), trimethylsilylacetylene (1 g, 10 mmol), tetrakis (triphenylphosphine) palladium (0) (0.17 g, 0.24 mmol), and cuprous (I) iodide (0.05 g, 0.28 mmol) in triethyl amine (20 mL) was heated under nitrogen at 80° C. for 3 hours. The reaction mixture was cooled to rt and the solvent was removed. The residue was taken up in ethyl acetate (50 mL) and washed with 1N aqueous HCl (3×20 mL) and brine ( 20 mL). The organic layer was separated and dried (MgSO$_4$). After removal of solvent, the residue was purified by a silica gel chromatography (hexane:ethyl acetate/3:1) to afford the title compound as a white solid (0.77 g, 92%): mp 240–242° C.; $^1$H-NMR (DMSO-d$_6$) δ10.3 (s, 1H), 7.74–7.69 (m, 2H), 7.61–7.58 (m, 2H), 7.48–7.40 (m, 2H), 6.96 (d, 1H, J=7.98 Hz), 1.67 (s, 6H), 0.25 (s, 9H); MS (EI) m/z 349([M$^+$], 50%); Anal. Calc. For C$_{21}$H$_{23}$NO$_2$Si0.2 EtOAc: C, 71.32, H, 6.75, N, 3.82. Found: C, 71.08, H, 6.64, N, 3.82.

EXAMPLE 74

6-(3-Ethynyl-phenyl)4,4-dimethyl-1,4-dihydro-benzo[d][1,3]-oxazin-2-one

A mixture of 4,4-dimethyl-6-(3-trimethylsilanylethynyl-phenyl)-1,4-dihydro-benzo[d][1,3]oxazin-2-one (0.7 g, 2 mmol) and potassium carbonate (2 g, excess) in anhydrous methanol was stirred at rt under nitrogen for 4 hours. The mixture was treated with ice-water (100 mL) and extracted with ethyl acetate (2×80 mL). The organic layers were washed with brine and dried with MgSO$_4$. The solvent was removed and the title compound was obtained as a off-white solid (0.4 g, 72%): mp 171–172° C.; $^1$H-NMR (DMSO-d$_6$) δ10.3, (s, 1H), 7.78 (bs, 1H), 7.72–7.69 (m, 1H), 7.6–7.57 (m, 2H), 7.49–7.43 (m, 2H), 6.97 (d, 1H, J=7.98 Hz), 4.25 (s, 1H), 1.67 (s, 6H); MS (EI) m/z 277([M$^+$], 100%); Anal. Calc. For C$_{18}$H$_{15}$NO$_2$.0.2 EtOAc: C, 76.56, H, 5.67, N, 4.75. Found: C, 76.34, H, 5.4, N, 4.7.

EXAMPLE 75

3-[3-(4,4-Dimethyl-2-oxo-1,4-dihydro-2H-benzo[d][1,3]oxazin-6-yl)-phenyl]-propynenitrile To a stirred mixture of DMSO, acetonitrile and water (9 mL/3 mL/0.5 mL) was added at rt under nitrogen cuprous cyanide (0.193 g, 2.2 mmol), sodium iodide (11 mg, 0.072 mmol), and 6-(3-ethynyl-phenyl)-4,4-dimethyl-1,4-dihydro-benzo[d][1,3]oxazin-2-one (0.2 g, 0.72 mmol). Chlorotrimethylsilane was then added to the above mixture in a dropwise manner. After addition, the mixture was heated at 50° C. for 72 hours. The reaction mixture was then cooled to rt and treated with 0.5 N aqueous HCl cold solution (50 mL). The precipitate obtained was collected on a filter and washed with water. The solid was purified on a silica gel column (hexane:ethyl acetate/2:1) to give the title compound as an off-white solid (10 mg, 4.6 %): mp 212–213° C.; $^1$H-NMR (CHCl$_3$-d$_6$) δ7.96 (s, 1H), 7.77 (s, 1H), 7.65 (d, 1H, J=7.8 Hz), 7.60 (d, 1H, J=7.69 Hz), 7.51 (d, 1H, J=7.77 Hz), 7.45 (dd, 1H, J=8.67, 2.21 Hz), 7.31 (d, 1H, J=1.55 Hz), 6.91 (d, 1H, J=8.19 Hz), 1.8 (s, 6H); MS (EI) m/z 302 ([M$^+$], 30%).

EXAMPLE 76

6-(3-Fluoro-5-nitro-phenyl)4,4-dimethyl-1,4-dihydro-benzo[d][1,3]oxazin-2-one

Prepared from (1,4-dihydro-4,4-dimethyl-2-oxo-2H-3,1-benzoxin-6-yl)boronic acid and 1-bromo-3-fluoro-5-nitrobenzene according to procedure B. A yellow solid: mp 260–261° C.; $^1$H-NMR (DMSO-d$_6$) δ10.4 (s, 1H), 8.37 (bs, 1H), 8.14–8.05 (m, 2H), 7.77–7.74 (m, 2H), 7.01 (d, 1H, J=7.94 Hz), 1.7 (s, 6H); MS (ESI) m/z 315([M–H]$^-$, 100%); Anal. Calc. For C$_{16}$H$_{13}$FN$_2$O$_4$: C, 60.76, H, 4.14, N, 8.86. Found: C, 60.34, H, 4.2, N, 8.61.

EXAMPLE 77

6-(3-Chloro-5-fluoro-phenyl)4,4-dimethyl-1,4-dihydro-benzo[d][1,3]oxazin-2-one

Prepared from (1,4-dihydro-4,4-dimethyl-2-oxo-2H-3,1-benzoxin-6-yl)boronic acid and 1-bromo-3-chloro-5- fluorobenzene according to procedure B. A white solid: mp 193–194° C.; $^1$H-NMR (DMSO-d$_6$) δ10.4 (s, 1H), 7.67–7.64 (m, 3H), 7.61–7.57 (m, 1H), 7.41–7.37 (m, 1H), 6.96 (d, 1H, J=8.72 Hz), 1.7 (s, 6H); MS (APCI) m/z 306([M+H]$^+$, 100%); Anal. Calc. For C$_{16}$H$_{13}$ClFNO$_2$: C, 62.86, H, 4.29, N, 4.58. Found: C, 62.98, H, 4.1, N, 4.6.

EXAMPLE 78

3-Chloro-5-(4,4-dimethyl-2-oxo-1,4-dihydro-2H-benzo[d][1,3]oxazin-6-yl)-benzonitrile Prepared from (1,4-dihydro-4,4-dimethyl-2-oxo-2H-3,1-benzoxin-6-yl)boronic acid and 1-bromo-3-chlorobenzonitrile according to procedure B. A white solid: mp 256–257° C.; $^1$H-NMR (DMSO-d$_6$) δ10.4 (s, 1H), 8.22 (bs, 1H), 8.15 (bs, 1H), 7.98 (bs, 1H), 7.74–7.71 (m, 2H), 6.97 (d, 1H, J=8.09 Hz), 1.7 (s, 6H); MS (ESI) m/z 311 ([M−H]$^−$, 100%); Anal. Calc. For C$_{17}$H$_{13}$ClN$_2$O$_2$: C, 65.29, H, 4.19, N, 8.96 Found: C, 65.25, H, 3.92, N, 8.71.

EXAMPLE 79

6-(3,5-Dinitro-phenyl)-4,4-dimethyl-1,4-dihydro-benzo[d][1,3]oxazin-2-one

Prepared from (1,4-dihydro-4,4-dimethyl-2-oxo-2H-3,1-benzoxin-6-yl)boronic acid and 1-bromo-3,5-dinitrobenzene according to procedure B. A yellow solid: mp 297–298° C.; $^1$H-NMR (DMSO-d$_6$) δ10.4 (s, 1H),8.88 (d, 2H, J=1.98 Hz), 8.78 (bs, 1H), 7.78–7.82 (m, 2H), 7.04 (d, 1H, J=8.23 Hz), 1.7 (s, 6H); MS (APCI) m/z 343([M−H]$^−$, 100%); Anal. Calc. For C$_{16}$H$_{13}$N$_3$O$_6$: C, 55.98, H, 3.82, N, 12.24. Found: C, 55.65, H, 3.7, N, 11.92.

EXAMPLE 80

5-(4,4-Dimethyl-2-oxo-1,4-dihydro-2H-benzo[d][1,3]oxazin-6-yl)-isophthalonitrile Prepared from (1,4-dihydro-4,4-dimethyl-2-oxo-2H-3,1-benzoxin-6-yl)boronic acid and 5-bromoisophthalonitrile according to procedure B. A white solid: mp 288–289° C.; $^1$H-NMR (DMSO-d$_6$) δ10.4 (s, 1H), 8.58 (s, 2H), 8.40 (d, 1H, J=0.77 H2) 7.80–7.75 (m, 2H), 6.99 (d, 1H, J=8.2 Hz), 1.7 (s, 6H); MS (EI) m/z 303([M$^+$], 20%); Anal. Calc. For C$_{18}$H$_{13}$N$_3$O$_2$.1.65 H$_2$O: C, 64.92, H, 4.93, N, 12.62. Found: C, 64.74, H, 4.69, N, 12.32.

EXAMPLE 81

4,4-Dimethyl-6-(3-thiazol-2-yl-phenyl)-1,4-dihydro-benzo[d][1,3]oxazin-2-one

A mixture of 6-(3-bromo-phenyl)-4,4-dimethyl-1,4-dihydro-benzo[d][1,3]oxazin-2-one (0.25 g, 0.75 mmol), tri-n-butyl-thiazol-2-yl tin (0.5 g, 1.3 mmol) in DMF (5 mL) was degassed to remove oxygen and then heated under nitrogen at 90° C. for 3 hours. The reaction mixture was cooled to rt and treated with ice-water (70 mL). Ethyl acetate (100 mL) was added and organic layer was separated, washed with brine, and dried (MgSO$_4$). After removal of solvent, the residue was purified by a silica gel column (hexane:ethyl acetate/I:1) to give the title compound as a white solid (60 mg, 23%): mp 223–224° C.; $^1$H-NMR (DMSO-d$_6$) δ10.4 (s, 1H), 9.13 (s, 1H), 8.45 (s, 1H), 7.94 (bs, 1H), 7.67–7.61 (m, 4H), 7.53 (t, 1H, J=7.68 Hz), 7.00 (d, 1H, J=8.81 Hz), 1.7 (s, 6H); MS (APCI) m/z 337([M+H]$^+$, 100%); Anal. Calc. For C$_{19}$H$_{16}$N$_2$O$_2$S.0.25 H$_2$O: C, 66.94, H, 4.88, N, 8.22. Found: C, 66.57, H, 4.65, N, 7.92.

EXAMPLE 82

6-(3-Fluoro-5-methoxy-phenyl)-4,4-dimethyl-1,4-dihydro-benzo[d][1,3]oxazin-2-one Prepared from (1,4-dihydro4,4-dimethyl-2-oxo-2H-3,1-benzoxin-6-yl)boronic acid and 3-bromo-5-fluoroanisole according to procedure B. A white solid: mp 181–182° C.; $^1$H-NMR (DMSO-d$_6$) δ10.4 (s, 1H), 7.62–7.59 (m, 2H), 7.13–7.06 (m, 2H), 6.97–6.94 (d, 1H, J=8.89 Hz), 6.80 (dt, 1H, J=10.95, 2.12 Hz), 3.8 (s, 3H), 1.7 (s, 6H); MS (ESI) m/z 302 ([M+H]$^+$, 100%); Anal. Calc. For C$_{17}$H$_{16}$FNO$_3$.0.1 H$_2$O: C, 67.36, H, 5.39, N, 4.62. Found: C, 67.11, H, 5.44, N, 4.48.

EXAMPLE 83

6-(3-Fluoro-5-trifluoromethyl-phenyl)-4,4-dimethyl-1,4-dihydro-benzo[d][1,3]oxazin-2-one Prepared from (1,4-dihydro-4,4-dimethyl-2-oxo-2H-3,1-benzoxin-6-yl)boronic acid and 1-bromo-3-fluoro-5-trifluoromethylbenzene according to procedure B. A white solid: mp 207–208° C.; $^1$H-NMR (DMSO-d$_6$) δ10.4 (s, 1H), 7.94–7.9 (m, 2H), 7.73–7.7 (m, 2H), 7.63 (d, 1H, J=8.58 Hz), 6.99 (d, 1H, J=8.68 Hz), 1.7 (s, 6H); MS (EI) m/z 339([M$^+$], 60%); Anal. Calc. For C$_{17}$H$_{13}$F$_4$NO$_2$: C, 60.18, H, 3.86, N, 4.13 Found: C, 59.9, H, 3.99, N, 4.06.

EXAMPLE 84

6-(5-Bromo-pyridin-3-yl)-4,4-dimethyl-1,4-dihydro-benzo[d][1,3]oxazin-2-one

Prepared from (1,4-dihydro-4,4-dimethyl-2-oxo-2H-3,1-benzoxin-6-yl)boronic acid and 3,5-dibromopyridine according to procedure B. A white solid: mp 211–212 ° C.; $^1$H-NMR (DMSO-d$_6$) δ10.4 (s, 1H), 8.92 (d, 1H, J=1.9 Hz), 8.66 (d, 1H, J=2.09 Hz ), 8.40 (t, 1H, J=2.02 Hz), 7.72–7.68 (m, 2H), 6.99 (d, 1H, J=8.1 Hz), 1.7 (s, 6H); MS (APCI) m/z 333([M+H]$^+$, 100%), 335([M+H]$^+$, 100%); Anal. Calc. For C$_{15}$H$_{13}$BrN$_2$O$_2$: C, 54.07, H, 3.93, N, 8.41. Found: C, 54.15, H, 3.89, N, 8.31.

EXAMPLE 85

6-(5-Bromo-1-oxy-pyridin-3-yl)4,4-dimethyl-1,4-dihydro-benzo[d][1,3]oxazin-2-one A mixture of 6-(5-bromo-pyridin-3-yl)4,4-dimethyl-1,4-dihydro-benzo[d][1,3]oxazin-2-one (0.34 g, 1 mmol), hydrogen peroxide (30%, 5 mL) in acetic acid (5 mL) was heated at 60° C. for 3 hours. The reaction mixture was cooled to rt and neutralized by addition of a cold saturated sodium bicarbonate solution. The white precipitate obtained was collected on a filter, washed with distilled water and dried to afford the title compound as a white solid (0.35 g, 100%): mp 157–159° C.; $^1$H-NMR (DMSO-d$_6$) δ10.4 (s, 1H), 8.69 (s, 1H), 8.53 (s, 1H), 7.99 (s, 1H), 7.73–7.69 (m, 2H), 6.97 (d, 1H, J=8.18 Hz), 1.7 (s, 6H); MS (APCI) m/z 349([M+H]$^+$, 100%), 351([M+H]$^+$, 100%); Anal. Calc. For C$_{15}$H$_{13}$BrN$_2$O$_3$.2.5 H$_2$O: C, 45.70, H, 4.60, N, 7.11. Found: C, 45.34, H, 4.64, N, 7.

EXAMPLE 86

6-(3-Cyano-5-fluoro-phenyl)-4,4-dimethyl-2-oxo-4H-benzo[d][1,3]oxazine-1-carboxylic acid tert-butyl ester A mixture of 3-(4,4-dimethyl-2-oxo-1,4-dihydro-2H-benzo[d][1,3]oxazin-6-yl)-5-fluorobenzonitrile (0.3 g, 1 mmol), di-tert-butyl dicarbonate (0.33 g, 1.5 mmol), and DMAP (50 mg) in anhydrous acetonitrile was stirred at rt under nitrogen for 4 minutes. The reaction mixture was washed with 1N aqueous HCl, brine, dried (MgSO$_4$). After removal of solvent, the title compound was obtained as a white solid (0.25 g, 63%): mp 139–140° C.; $^1$H-NMR (CDCl$_3$-d$_6$) δ7.66–7.63 (m, 2H), 7.53–7.48 (m, 2H), 7.38–7.35 (m, 2H), 1.79 (s, 6H), 1.62 (s, 9H); MS (APCI) m/z 289([M−H]$^−$, 100%); Anal. Calc. For C$_{22}$H$_{21}$FN$_2$O$_4$: C, 66.66, H, 5.34, N, 7.07. Found: C, 66.7, H, 5.41, N, 7.

EXAMPLE 87

5-(4,4-Dimethyl-2-oxo-1,4-dihydro-2H-benzo[d][1,3]oxazin-6-yl)-2-fluoro-benzonitrile Prepared from (1,4-dihydro-4,4-dimethyl-2-oxo-2H-3,1-benzoxin-6-yl)boronic acid and 1-bromo-2-fluorobenzonitrile according to procedure B. A white solid: mp 255–256° C.; $^1$H-NMR (DMSO-d$_6$) δ10.4 (s, 1H), 8.30 (dd, 1H, J=6.15, 2.41 Hz), 8.12–8.07 (m, 1H), 7.76–7.58 (m, 3H), 6.97 (d, 1H, J =8.22 Hz), 1.7 (s, 6H), MS (APCI) m/z 297 ([M+H]$^+$, 100%); Anal. Calc. For C$_{17}$H$_{13}$FN$_2$O$_2$·0.1 H$_2$O: C, 68.50 H, 4.46, N, 9.40. Found: C, 68.27, H, 4.81, N, 9.1.

EXAMPLE 88

4-(8-Fluoro-4,4-dimethyl-2-oxo-1,4-dihydro-2H-benzo[d][1,3]oxazin-6-yl)-thiophene-2-carbonitrile 8-Fluoro-(1,4-dihydro-4,4-dimethyl-2-oxo-2H-3,1-benzoxin-6-yl)boronic acid was prepared from 6-bromo-8-Fluoro-4,4-dimethyl-dihydro-benzo[d][1,3]oxazin-2-one using the procedure of example 4.

The title compound was prepared from 8-fluoro-(1,4-dihydro-4,4-dimethyl-2-oxo-2H-3,1-benzoxin-6-yl)boronic acid and 4-bromo-2-cyanothiophene according to procedure B. A white solid: mp 250–251° C.; $^1$H-NMR (DMSO-d$_6$) δ10.5 (s, 1H), 8.54 (d, 1H, J=1.42 Hz), 8.43 (d, 1H, J=1.35 Hz), 7.69 (dd, 1H, J =11.71, 1.54 Hz), 7.58 (bs, 1H), 1.7 (s, 6H); MS (EI) m/z 302([M$^+$], 50%); Anal. Calc. For C$_{15}$H$_{11}$FN$_2$O$_2$S·0.45 H$_2$O: C, 58.04, H, 3.86, N, 9.02 Found: C, 58.4, H, 3.89 N, 8.63.

EXAMPLE 89

3-Fluoro-5-(8-fluoro-4,4-dimethyl-2-oxo-1,4-dihydro-2H-benzo[d][1,3]oxazin-6-yl)-benzonitrile Prepared from 8-fluoro-(1,4-dihydro-4,4-dimethyl-2-oxo-2H-3,1-benzoxin-6-yl)boronic acid and 5-bromo-3-fluorobenzonitrile according to procedure B. A white solid: mp 256–257° C.; $^1$H-NMR (DMSO-d$_6$) δ10.5 (s, 1H), 8.20 (bs, 1H), 8.06 (dt, 1H, J=10.48,2.16 Hz),7.85–7.82(m, 1H), 7.77 (dd, 1H, J=11.89,1.81 Hz), 7.63 (s, 1H), 1.7 (s, 6H); MS (EI) m/z 314([M$^+$], 60%).

EXAMPLE 90

5-(4,4-Dimethyl-2-oxo-1,4-dihydro-2H-benzo[d][1,3]oxazin-6-yl)-thiophene-3-carbonitrile Prepared according to procedure B from (1,4-dihydro-4,4-dimethyl-2-oxo-2H-3,1-benzoxin-6-yl)boronic acid and 2-bromo4-thiophenecarbonitrile. An off-white solid: mp 255–260° C.; $^1$H-NMR (DMSO-d$_6$) δ10.36 (s, 1H), 8.48(d, 1H, J =1.1 Hz),7.88–7.87 (d, 1H J=1.3 Hz), 7.63 (d, 1H J=1.9 Hz),7.56–7.54 (dd, 1H, J=8.0, 2.0 Hz), 6.93 (d, 1H, J=8.1 Hz),1.64 (s, 6H). MS(-ESI) m/z 283 (M−H)$^−$.

EXAMPLE 91

2-(4,4-Dimethyl-2-oxo-1,4-dihydro-2H-benzo[d][1,3]oxazin-6-yl)-thiophene-3-carbonitrile Prepared according to procedure B from (1,4-dihydro-4,4-dimethyl-2-oxo-2H-3,1-benzoxin-6-yl)boronic acid and 2-bromo-3-thiophenecarbonitrile. An off-white solid: mp 200–202° C.; $^1$H-NMR (DMSO-d$_6$) δ10.49 (s, 1H),7.75(m, 1H),7.63(d, 1H, J=2.2 Hz), 7.59 (m, 1H), 7.50 (m, 1H), 7.02 (d, 1H, J=8.1 Hz), 1.63(s, 6H); MS(-ESI) m/z 283 (M−H)$^−$.

EXAMPLE 92

6-(1,2,4-thiadiazol-3-yl-phenyl)-4,4-dimethyl-1,4-dihydro-benzo[d][1,3]oxazin-2-one A mixture of 5-[3-bromo-phenyl]-[1,3,4]oxathiazole-2-one (21.25 g, 82.3 mmol), ethylcyano formate (32.5 mL, 329 mmol) in o-xylene (500 mL) was heated to 150° C. for 60 hours. After the solvent was removed from the reaction mixture, the product was recrystallized from ethanol to give 3-[3-bromo-phenyl]-[1,2,4]thiadiazole-5-carboxylic acid ethyl ester as white crystals (17.5 g, 68%): mp 87–90° C.; $^1$H-NMR (CDCl$_3$) δ8.53 (t, 1H, J=1.76 Hz), 8.28 (dt, 1H, J=5.4, 1.2 Hz), 7.62 (dq, 1H, J=5.1, 1.0 Hz), 7.36 (t, 1H, J=7.9 Hz), 4.55 (q, 2H, J=7.1 Hz), 1.48 (t, 3H, J=7.1 Hz); MS ((+)APCI) [M+H]$^+$ @ m/z 313/315. Anal. Calc. For C$_{11}$H$_9$BrN$_2$O$_2$S: C, 42.19, H, 2.90, N, 8.94. Found: C, 41.81, H, 3.08, N, 8.78.

A mixture of 3-[3-bromo-phenyl]-[1,2,4]thiadiazole-5-carboxylic acid ethyl ester (16.8 g, 53.5 mmol), sodium hydroxide (2.4 g, 58.8 mmol), distilled water (120 mL), and ethanol (20 mL) was heated to 100° C. for 2 hours. The reaction mixture was cooled to room temperature. Concentrated hydrochloric acid (5.1 mL) was added, and the reaction mixture re-heated to 100° C. for 3 hours. The solution was cooled to room temperature and extracted with diethyl ether (3×150 mL). The combined organic layers were washed with distilled water (3×100 mL), and dried over MgSO$_4$. After the solvent was removed, 3-[3-bromo-phenyl]-[1,2,4]thiadiazole was obtained as white needles (12.7 g, 99%): mp 69–71° C.; $^1$H-NMR (CDCl$_3$) δ9.89 (s, 1H), 8.52 (t, 1H, J=1.8 Hz), 8.28 (dt, 1H, J=5.2, 1.3 Hz), 7.61 (dq, 1H, J=4.9, 1.1 Hz), 7.35 (t, 1H, J=7.9 Hz); MS ((+) APCI) [M+H]$^+$ @ m/z 241/243. Anal. Calc. For C$_8$H$_5$BrN$_2$S: C, 39.85, H, 2.09, N, 11.62. Found: C, 39.82, H, 2.43, N, 11.33.

According to procedure B, (1,4-dihydro-4,4-dimethyl-2-oxo-2H-3,1-benzoxazin-6-yl)boronic acid was coupled with 3-[3-bromo-phenyl]-[1,2,4]thiadiazole to yield 6-(1,2,4-thiadiazol-3-yl-phenyl)-4,4-dimethyl-1,4-dihydro-benzo[d][1,3]-oxazin-2-one as an off-white solid (0.5 g, 35%): mp 214–216° C.; $^1$H-NMR (DMSO-d$_6$) δ10.40 (s, 1H), 10.36 (s, 1H), 8.49 (s, 1H), 8.23 (d, 1H, J=7.7 Hz), 7.83 (d, 1H, J=7.9 Hz), 7.66–7.61 (m, 3H), 7.02 (t, 1H, J=4.4 Hz), 1.70 (s, 6H); MS ((+)APCI) [M+H]$^+$ @ m/z 338.

EXAMPLE 93

6-(3-Fluoro-5-thiophen-3-yl-phenyl)-4,4-dimehtyl-1,4-dihydro-benzo[d][1,3]oxazin-2-one Prepared from 6-(3-bromo-5-fluoro-phenyl)-4,4-dimethyl-1,4-dihydro-benzo[d][1,3]oxazin-2-one and 3-thiophene boronic acid according to procedure B. A brownish-orange solid: mp 200–203° C.; $^1$H-NMR (CDCl$_3$) δ8.62 (s, 1H), 7.53 (q, 1H, J=1.4 Hz), 7.50 (d, 1H, J=1.5 Hz), 7.49 (d, 1H, J=2.0 Hz), 7.45–7.40 (m, 1H), 7.35 (d, 1H, J=1.8 Hz), 7.27–7.24 (m, 2H), 7.15 (dt, 1H, J=5.8, 2.0 Hz), 6.94 (d, 1H, J=8.2 Hz), 1.80 (s, 6H); MS ((−)APCI) [M−H]⁻ @ m/z 352. Anal. Calc. For $C_{20}H_{16}FNO_2S \cdot 0.50\ H_2O$: C, 66.28, H, 4.73, N, 3.87. Found: C, 66.54, H, 5.03, N 3.52.

EXAMPLE 94

2-(4,4-Dimethyl-2-oxo-1,4-dihydro-2H-benzo[d][1,3]oxazin-6-yl)-pyrrole-1-carboxylic acid tert-butyl ester A solution of 6-bromo-4,4-dimethyl-1,4-dihydro-benzo[d][1,3]oxazin-2-one (0.87 g, 3.4 mmol) and tetrakis(triphenylphosphine)palladium(0) (96 mg, 0.08 mmol) in toluene (40 mL) was stirred under a flow of nitrogen for 25 min. To the solution was added sequentially 1-t-butoxycarbonylpyrrole-2-boronic acid (1.4 g, 7.0 mmol) in absolute ethanol (10 mL) and potassium carbonate (0.94 g, 7.0 mmol) in water (10 mL). The mixture was heated at 80° C. for 16 h and allowed to cool to rt. The reaction mixture was poured into aqueous saturated sodium bicarbonate solution (100 mL) and extracted with ethyl acetate (3×100 mL). The organic layers were combined, washed with water (100 mL) and brine (50 mL) and dried over magnesium sulfate. The solution was filtered, concentrated in vacuo, and the residue was purified by flash column chromatography on silica gel (30% ethyl acetate/hexane) to give the title compound as an off-white powder (0.7 g, 62%): mp 176° C. ¹H NMR (CDCl₃) δ1.40 (s, 9H), 1.73 (s, 6H), 6.17 (dd, 1H, J=1.8, 3.3 Hz), 6.22 (dd, 1H, J=3.3, 3.3 Hz), 6.77 (d, 1H, J=8.1 Hz), 7.13 (d, 1H, J=1.8 Hz), 7.23 (dd, 1H, J=1.8, 8.1 Hz), 7.33 (dd, 1H, J=1.8, 3.3 Hz), 7.69 (bs, 1H). MS ((−) ESI) m/z 341 [M−H]⁻. Anal. Calcd for $C_{19}H_{22}N_2O_4$: C, 66.65; H, 6.48; N, 8.18. Found: C, 65.46; H, 6.51; N, 7.74.

EXAMPLE 95

2-(4,4-Dimethyl-2-oxo-1,4-dihydro-2H-benzo[d][1,3]oxazin-6-yl)-5-nitro-pyrrole-1-carboxylic acid tert-butyl ester To a solution of 2-(4,4-dimethyl-2-oxo-1,4-dihydro-2H-benzo[d][1,3]oxazin-6-yl)-pyrrole-1-carboxylic acid tert-butyl ester (0.7 g, 2.0 mmol) in acetonitrile (25 mL) and dichloromethane (1 mL) at room temperature was added silver nitrate (0.37 g, 2.1 mmol). After 5 min, acetyl chloride (0.15 mL, 2.0 mmol) in acetonitrile (3 mL) was added and the solution was allowed to stir for 2 h. The reaction mixture was poured into water (50 mL) and extracted with ethyl ether (2×50 mL). The organic layers were combined, washed with brine (30 mL) and dried over magnesium sulfate. The solution was filtered, concentrated in vacuo and the residue was purified by flash column chromatography on silica gel (30% ethyl acetate/hexane) to give a yellow oil which crystallized from 5% ethyl acetate/hexane to give the title compound as a bright yellow powder (350 mg, 45%): mp 125° C. ¹H NMR (CDCl₃) δ1.47 (s, 9H), 1.75 (s, 6H), 6.26 (d, 1H, J=4.2 Hz), 6.87 (d, 1H, J=8.1 Hz), 7.19 (d, 1H, J=4.2 Hz), 7.34 (d, 1H, J=2 Hz), 7.4 (dd, 1H, J=1.8, 8.1 Hz), 8.17 (bs, 1H). MS ((+) APCI) m/z 388 [M+H]⁺. Anal. Calcd for $C_{19}H_{21}N_3O_6$: C, 58.91; H, 5.46; N, 10.85. Found: C, 58.4; H, 5.55; N, 10.18.

EXAMPLE 96

4,4-Dimethyl-6-(5-nitro-1H-pyrrol-2-yl)-1,4-dihydobenzo[d][1,3]oxazin-2-one 2-(4,4-Dimethyl-2-oxo-1,4-dihydro-2H-benzo[d][1,3]oxazin-6-yl)-5-nitro-pyrrole-1-carboxylic acid tert-butyl ester (0.7 g, 1.8 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 180° C. After 10 min at this temperature, the flask was removed from the oil bath and allowed to cool to rt. The brown residue was washed into a larger flask with dichloromethane/ethyl acetate and adsorbed onto a small amount of silica gel. Purification by flash column chromatography on silica gel (60% ethyl acetate/hexane) gave the title compound as a brown powder (200 mg, 40%): mp 265° C. (dec). ¹H NMR (DMSO-d₆) δ1.65 (s, 6 H), 6.81 (d, 1H, J=4.4 Hz), 6.90 (d, 1H, J=8.6 Hz), 7.25 (d, 1H, J=4.2 Hz), 7.79 (dd, 1H, J=2, 8.3 Hz), 7.91 (d, 1H, J=2 Hz), 10.37 (s, 1H), 13.17 (bs, 1H). MS ((−) ESI) m/z 286 [M−H]⁻. Anal. Calcd for $C_{14}H_{13}N_3O_4$: C, 58.53; H, 4.56; N, 14.63. Found: C, 58.25; H, 5.10; N, 12.57.

EXAMPLE 97

4,4-Dimethyl-6-(1H-pyrrol-2-yl)-1,4-dihydro-benzo[d][1,3]-oxazin-2-one 2-(4,4-Dimethyl-2-oxo-1,4-dihydro-2H-benzo[d][1,3]oxazin-6-yl)-pyrrole-1-carboxylic acid tert-butyl ester (3.5 g, 10 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 180° C. After 10 min at this temperature, the flask was removed from the oil bath and allowed to cool. The brown residue was washed into a larger flask with dichloromethane/ethyl acetate and adsorbed onto a small amount of silica gel. Purification by flash column chromatography on silica gel (60% ethyl acetate/hexane) gave the title compound as a green solid (2 g, 80%): mp 202° C (dec). ¹H NMR (CDCl₃) δ1.75 (s, 6H), 6.30 (m, 1H), 6.45 (m, 1H), 6.85 (d, 1H, J=8.5 Hz), 6.86 (m, 1H), 7.24 (d, 1 H, J=2 Hz), 7.33 (dd, 1H, J=2, 8.4 Hz), 8.44 (bs, 1H), 8.66 (s, 1H). MS ((+) APCI) m/z 243 [M+H]⁺. Anal. Calcd for $C_{14}H_{14}N_2O_2$: C, 69.41; H, 5.82; N, 11.56. Found: C, 69.20; H, 5.96; N, 11.29.

EXAMPLE 98

4,4-Dimethyl-6-(1-methyl-1H-pyrrol-2-yl)-1,4-dihydro-benzo[d][1,3]oxazin-2-one

To a mixture of 4,4-dimethyl-6-(1H-pyrrol-2-yl)-1,4-dihydro-benzo[d][1,3]oxazin-2-one (1.5 g, 6.2 mmol) in dimethylformamide (20 mL) at room temperature was added sequentially potassium carbonate (4.28 g, 31 mmol) and a solution of methyl iodide (1.16 mL, 19 mmol) in dimethylformamide (5 mL). After 1 h, the reaction mixture was boiled. The reaction was cooled to room temperature, poured into water (50 mL) and extracted with ethyl ether (2×50 mL). The organic layers were combined, washed with brine (30 mL), dried over magnesium sulfate, filtered and concentrated in vacuo. Purification by flash column chromatography on silica gel (40% ethyl acetate/hexane) gave the title compound as an off-white powder (0.5 g, 31%) mp 230° C. ¹H NMR (CDCl₃) δ1.71 (s, 6H), 3.42 (s, 3H), 6.31 (dd, 1H, J=2.9, 5.9 Hz), 6.47 (m, 1H), 6.88 (m, 1H), 6.94 (d, 1H, J=8.6 Hz), 7.26 (d, 1H, J=2.2 Hz), 7.41 (dd, 1H, J=2.2, 8.6 Hz), 8.43 (bs, 1H). MS ((−) ESI) m/z 255 [M−H]⁻. Anal. Calcd for $C_{15}H_{16}N_2O_2$: C, 70.29; H, 6.29; N, 10.93. Found: C, 68.59; H, 6.16; N, 10.49.

EXAMPLE 99

4,4-Dimethyl-6-(1-methyl-5-nitro-1H-pyrrol-2-yl)-1,4-dihydro-benzo[d][1,3]oxazin-2-one To a solution of 4,4-dimethyl-6-(1-methyl-1H-pyrrol-2-yl)-1,4-dihydro-benzo [d][1,3]oxazin-2-one (0.3 g, 1.2 mmol) in acetonitrile (20 mL) was added silver nitrate (0.21 g, 1.26 mmol). The solution was cooled to −78° C. and treated with a solution of acetyl chloride (0.08 mL, 1.2 mmol) in acetonitrile (1 mL). The reaction mixture was allowed to warm to room temperature. After 1 h, the reaction mixture was poured into water (50 mL) and extracted with ethyl ether (2×50 mL). The organic layers were combined, washed with brine (30 mL), dried over magnesium sulfate, filtered and concentrated in vacuo. Purification by flash column chromatography on silica gel (40% ethyl acetate/hexane) gave the title compound (5 mg, 1%) as a yellow solid, mp 180–185° C. $^1$H NMR (CDCl$_3$) δ1.75 (s, 6H), 3.45 (s, 3H), 6.57 (dd, 1H, J=2.9, 4.3 Hz), 7.04 (d, 1H, J=8.5 Hz), 7.22 (dd, 1H, J=2.5, 4.3 Hz), 7.36 (d, 1H, J=2.1 Hz), 7.56 (dd, 1H, J=2.1, 8.5 Hz), 9.67 (bs, 1H). MS ((+) APCI) m/z 302 [M+H]$^+$.

EXAMPLE 100

5-Bromo-4-ethylthiophene-2-carboxaldehyde

Prepared from 2-bromo-3-ethylthiophene in a similar manner to the example 19. $^1$H-NMR(DMSO-d$_6$) δ9.82 (S, 1H), 7.81 (S, 1H), 2.5 (q, 2H, J=7.4 Hz), 1.15 (t, 3H, J=7.5 Hz).

EXAMPLE 101

5-Bromo-4-ethylthiophene-2 carbonitrile

Prepared from 5-bromo-4-ethylthiophene-2-carboxaldehyde using the similar procedure of example 18. IR(KBr) 2221 cm$^{-1}$; $^1$H-NMR(DMSO-d$_6$) δ7.87 (S, 1H), 2.55 (q, 2H, J=7.3 Hz), 1.18 (t, 3H, J=7.6 Hz). MS (EI) m/z 215/217(M$^+$).

EXAMPLE 102

5-Bromo4-n-propylthiophene-2-carboxaldehyde

Prepared from 2-bromo-3-n-propylthiophene in a similar manner to the example 19. $^1$H-NMR(DMSO-d$_6$) δ9.82 (S, 1H), 2.6–2.5 (m, 2H), 1.65–1.51 (m, 2H), 1.0 (t, 3H, J=4.7 Hz).

EXAMPLE 103

5-Bromo-4-n-propylthiophenecarbonitrile

Prepared from 5-bromo-4-n-propylthiophene-2-carboxaldehyde using the similar procedure of example 18. $^1$H-NMR(DMSO-d$_6$) δ7.87 (S, 1H), 2.5 (t, 2H, J=5.2 Hz), 1.64–1.5 (m, 2H), 1.91 (t, 3H, J=5.1 Hz). MS(EI) m/z 229–231(M$^+$).

EXAMPLE 104

5-Bromo4-n-butylthiophenecarboxaldehyde

Prepared from 2-bromo-3-n-butylthiophene in a similar manner to the example 19. IR(KBr) 1660 cm$^{-1}$. $^1$H-NMR (DMSO-d$_6$) δ9.78 (S, 1H), 7.85 (S, 1H), 2.57–2.53 (m, 2H), 1.57–1.53 (m, 2H), 1.32–1.25 (m, 2H), 0.88 (t, 3H, J=5.2 Hz). MS (EI) m/z 246(M$^+$).

EXAMPLE 105

5-Bromo4-n-butylthiophenecabonitrile

Prepared from 5-bromo-4-n-butylthiophenecarboxalde-hyde using the similar procedure of example 18. $^1$H-NMR (DMSO-d$_6$) δ7.87 (S, 1H), 2.58–2.44 (m, 2H), 1.65–1.48 (m, 2H), 1.38–1.23 (m, 2H), 0.89 (t, 3H, J=5.3 Hz). MS (EI) m/z 243 (M$^+$).

EXAMPLE 106

3-(1,2-Dihydro-2-oxospiro[4H-3,1-benzoxazine-4,1-cyclohexan]-6-yl)-benzonitrile

Prepared according to Procedure B from spiro-(4,1'-cyclohexane-1,4-dihydro-2-oxo-2H-3,1-benzoxazin-6-yl) boronic acid and 3-bromobenzonitrile. Tan powder: mp 245–247° C. $^1$H-NMR(DMSO-d$_6$) δ10.31 (S, 1H), 8.21 (S, 1H), 8.02 (d, 1H, J=8.0 Hz), 7.78 (d, 1H, J=7.7 Hz), 7.68–7.61 (m, 3H), 6.97 (d, 1H, J=8.2 Hz), 1.98–1.96 (m, 4H), 1.75–1.64 (m, 5H), 1.40–1.32 (m, 1H). MS (EI) m/z 318[M$^+$]. Anal. Calc. For C$_{20}$H$_{18}$N$_2$O$_2$.½ H$_2$O: C 73.38; H, 5.85; N, 8.56. Found: C, 73.86; H, N, 8.22.

EXAMPLE 107

3-(1,2-Dihydro-2-oxospiro[4H-3,1-benzoxazine-4,1-cyclohexan]-6-yl)-5-fluorobenzonitrile Prepared according to Procedure B from spiro-(4,1'-cyclohexane-1,4-dihydro-2-oxo-2H-3,1-benzoxazin-6-yl) boronic acid and 3-bromo-5-fluorobenzonitrile. White powder: mp 250–253° C. IR (KBr) 2220 cm$^{-1}$. $^1$H-NMR (DMSO-d$_6$) δ10.34 (S, 1H), 8.13 (S, 1H), 8.0 (d, 1H, J=10.6 Hz), 7.80–7.7 (m, 3H), 6.98–6.95 (d, 1H, J=8.1 Hz), 1.99–1.97 (m, 4H), 1.76–1.65 (m, 6H), 1.37–1.33 (m. 1H). MS (EI) m/z 336 (M$^+$). Anal. Calc. For C$_{20}$H$_{17}$FN$_2$O$_2$H$_2$O: C, 67.78; H, 5.40; N, 7.90. Found: C, 67.9; H, 4.93; N, 7.67.

EXAMPLE 108

4-(1,2-Dihydro-2-oxospiro [4H-3,1-benzoxazine-4,1-cyclohexan]-6-yl)-2-thiophenecarbonitrile Prepared according to Procedure B from spiro-(4,1'-cyclohexane-1,4-dihydro-2-oxo-2H-3,1-benzoxazin-6-yl) boronic acid and 3-bromo-5-cyanothiophene. White crystals: mp 230–232° C. IR (KBr) 2200 cm$^{-1}$. $^1$H-NMR (DMSO-d$_6$) δ10.29 (S, 1H), 8.49 (S, 1H), 8.33 (S, 1H), 7.69–7.63 (m, 2H), 6.93–6.91 (d, 1H, J=8.2 Hz), 1.99–1.87 (m, 4H), 1.73–1.64 (m, 5H), 1.38–1.31 (m, 1H). MS(+) APCI m/z 325 (M+H)$^+$. Anal. Calc. For C$_{18}$H$_{16}$N$_2$O$_2$S¼H$_2$O: C, 65.73; H, 5.06; N, 8.52. Found: C, 65.55; H, 5.06; N, 8.22.

EXAMPLE 109

5-(1,2-Dihydro-2-oxospiro [4H-3,1-benzoxazine-4,1-cyclohexan]-6-yl)-2-thiophenecarbonitrile Prepared according to Procedure B from spiro-(4,1'-cyclohexane-1,4-dihydro-2-oxo-2H-3,1-benzoxazin-6-yl) boronic acid and 2-bromo-5-cyanothiophene Tan powder: mp 243–245° C. $^1$H-NMR(DMSO-d$_6$) δ10.41(s, 1H), 7.98–7.97 (d, 1H, J=3.9 Hz), 7.67–7.60 (m, 3H), 6.97–6.94 (d, 1H, J=8.3 Hz), 1.98–1.92 (m, 4H), 1.74–1.64 (m, 5H), 1.45–1.21 (m, 1H). MS (EI) m/z 324 (M$^+$). Anal. Calc. For C$_{18}$H$_{16}$N$_2$O$_2$S½ H$_2$O: C, 65.08; H, 5.04; N, 8.18. Found: C, 64.84; H, 5.09; N,8.40.

EXAMPLE 110

5-(1,2-Dihydro-2-oxospiro[4H-3,1-benzoxazine-4,1-cyclohexan]-6-yl)-4-methyl-2-thiophenecabonitrile Prepared according to Procedure B from spiro-(4,1'-cyclohexane-1,4-dihydro-2-oxo-2H-3,1-benzoxazin-6-yl)

boronic acid and 2-bromo-3-methyl-5-cyanothiophene. White powder: mp 200–203° C. $^1$H-NMR (DMSO-d$_6$) δ10.4 (s, 1H), 7.85 (s, 1H), 7.43–7.40 (m, 2H), 7.0 (d, 1H, J=8.8 Hz), 2.27 (s,3H), 2.00–1.62 (m, 9H), 1.42–1.23 (m, 1H). MS(EI) m/z 338 (M$^+$). Anal. Calc. For C$_{19}$H$_{18}$N$_2$O$_2$S: C, 67.43; H, 5.36, N, 8.28. Found: C, 67.12; H, 5.45; N, 8.05.

EXAMPLE 111

5-(4,4-Dimethyl-2-oxo-1,4-dihydro-2H-benzo[d][1,3]oxazin-6-yl)-4-ethyl-thiophene-2-carbonitrile Prepared according to Procedure B from spiro-(4,1'-cyclohexane-1,4-dihydro-2-oxo-2H-3,1-benzoxazin-6-yl) boronic acid and 2-bromo-3-ethyl-5-cyanothiophene. White crystals: mp 160–162° C. $^1$H-NMR(DMSO-d$_6$) δ10.46 (s, 1H), 7.96 (s, 1H), 7.40–7.38 (m, 2H), 7.02–6.99 (d, 1H, J=8.8 Hz), 2.61 (q, 2H, J=7.5 Hz), 1.64 (s, 6H), 1.16 (t, 3H, J=7.6 Hz). MS (+) APCI m/z [M+H]$^+$313. Anal. Calc. For C$_{17}$H$_{16}$N$_2$O$_2$S.¼H$_2$O: C, 64.43; H, 5.25; N, 8.84. Found: C, 64.77; H, 5.23; N, 8.68.

EXAMPLE 112

5-(4,4-Dimethyl-2-oxo-1,4-dihydro-2H-benzo[d][1,3]oxazin-6-yl)-4-n-propyl-thiophene-2-carbonitrile Prepared according to Procedure B from spiro-(4,1'-cyclohexane-1,4-dihydro-2-oxo-2H-3,1-benzoxazin-6-yl) boronic acid and 2-bromo-3-n-propyl-5-thiophenecarbonitrile. White crystals: mp 160–162° C. IR (KBr) 2220 cm$^{-1}$. $^1$H-NMR(DMSO-d$_6$) δ10.47 (s, 1H), 7.93 (s, 1H), 7.38–7.36 (m, 2H), 7.01 (d, 1H, J=8.7 Hz), 2.59–2.48 (m, 2H), 1.64–1.51 (m, 2H), 0.85 (t, 3H, J=7.3 Hz). MS(-ESI) m/z [M–H]$^-$325. Anal. Calc. For C$_{18}$H$_{18}$N$_2$O$_2$S.¾H$_2$O: C, 63.60; H, 5.78, N, 8.24. Found: C; 63.48; H, 5.59; N, 8.04.

EXAMPLE 113

5-(4,4-Dimethyl-2-oxo-1,4-dihydro-2H-benzo[d][1,3]oxazin-6-yl)-4-n-butyl-thiophene-2-carbonitrile Prepared according to Procedure B from spiro-(4,1-cyclohexane-1,4-dihydro-2-oxo-2H-3,1-benzoxazin-6-yl) boronic acid and 2-bromo-3-n-butyl-5-thiophenecarbonitrile. White crystals: mp 167–168° C. $^1$H-NMR(DMSO-d$_6$) δ10.46 (s, 1H), 7.93 (s, 1H), 7.38–7.36 (m, 2H), 7.01 (d, 1H, J=8.7 Hz), 2.59 (t, 2H, j=8.1 Hz), 1.63 (s, 6H), 1.58–1.51 (m, 2H), 1.48–1.17 (m, 2H), 0.82 (t, 3H, J=7.4 Hz), MS(–ESI) m/z [M–H]$^-$339. Anal. Calc. For C$_{19}$H$_{20}$N$_2$O$_2$S.¼ H$_2$O: C, 66.16; H, 5.99; N, 8.12. Found: C, 66.33; H, 5.92; N, 7.85.

EXAMPLE 114

6-(4-Cyano-3-fluoro)-4,4-dimethyl-1,4-dihydrobenzo[d][1,3]-oxazin-2-one

A solution of 4-cyano-3-fluoro-bromobenzene (0.6 g, 3.0 mmol), and tetrakis(triphenylphosphine)palladium(0) (0.2 g) in ethylene glycol dimethyl ether (20 mL) was stirred under N$_2$ for 20 minutes. To this mixture was then added (1,4-dihydro-4,4-dimethyl-2-oxo-2H-3,1-benzoxazin-6-yl) boronic acid (1.0 g, 4.5 mmol) and sodium carbonate (1.1 g, 10.6 mmol) in water (5 mL). The solution was brought to reflux for 18 hours and then cooled to room temperature, poured into 2N NaOH and extracted with EtOAc (3×50 mL). The combined extracts were washed with water, brine, dried (MgSO$_4$), and evaporated. The residue was purified by column chromatography (SiO$_2$, EtOAc:hexane 1:2) to afford the title compound (0.05 g, 6%) as an off-white solid. mp: 272–275° C.; $^1$H-NMR (DMSO-d$_6$) δ10.4 (s, 1H), 8.0 (t, 1H, J=7.7 Hz), 7.9 (dd, 1H, J=10.3, 1.3 Hz), 7.8 (dd, 1H, J=6.8, 1.4 Hz), 7.7 (m, 2H), 6.9 (d, 1H, J=8.9 Hz), 1.7 (s, 6H); MS (EI) M$^+$ @ m/z 296.

EXAMPLE 115

6-(4-Fluoro-phenyl)-4,4-dimethyl-1,4-dihydro-benzo[d][1,3]-oxazin-2-one

Prepared according to Procedure B from (1,4-dihydro-4,4-dimethyl-2-oxo-2H-3,1-benzoxin-6-yl)boronic acid and 1-bromo4-fluorobenzene. Off-white crystals: mp 232–233° C. $^1$H-NMR(DMSO-d$_6$) δ10.3 (s, 1H), 7.74 (m, 2H), 7.53 (m, 2H), 7.28 (m, 2H), 6.96 (d, 1H, J=8.9 Hz), 1.63 (s, 6H).

EXAMPLE 116

6-(3,4-Difluoro-phenyl)-4,4-dimethyl-1,4-dihydro-benzo[d][1,3]oxazin-2-one

Prepared according to Procedure B from (1,4-dihydro-4,4-dimethyl-2-oxo-2H-3,1-benzoxin-6-yl)boronic acid and 1-bromo-3, 4-difluorobenzene. Off-white crystals: mp 207–208° C. $^1$H-NMR(DMSO-d$_6$) δ10.35 (s, 1H), 7.79 (m, 1H), 7.40–7.63 (m, 4H), 6.95 (d, 1H, J=8.9 Hz), 1.62 (s, 6H).

EXAMPLE 117

6-(2-Fluoro-phenyl)4,4-dimethyl-1,4-dihydro-benzo[d][1,3]-oxazin-2-one

Prepared according to Procedure B from (1,4-dihydro-4,4-dimethyl-2-oxo-2H-3,1-benzoxin-6-yl)boronic acid and 1-bromo-2-fluorobenzene. Off-white crystals: mp 164–165° C. $^1$H-NMR(DMSO-d$_6$) δ10.33 (s, 1H), 7.56 (m, 1H), 7.25–7.45 (m, 4H), 6.98 (d, 1H,J=8.7 Hz), 1.64 (s, 6H).

EXAMPLE 118

3-(4,4-Dimethyl-2-oxo-1,4-dihydro-2H-benzo[d][1,3]-oxazin-6-yl)phenylacetonitrile Prepared from 3-bromophenylacetonitrile and (1,4-dihydro-4,4-dimethyl-2-oxo-2H-3,1-6-yl)boronic acid. White solid: mp 188–190° C.; $^1$H-NMR (DMSO- d$_6$) δ10.33 (s, 1H), 7.62 (m, 2H), 7.55 (m, 2H), 7.48 (d, 1H, J=8.00 Hz), 7.33 (d, 1H, J=7.57 Hz), 6.99 (d, 1H, J=8.81 Hz), 4.09 (s, 2H), 1.67 (s, 6H); MS m/z 291(M–H). Anal. Calc. For C$_{18}$H$_{16}$N$_2$O$_2$.0.3 H$_2$O: C,72.61, H, 5.62, N, 9.41. Found: C, 73.00, H, 5.43, N, 8.81

EXAMPLE 119

5-(4,4-Dimethyl-2-oxo-1,4-dihydro-2H-benzo[d][1,3]oxazin-6-yl)-furan-2-carbonitrile The title compound was prepared according to the procedure B from 2-bromo-5-cyanofuran (1.0 g, 5.6 mmol) (J. Med. Chem. (1997), 40(23), 3804–3819) and (1,4-dihydro-4,4-dimethyl-2-oxo-2H-3,1-benzoxazin-6-yl)boronic acid (1.8 g, 8.18 mmol) as a white solid (0.39 g, 1.45 mmol, 17%): mp. 257–260° C.; $^1$H-NMR (DMSO-d$_6$) □10.48 (s, 1H), 7.73–7.70 (m, 3H), 7.19 (d, 1H, J=3.8 Hz), 6.98 (d, 1H, J=8.9 Hz), 1.66 (s, 6H); MS ((+)–APCI) m/z=269 (M+H)$^+$.

EXAMPLE 120

3-(4,4-Dimethyl-2-oxo-1,4-dihydro-2H-benzo[d][1,3]oxazin-6-yl)-2-fluoro-benzonitrile A solution of 3-bromo-2-fluorobenzoic acid (0.219 g, 1 mmol) in dry methanol (5 mL) under nitrogen was treated with trimethylorthoformate (0.22 mL, 2 mmol) and p-toluenesulfonic acid (catalytic amount), and then heated under reflux. After 16 h, the mixture was evaporated and the residue partitioned between water and Et$_2$O. the organic layer was washed with sat. sodium hydrogen carbonate solution, water, brine, dried (MgSO$_4$) and evaporated to give methyl 3-bromo-2-fluorobenzoate (0.195 g, 0.84 mmol, 84%): $^1$H-NMR (CDCl$_3$) δ7.90–7.85 (m, 1H), 7.71–7.65 (m, 1H), 7.10 (dt, 1H, J=8.0, 1.0 Hz), 3.94 (s, 3H): MS (EI) 232 (M$^+$).

A solution of the last cited compound (3.077 g, 13.2 mmol) in dry toluene (80 mL) at −78° C. under nitrogen was treated with a di-iso-butylaluminum hydride in toluene (1M, 15.7 mL, 15.7 mmol). After 1 h at −78° C., the mixture was quenched with aqueous HCl (3M, 16 mL). The mixture was warmed to RT, partitioned between EtOAc/H$_2$O, the aqueous layer was re-extracted with EtOAc, and the combined organic layers were washed with water, dried (MgSO$_4$) and evaporated to afford 3-bromo-2-fluorobenzaldehyde (2.63 g, 12.9 mmol, 98%), which was used without further purification: $^1$H-NMR (CDCl$_3$) δ10.35 (s, 1H), 7.82 (m, 2H), 7.18 (t, 7.8 Hz).

A mixture of the last cited compound (2.63 g, 12.9 mmol), hydroxylamine hydrochloride (1.0 g, 14 mmol) and potassium acetate (1.37 g, 14 mmol) was placed in ethanol/H$_2$O (60 mL, 8:2) and the mixture was heated under reflux. After 30 min. the mixture was cooled, evaporated and partitioned between EtOAc and water. The organic layer was washed with brine, dried (MgSO$_4$) and evaporated to give 3-bromo-2-fluorobenzaldoxime which was used without further characterization.

A solution of the last cited compound (0.75 g, 3.43 mmol) and tetrakis(triphenylphosphine) palladium(0) (0.2 g) were stirred in dimethoxy ethane (30 mL) at room temperature under nitrogen. After 15 min., (1,4-dihydro-4,4-dimethyl-2-oxo-2H-3,1-benzoxazin-6-yl)boronic acid (1.1 g, 5.0 mmol) and sodium carbonate (1.35 g) in water (10 mL) were added and the mixture heated under reflux. After 16 h., the mixture was cooled, partitioned between water and EtOAc, the organic layer was washed with sat. sodium carbonate solution, brine, dried (MgSO4) and evaporated. The residue was then dissolved in acetonitrile (50 mL), treated with copper acetate (0.2 g) and heated under reflux. After 16 h, the mixture was cooled and evaporated. The residue was partitioned between water and EtOAc, the organic layer was then washed with dilute sulfuric acid (1N), water, brine, dried (MgSO$_4$) and evaporated. The residue was then subjected to column chromatography (SiO$_2$, EtOAc/hexane, gradient elution), and then crystallized from EtOAc-hexane to afford the title compound (0.176 g, 0.59 mmol, 17%) as a white solid: mp. 192–198° C.; $^1$H-NMR (CDCl$_3$) δ9.15 (s, 1H), 7.69–7.58 (m, 2H), 7.42–7.31 (m, 3H), 6.99 (d, 1H, J=8.2 Hz), 1.78 (s, 6H); MS ((+)ESI) 297 [M+H]$^+$.

EXAMPLE 121

Pharmacology

The compounds of this invention were tested in the relevant assay as described below and their potency are in the range of 0.01 nM to 5 μM in the in vitro assays and 0.001 to 300 mg/kg in the in vivo assays.

TABLE 1

Potency of the selected cyclocarbamate derivatives as PR antagonists in some in vitro and in vivo models:

| Compound | R$_1$ | R$_2$ | R$_3$ | hPR Decidualization IC$_{50}$ (nM) | CV-1 IC$_{50}$ (mg/kg) |
|---|---|---|---|---|---|
| 1 | 3-cyano-4-fluorophenyl | Me | Me | 55 | 80%@1** |
| 2 | 3-fluoro-5-trifluormethyl-phenyl | Me | Me | 54 | 50%@1 |
| 3 | 3-fluorophenyl | Me | Me | 6 | 80%@3 |
| 4 | 3,5-dichloro-phenyl | Me | Me | 134 | 60%@1 |
| 5 | 5-cyano-2-fluorophenyl | Me | Me | 68 | 60%@1 |
| 6 | 3-fluoro-5-nitrophenyl | Me | Me | 11.5 | 50%@1 |
| 7 | 4-(2-cyano-furyl) | Me | Me | 30 | 75%@3 |
| 8 | 3-bromo-5-fluorophenyl | Me | Me | 11 | 50%@3 |
| 9 | 3-cyano-4-fluorophenyl | Me | Me | 13 | 6.96 ± 10.84 |
| 10 | 5-(2-cyano-4-methylthiophenyl) | spirocyclohexyl | | 2.7 | 50%@10 |

TABLE 1-continued

Potency of the selected cyclocarbamate derivatives as PR antagonists in some in vitro and in vivo models:

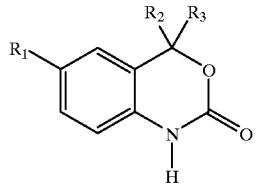

| Compound | $R_1$ | $R_2$ | $R_3$ | hPR Decidualization $IC_{50}$ (nM) | CV-1 $IC_{50}$ (mg/kg) |
|---|---|---|---|---|---|
| 11 | 5-(2-cyanothio-phenyl) | spirocyclohexyl | | 12 | 50%@10 |
| 12 | 5-(2-cyanothio-phenyl) | Me | Me | 19 | 3.34 ± 0.22 |
| 13 | 3-bromophenyl | Me | Me | 11.5 | 3 |
| 14 | 3-chloro-5-fluoro-phenyl | Me | Me | 22 | 50%@3 |
| 15 | 3-cyano-5-fluoro-phenyl | cyclopropyl | cyclopropyl | 22 | 3 |
| 16 | 5-(3-bromo-pyridyl) | Me | Me | 26 | 50%@3 |
| 17 | 4-(2-cyanothio-phenyl) | Me | Me | 12.7 | 2.3 ± 0.46 |
| 18 | 5-(2-cyano-4-methylthiophenyl) | Me | Me | 5.23 | 1.5 |
| 19 | 3-cyano-5-fluoro-phenyl | Me | Me | 13.8 | 0.35 |
| 20 | 3-chloro-4-fluoro-phenyl | Me | Me | 37 | 1 |

ND, not determined;
**Percentage inhibition at the dose specified

A. In-vitro biology

The in-vitro biology is determined by (1) competitive Radioligand Binding: using the A-form of the human progesterone receptor with progesterone as the radioligand; (2) co-transfection assay, which provides functional activity expressed as agonist EC50 and Antagonist IC50 values; (3) a T47D cell proliferation, which is a further functional assay which also provides agonist and antagonist data; and (4) T47D cell alkaline phosphatase assay, which is a further functional assay which also provides agonist and antagonist data.

1. hPR Binding Assay

This assay is carried out in accordance with: Pathirana, C.; Stein, R. B.; Berger, T. S.; Fenical, W.; Ianiro, T.; Mais, D. E.; Torres, A.; Glodman, M. E., Nonsteroidal human progesterone receptor modulators from the marine alga cymoplia barbata, J. Steroid Biochem. Mol. Biol., 1992, 41, 733–738.

2. PRE-luciferase Assay in CV-1 Cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium

The growth medium was as follows: DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (BioWhittaker), phenol red-free, containing 10% (v/v) charcoal-stripped fetal bovine serum (heat-inactivated), 0.1 mM MEM non-essential amino acids, 100 U/ml penicillin, 100mg/ml streptomycin, and 2 mM GlutaMax (GIBCO, BRL).

b. Cell Culture, Transfection, Treatment, and Luciferase Assay

Stock CV-1 cells are maintained in growth medium. Co-transfection is done using $1.2 \times 10^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in full dose- response curves and the $EC_{50}$ or $IC_{50}$ values are calculated.

TABLE 2

Estimated $EC_{50}$, standard error (SE), and 95% confidence intervals (CI) for reference progestins from three individual studies

| Compound | Exp. | EC50 (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 3

Estimated $IC_{50}$, standard error (SE), and 95% confident interval (CI) for the antiprogestin, RU486 from three individual studies

| Compound | Exp. | IC 50 (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

3. T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium

DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

b. Treatment Medium

Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture

Stock T47 D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in fall dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 $\mu$l of 1 M sulfuric acid is added to each well to stop color reaction and optical density is read in a plate reader at 450 nm within 5 min.

e. Analysis of Results

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds

Trimegestone and medroxyprogesterone acetate (MPA) are reference progestins and RU486 is the reference antiprogestin. All reference compounds are run in full dose-response curves and the $EC_{50}$ or $IC_{50}$ values are calculated.

TABLE 4

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
|  | 2 | 0.014 | 0.001 | 0.011 | 0.017 |
|  | 3 | 0.019 | 0.001 | 0.016 | 0.024 |
| MPA | 1 | 0.019 | 0.001 | 0.013 | 0.027 |
|  | 2 | 0.017 | 0.001 | 0.011 | 0.024 |

TABLE 5

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE 4. T47D Cell Alkaline Phosphatase Assay The purpose of this assay is to identify progestins or antiprogestins by determining a compound's effect on alkaline phosphatase activity in T47D cells. The materials and methods used in this assay are as follows.

a. Culture Medium

DMEM:F12 (1:1) (GIBCO, BRL) supplemented with 5% (v/v) charcoal stripped fetal bovine serum (not heat-inactivated), 100 U/ml penicillin, 100 µg/ml streptomycin, and 2 mM GlutaMax (GIBCO, BRL).

b. Alkaline Phosphatase Assay Buffer

I. 0.1 M Tris-HCl, pH 9.8, containing 0.2% Triton X-100

II. 0.1 M Tris-HCl, pH 9.8 containing 4 mM p-nitrophenyl phosphate (Sigma).

c. Cell Culture and Treatment

Frozen T47D cells were thawed in a 37° C. water bath and diluted to 280,000 cells/ml in culture medium. To each well in a 96-well plate (Falcon, Becton Dickinson Labware), 180 µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

d. Alkaline Phosphatase Enzyme Assay

At the end of treatment, the medium was removed from the plate and fifty µl of assay buffer I was added to each well. The plates were shaken in a titer plate shaker for 15 min. Then 150 µl of assay buffer II was added to each well. Optical density measurements were taken at 5 min intervals for 30 min at a test wavelength of 405 nM.

e. Analysis of Results: Analysis of Dose-response Data

For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds

Progesterone and trimegestone are reference progestins and RU486 is the reference antiprogestin. All reference compounds are run in full dose response curves and the $EC_{50}$ or $IC_{50}$ values are calculated.

TABLE 6

Estimated $EC_{50}$, standard error (SE), and 95% confidence intervals (CI) for reference progestins from three independent experiments

| Compound | Exp. | EC50 (nM) | SE | 95% CI lower | 95% CI upper |
|---|---|---|---|---|---|
| Progesterone | 1 | 0.839 | 0.030 | 0.706 | 0.996 |
|  | 2 | 0.639 | 0.006 | 0.611 | 0.669 |
|  | 3 | 1.286 | 0.029 | 1.158 | 1.429 |
| Trimegestone | 1 | 0.084 | 0.002 | 0.076 | 0.091 |
|  | 2 | 0.076 | 0.001 | 0.072 | 0.080 |
|  | 3 | 0.160 | 0.004 | 0.141 | 0.181 |

TABLE 7

Estimated $IC_{50}$, standard error, and 95% confident interval for the reference antiprogestin RU486 from three independent experiments

| Compound | Exp | IC 50 (nM) | SE | 95% CI lower | 95% CI upper |
|---|---|---|---|---|---|
| RU486 | 1 | 0.103 | 0.002 | 0.092 | 0.115 |
|  | 2 | 0.120 | 0.001 | 0.115 | 0.126 |
|  | 3 | 0.094 | 0.007 | 0.066 | 0.134 |

B. In-vivo Biology

The primary in-vivo assay is the rat decidualization model which may be used to determine progestational effects of both agonists and antagonists. The secondary in-vivo assay is the rat ovulation inhibition model which is under development and hence the protocol is un-available.

1. Rat Decidualization Assay

The objective of this procedure is used to evaluate the effect of progestins and antiprogestins on rat uterine decidualization and compare the relative potencies of various test compounds. The materials and methods used in this assay are as follows.

a. Methods

Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC protocol #5002)

Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg . . . ).

e. Decidual Induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds

All progestin reference compounds were run in full dose-response curves and the $EC_{50}$ for uterine wet weight were calculated.

TABLE 8

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
|  | 2 | 6.21 | 1.12 | 4.41 | 8.76 |
| 3-Ketodesogestrel | 1 | 0.11 | 0.02 | 0.07 | 0.16 |
|  | 2 | 0.10 | 0.05 | 0.11 | 0.25 |
|  | 3 | 0.06 | 0.03 | 0.03 | 0.14 |
| Levonorgestrel | 1 | 0.08 | 0.03 | 0.04 | 0.16 |
|  | 2 | 0.12 | 0.02 | 0.09 | 0.17 |
|  | 3 | 0.09 | 0.02 | 0.06 | 0.13 |
|  | 4 | 0.09 | 0.02 | 0.06 | 0.14 |
| MPA | 1 | 0.42 | 0.03 | 0.29 | 0.60 |
|  | 2 | 0.39 | 0.05 | 0.22 | 0.67 |
|  | 3 | 0.39 | 0.04 | 0.25 | 0.61 |

TABLE 9

Estimated average $EC_{50}$, standard error, and 95% confidence intervals for dose-response curves of 3 reference compounds

| Compound | EC50 (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 10

Estimated $IC_{50}$, standard error, and 95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: [(D-C)/C]×100%

Progestational activity: Compounds that induce decidualization significantly (p<0.05) compared to vehicle control are considered active Antiprogestational activity: Compounds that decrease $EC_{50}$ progesterone induced decidualization significantly (p<0.05)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

EXAMPLE 122

6-(3-Methoxyphenyl)spiro[4H-3,1-benzoxazine 4,1-cyclobutan]-2(1H)-one

A solution of Boc protected 4-chloroaniline (1.15 g, 5 mmol) in anhydrous THF was treated at −78° C. under a blanket of nitrogen with t-butyllithium (7.4 mL, 12.5 mmol). The reaction solution was then slowly warmed to −20° C., kept stirring for 1.5 hours, and treated with cyclobutanone (1 mL, 13.4 mmol). The mixture was warmed to rt and quenched with brine (30 mL) and 1N aqueous hydrogen chloride solution (10 mL) was added Ethyl acetate was added and the organic layer was separated and dried ($MgSO_4$). After removal of the solvent, the residue was purified by flash column chromatography (hexane:ethyl acetate/3:1) to give the alcohol which was used in next step without further purification.

To a solution of above product in ethanol was added potassium hydroxide (2 g). The reaction mixture was stirred at rt for 18 hours, followed by the addition of brine (20 mL) and a cold 1N aqueous hydrogen chloride solution (20 mL). The precipitate was collected on a filter and washed with water to afford 6-chlorospiro[4H-3,1-benzoxazine-4,1-cyclobutan]-2(1H)-one as a white solid (0.1 3 g, 12% for two steps): mp 183–184° C.; MS (ESI) m/z 222 [M−H]−.

A mixture of 6-chlorospiro[4H-3,1-benzoxazine-4,1-cyclobutan]-2(1H)-one (0.1 g, 0.45 mmol), 3-methoxyphenyl boronic acid (0.1 g, 0.66mmol), [1,1'-bis(diphenylphosphino)ferrocene]dichloronickel (II) (50 mg, 0.073 mmol), potassium phosphate (0.35 g, 1.7 mmol) in dioxane (5 mL) was degassed to remove oxygen and then heated at 85° C. under a blanket of nitrogen for 72 hours. The reaction mixture was allowed to cool to rt. Ethyl acetate (30 mL) and brine (20 mL) were added. The organic layer was separated and dried ($MgSO_4$). After removal of solvent, the residue was purified through a column chromatography (hexane:ethyl acetate/3:1) to yield 6-(3-methoxy-phenyl)spiro[4H-3,1-benzoxazine-4,1-cyclobutan]-2(1H)-one as white solid (18 mg, 14%): mp 145–146° C.; $^1$H-NMR (DMSO-$d_6$) δ8.04 (s, 1H), 7.69 (d, 1H, J=1.6 Hz), 7.59 (dd, 1H, J=8.2, 1.5 Hz), 7.36 (d, 1H, J=7.9 Hz), 7.27 (d, 1H, J=7.7 Hz), 7.22 (d, 1H, J=2.2 Hz), 6.99 (d, 1H, J=8.2 Hz), 6.92 (dd, 1H, J=8.0, 2.4 Hz), 3.83 (s, 3H), 2.45–2.62(m, 4H), 1.81–2.12 (m, 2H) ); MS ((+)APCI) m/z 296 [M+H]+.

EXAMPLE 123

8-Bromo-6-(3-chloro-4-fluorophenyl)-4,4-dimethyl-1,4-dihydro-2H-3,1-benzoxazin-2-one To a mixture of 6-(3-chloro-4-fluorophenyl)-4,4-dimethyl-1,4-dihydro-2H-3,1-benzoxazin-2-one (0.2 g, 0.65 mmol) and sodium acetate (0.1 g, 1.2 mmol) in acetic acid (5 mL) was added, at rt under nitrogen bromine (0.04 mL, 0.78 mmol). The reaction mixture was stirred for 20 hours and poured into ice water (30 mL). The precipitate was collected on a filter and washed with water (3×5 mL) to yield 8-bromo-6-(3-chloro-4-fluorophenyl)-4,4-dimethyl-1,4-dihydro-2H-3,1-benzoxazin-2-one as off-white solid (0.18, 72%): mp 194–195° C.; $^1$H-NMR (DMSO-d$_6$) δ9.77 (s, 1H), 8.02 (dd, 1H, J=7.10, 1.81 Hz), 7.92 (s, 1H), 7.77 (m, 1H), 7.66 (s, 1H), 7.47–7.53 (m, 1H), 1.71 (s, 6H). MS (ESI) m/z 384, 386 [M−H]$^-$.

EXAMPLE 124

3-(8-Bromo4,4-dimethyl-2-oxo-1,4-dihydro-2H-3,1-benzoxazin-6-yl)-5-fluorobenzonitrile Prepared according to the above procedure from 3-(4,4-dimethyl-2-oxo-1,4-dihydro-2H-3,1-benzoxazin-6-yl)-5-fluorobenzonitrile (0.5 g, 1.7 mmol) as an off-white solid (0.48 g, 75%): mp 216–217° C.; $^1$H-NMR (DMSO-d$_6$) δ9.78 (s, 1H), 8.18 (t, 1H, J=1.6 Hz), 8.02–8.08 (m, 2H), 7.81 (m, 1H), 7.75 (d, 1H, J=1.8 Hz), 1.66 (s, 6H). MS (ESI) m/z 373, 375 [M−H]$^-$.

EXAMPLE 125

5-(8-Bromo-4,4-dimethyl-2-oxo-1,4-dihydro-2H-3,1-benzoxazin-6-yl)-2-fluorobenzonitrile Prepared according to the above procedure from 5-(4,4-dimethyl-2-oxo-1,4-dihydro-2H-3,1-benzoxazin-6-yl)-2-fluorobenzonitrile (0.2 g, 0.67 mmol) as an off-white solid (0.18 g, 72%): mp 235–236° C.; $^1$H-NMR (DMSO-d$_6$) δ9.78 (s, 1H), 8.38 (dd, 1H, J=6.1, 2.4 Hz), 8.14–8.20 (m, 1H), 7.98 (d, 1H, J=1.9 Hz), 7.71 (d, 1H, J=1.8 Hz), 7.62 (t, 1H, J=9.1 Hz), 1.69 (s, 6H). MS (ESI) m/z 373, 375 [M−H]$^-$.

EXAMPLE 126

6-(3-Bromophenyl)-1,4,4-trimethyl-1,4-dihydro-2H-3,1-benzoxazin-2-one

To a solution of 6-(3-bromophenyl)-4,4-dimethyl-1,4-dihydro-2H-3,1-benzoxazin-2-one (1 g, 3.0 mmol) in anhydrous DMF was added, at rt under a blanket of nitrogen, sodium hydride (60% in mineral oil, 0.24 g, 6.0 mmol). After stirring for 20 minutes, the reaction solution was treated with iodomethane and stirred for 1.5 hours. The mixture was poured into a saturated aqueous ammonium sulfate solution (40 mL) and ethyl acetate (40 mL) was added. The organic layer was separated, dried (MgSO$_4$), and evaporated to yield 6-(3-bromophenyl)-1,4,4-trimethyl-1,4-dihydro-2H-3,1-benzoxazin-2-one as off-white solid (0.75 g, 72%): mp 142–143° C.; $^1$H-NMR (DMSO-d$_6$) δ7.93 (s, 1H), 7.71 (m, 1H), 7.65 (s, 1H), 7.55 (d, 1H, J=8.0 Hz), 7.42 (t 1H, J=7.7 Hz), 7.18 (d, 1H, J=8.4 Hz), 3.35 (s, 3H), 1.67 (s, 6H). MS (ESI) m/z 368, 370 [M+Na]$^+$.

EXAMPLE 127

6-(3-Fluorophenyl)4-methyl-1,4-dihydro-2H-3,1-benzoxazin-2-one

4-Amino-3'-fluoro[1,1'-biphenyl]-3-carbonitrile was prepared from 3-fluorophenyl boronic acid and 2-amino-5-bromobenzonitrile according to procedure A. A solution of 4-amino-3'-fluoro[1,1'-biphenyl]-3-carbonitrile (6.65 g, 31.3 mmol) in anhydrous THF (100 mL) was treated drop wise at rt under nitrogen with methylmagnesium bromide (3.0 M in ether, 21 mL, 63 mmol). After addition, the reaction mixture was heated at gentle reflux for 1.5 hours, cooled to rt, and treated with 3N aqueous hydrogen chloride solution (30 mL). The mixture was heated at reflux for 3 hours, cooled to ambient temperature, and adjusted to pH 5–6 by addition of a saturated aqueous sodium carbonate solution. Ethyl acetate (100 mL) was added, organic layer was separated and aqueous layer was extracted with ethyl acetate (3×50 mL). The combined organic layers were dried (MgSO$_4$) and evaporated. The residue was purified by a silica gel column chromatography (hexane:ethyl acetate/3:1) to afford 1-(4-amino-3'-fluoro[1,1'-biphenyl]-3-yl)ethanone (3.1 g, 43%): mp 156–157° C.

A solution of 1-(4-amino-3'-fluoro[1,1'-biphenyl]-3-yl)ethanone (3 g, 13 mmol) in anhydrous methanol (60 mL) was treated at rt under nitrogen with sodium borohydride in a portion wise manner. After addition, the reaction mixture was stirred for 4 hours, treated with a saturated aqueous ammonium sulfate solution (50 mL) and ethyl acetate (100 mL). The organic layer was separated, dried (MgSO$_4$) and evaporated. The residue was purified on a silica gel column chromatography (hexane:ethyl acetate/3:1) to yield 1-(4-amino-3'-fluoro[1,1'-biphenyl]-3-yl)ethanol as a white solid (2 g, 67%): mp 136–137° C.

A mixture of above alcohol (0.2 g, 0.87 mmol) and triphosgene in anhydrous THF (20 mL) was stirred at rt under nitrogen. After 15 minutes, the mixture was treated with a saturated aqueous sodium bicarbonate solution (30 mL) and ethyl acetate (40 mL). The organic layer was separated, dried (MgSO$_4$), and evaporated to give 6-(3-fluorophenyl)4-methyl-1,4-dihydro-2H-3,1-benzoxazin-2-one as a white solid (0.18 g, 81%): mp 160–161° C.; $^1$H-NMR (DMSO-d$_6$) δ10.31 (s, 1H), 7.62 (dd, 1H, J=8.2, 1.9 Hz), 7.57 (s, 1H), 7.44–7.53 (m, 3H), 7.13–7.20 (m 1H), 6.97 (d, 1H, J=8.2 Hz), 5.57 (q, 1H, J=6.6 Hz), 1.63 (d, 3H, J=6.6 Hz). MS (ESI) m/z 256 [M−H]$^-$.

EXAMPLE 128

3-(4,4-Dimethyl-8-methoxy-2-oxo-1,4-dihydro-2H-3,1-benzoxazin-6-yl)-5-fluorobenzonitrile To a solution of 2-amino-3-methoxybenzoic acid (5 g, 30 mmol) in anhydrous THF (100 mL) was added at ambient temperature under a blanket of nitrogen methylmagnesium bromide (3.0 M in THF, 50 mL, 150 mmol). The reaction mixture was heated at 50° C. for 18 hours, cooled to rt, and treated with a saturated aqueous ammonium chloride solution (50 mL). Ethyl acetate (100 mL) was added and organic layer was separated, dried (MgSO$_4$), and evaporated. The residue was dissolved in anhydrous THF (100 mL) and treated at ambient temperature under nitrogen with 1,1'-carbonyldiimidazole (5.4 g, 33 mmol). After 24 hours, the mixture was quenched with 1N aqueous hydrogen chloride solution (30 mL). Ethyl acetate (100 mL) was added, organic layer was separated, dried (MgSO$_4$), and evaporated. The residue was purified by a silica gel column chromatography (hexane:ethyl acetate/3:1) to afford 8-methoxy-4,4-dimethyl-1,4-dihydro-2H-3,1-benzoxazin-2-one as white solid (3.5 g, 56%): MS (ESI) m/z 208 [M+H]$^+$.

To a mixture of 8-methoxy-4,4-dimethyl-1,4-dihydro-2H-3,1-benzoxazin-2-one (2.1 g, 10.1 mmol), sodium acetate (1.5 g, 18 mmol) in acetic acid (30 mL) was added bromine (0.62 mL, 12 mmol) at ambient temperature. After 30 minutes, the solution was treated with a concentrated ammonium hydroxide solution (50 mL). The precipitate was collected on a filter and washed with water (3×20 mL) to yield 6-bromo-8-methoxy-4,4-dimethyl-1,4-dihydro-2H-3,1-benzoxazin-2-one (2.7 g, 93%) as off-white solid: MS (ESI) m/z 286, 288 [M+H]$^{30}$.

A mixture of 6-bromo-8-methoxy-4,4-dimethyl-1,4-dihydro-2H-3,1-benzoxazin-2-one (1.6 g, 5.6 mmol), bis (pinacolato)diboron (1.6 g, 6.3 mmol), potassium acetate (1.5 g, 15.3 mmol), and [1,1'-bis(diphenylphosphino)ferrocene]palladium (II) chloride (1:1 complex with methylene chloride, 0.5 g, 0.6 mmol) in DMF (30 mL) was subject to a positive flow of nitrogen to remove oxygen and then heated at 85° C. under a blanket of nitrogen for 18 hours. The reaction mixture was allowed to cool to ambient temperature, treated with 3-bromo-5-fluoro-benzonitrile (1.2 g, 6 mmol), [1,1'-bis(diphenylphosphino)ferrocene] palladium (II) chloride (1:1 complex with methylene chloride, 0.5 g, 0.6 mmol), and sodium carbonate (2 g, 19 mmol) in water (10 mL). The resulted solution was heated at 85° C. for 3 hours under a blanket of nitrogen, cooled to rt, and treated with brine (50 mL). Ethyl acetate (100 mL) was added, organic layer was separated, dried ($MgSO_4$), and evaporated. The residue was purified by a flash silica gel column chromatography (THF:hexane/2:3) to yield 3-(4,4-dimethyl-8-methoxy-2-oxo-1,4-dihydro-2H-3,1-benzoxazin-6-yl)-5-fluorobenzonitrile as a white solid (0.6 g, 33%): mp 252–253° C.; $^1$H-NMR (DMSO-$d_6$) δ9.76 (s, 1H), 8.21 (s, 1H), 8.07 (d, 1H, J=10.6 Hz), 7.82 (m,1H), 7.39 (s 1H), 7.36 (s, 1H), 3.93 (s, 3H), 1.66 (s, 6H). MS (ESI) m/z 325 [M−H]$^-$.

EXAMPLE 129

3-(4,4-Dimethyl-8-hydroxy-2-oxo-1,4-dihydro-2H-3,1-benzoxazin-6-yl)-5-fluorobenzonitrile A mixture of 3-(4,4-dimethyl-8-methoxy-2-oxo-1,4-dihydro-2H-3,1-benzoxazin-6-yl)-5-fluorobenzonitrile (0.1 g, 0.31 mmol), Lithium iodide (0.3 g, 2.24 mmol) in 2,4,6-collidine was heated at reflux under nitrogen for 5 hours. The solvent was removed in vacuo and the residue was taken in a mixture of brine (10 mL) and ethyl acetate (30 mL). The organic layer was separated, dried ($MgSO_4$), and evaporated. The resultant residue was purified on a silica gel column chromatography (hexane:ethyl acetate/1:1) to give the title compound as white plates (0.03 mg, 31%): mp 197–198° C.; $^1$H-NMR (DMSO-$d_6$) δ10.16 (s, 1H), 9.55 (s, 1H), 8.01 (s, 1H), 7.79–7.87 (m, 2H), 7.20 (s,1H), 7.08 (d, 1H, J=1.0 Hz), 1.65 (s, 6H). MS (ESI) m/z 311 [M−H]$^-$.

EXAMPLE 130

6-(2,3-Difluoro-phenyl)-4,4-dimethyl-1,4-dihydro-benzo[d][1,3]oxazin-2-one

Prepared according to procedure B from (1,4-dihydro-4,4-dimethyl-2-oxo-2H-3,1-benzoxazin-6-yl)boronic acid and 2,3-difluorobenzyltriflate. A yellow solid: mp 166–167° C.; $^1$H-NMR (DMSO-$d_6$) δ10.4 (s, 1H), 7.5–7.2 (m, 5H), 7.0 (m, 1H), 1.7 (s, 6H); MS (EI) m/z 289 ([M+H]$^+$); Anal. Calc. For $C_{16}H_{13}F_2NO_2$: C, 66.43, H, 4.53, N, 4.84. Found: C, 66.15, H, 4.37, N, 4.64.

EXAMPLE 131

3-(1-Ethyl-4,4-dimethyl-2-oxo-1,4-dihydro-2H-benzo[d][1,3]oxazin-6-yl)-5-fluoro-benzonitrile Prepared according to the procedure for example 125 from 3-(4,4-dimethyl-2-oxo-1,4-dihydro-2H-benzo[d][1,3]oxazin-6-yl)-5-fluoro-benzonitrile. A white solid: mp 154–155° C.; $^1$H-NMR (DMSO-$d_6$) δ8.17 (s, 1H), 8.03 (d, 1H, J=10.5 Hz), 7.84–7.77 (m, 3H), 7.27 (d, 1H, J=8.54 Hz), 3.97 (q, 2H, J=6.89 Hz), 1.67 (s, 6H), 1.21 (t, 3H, J=6.95 Hz); MS (EI) m/z 324 ([M+H]$^+$); Anal. Calc. For $C_{19}H_{17}FN_2O_2$: C, 70.36, H, 5.28, N, 8.64. Found: C, 70.33, H, 5.51, N, 8.48.

EXAMPLE 132

[6-(4,4-dimethyl-2-oxo-1,4-dihydro-2H-3,1-benzoxazin-6-yl)pyridin-2-yl]acetonitrile Prepared according to procedure B from (1,4-dihydro-4,4-dimethyl-2-oxo-2H-3,1-benzoxazin-6-yl)boronic acid and (6-bromo-2-pyridyl)acetonitrile (J. Org. Chem. 1988, 53, 786–790). An off-white solid, mp 210–212.5° C. $^1$H NMR (DMSO-$d_6$) □1.68 (s, 6H), 4.27 (s, 2H), 7.00 (d, 1H, J=8.3 Hz), 7.34 (d, 1H, J=7.1 Hz), 7.89–7.96 (m, 2H), 8.00–8.05 (m, 2H), 10.42 (s, 1H). MS (ESI) [M−H]$^-$=292. Anal. calcd. for $C_{17}H_{15}N_3O_2$: C, 69.61; H, 5.15; N, 14.33. Found: C, 68.49; H, 5.19; N, 13.74.

EXAMPLE 133

3-(4,4-Dimethyl-2-oxo-1,4-dihydro-2H-benzo[d][1,3]-oxazin-6-yl)-5-fluoro-phenylacetonitrile To a solution of 3-bromo-5-fluorobenzaldehyde(22.25 g, 0.11 mole) in methanol at rt was added $NaBH_4$,(2.07 g, 0.055 mole) stirred at rt for 2 hr. The reaction was quenched with $H_2O$, and concentrated. The residue was diluted with diethyl ether, washed with 1 N HCl, brine, dried over $MgSO_4$, concentrated. 3-Bromo-5-fluorobenzyl alcohol as a colorless oil was collected (14.6 g, 65%). $^1$H NMR (DMSO-$d_6$) δ4.50 (m, 2H), 5.44(t, 3H, J=5.93 Hz), 7.16 (dd, 1H, J=1.09, 8.79Hz), 7.36( s, 1H), 7.38 (dd, 1H, J=2.99, 6.15Hz); Anal. Calc. For $C_7H_6Br_2FO$: C, 41.01, H, 2.95. Found: C, 41.30, H, 3.01.

To a solution of 3-Bromo-5-fluorobenzyl alcohol (2.3 g, 0.011 mole) in $CH_2Cl_2$ (15 mL) was added 12.4 mL of 1.0M $PBr_3$ (3.33 g, 0.0123 mole) in $CH_2Cl_2$, stirred for 3 hr, diluted with ether (100 mL), washed with $H_2O$ (50 ml,3×), dried over $MgSO_4$, concentrated. Purified by column chromatography using 1:9 ethyl acetate/hexane as an eluant solvent system. 3-Bromo-5-fluorobenzyl bromide as a white crystalline material was obtained, mp 41–43° C. $^1$H NMR (DMSO-$d_6$) □4.69 (s, 2H), 7.52( d, 1H, J=1.76 Hz) 7.54(d, 1H, J=1.91 Hz), 7.56( s, 1H); MS( EI): M+. m/z 266; Anal. Calc. For $C_7H_5Br_2F$: C, 31.38, H, 1.88. Found: C, 31.75, H, 1.78.

To a solution of 3-bromo-5-fluorobenzyl bromide (3.2 g, 0.0112 mole) in 1,4-dioxane (20 mL) was added a solution of KCN (0.82 g, 0.013 mole) in $H_2O$ (5 mL) and EtOH (5 mL), refluxed for 2 hours. Extracted with ether, washed with brine, dried over $MgSO_4$, concentrated. Column chromatography using hexane/ethyl acetate (19:1). 3-Bromo-5-fluorophenylacetonitrile obtained was a colorless oil: $^1$H NMR (DMSO-$d_6$) d 4.15 ( s, 2H), 7.29( d, 1H, J=9.37 Hz), 7.47(s, 1H), 7.55(d, 1H, J=8.45 Hz); MS( EI) M+m/z 213; Anal. Calc. For $C_8H_5BrFN$: C, 44.89, H, 2.35, N,6.54. Found: C, 44.88, H, 2.32, N, 6.46.

The title compound was prepared according to the procedure B from 3-bromo-5-fluorophenylacetonitrile and (1,4-dihydro-4,4-dimethyl-2-oxo-2H-3,1-benzoxazin-6-yl) boronic acid. A white solid was obtained and recrystallized from ethanol/ether: mp 218–220. $^1$H NMR (DMSO-$d_6$) □1.67 ( s, 6H), 4.11( s, 2H ), 6.98(d, 1H, J=8.92 Hz), 7.18( d, 1H, J=9.26), 7.52–7.62( m, 3H), 10.37( s, 1H); MS(EI) (M−H)_ m/z 309; Anal. Calcd. For $C_{18}H_{15}FN_2O_2$: C, 69.67, H, 4.87, N, 9.03. Found: C, 69.78, H, 4.97, N, 8.36.

EXAMPLE 134

3-(4,4-Dimethyl-2-oxo-1,4-dihydro-2H-benzo[d][1,3]-oxazin-6-yl)-4-fluoro-phenylacetonitrile To a solution of 5-bromo-2-fluorotoluene (15 g, 0.079 mole) in $CCl_4$ (150 mL) was added NBS (14.2 g, 0.080 mole). The resulting reaction solution was heated under reflux with the starting material being completely consumed within 2 hr. CCl$_4$ was removed under reduced pressure and the residue was diluted dissolved in ether, washed with brine (3×), dried over MgSO$_4$, concentrated. Chromatographed/ hexane yielded 5-bromo-2-fluorobenzyl bromide. The product was immediately used for the reaction below.

5-Bromo-2-fluorobenzyl bromide (8.0 g, 0.03 mole) was dissolved in 1,4-Dioxane (60 mL) and added to a solution of KCN (2.04 g, 0.031 mole) in H$_2$O (20 mL) and ethanol ( 20 mL). The resulting mixture was heated under reflux for 5 h. After cooling to rt, the product was extracted with ether ( 200 mL), washed with brine, dried over MgSO$_4$, concentrated. Crystallized from ether/hexane to give 5-bromo-2-fluorophenylacetonitrile as a white crystalline material (5.6 g, 88%): mp 55–58° C.; $^1$H NMR (DMSO-d$_6$) □4.07 ( s, 2H), 7.29( t, 1H,J=9.23 Hz), 7.60–7.69( m, 2H); MS(EI) M+. m/z 213 ; Anal. Calc. For C$_8$H$_5$Br$_2$FN: C, 44.89, H, 2.35, N, 6.54. Found: C, 44.90, H, 2.24, N, 6.43.

The title compound was prepared from 5-Bromo-2-fluorophenylacetonitrile and ( 1,4-dihydro-4,4-dimethyl-2-oxo-2H-3,1-benzoxaxin-6-yl)boronic acid. White solid; mp 184–187° C; $^1$H NMR (DMSO-d$_6$) □1.67 ( s, 6H), 4.11 ( s, 2H ), 6.98(d, 1H, J=8.92 Hz), 7.36(t, 1H, J=9.13 Hz) 7.54 ( d, 2H, J=7.91 Hz), 7.67–7.75(m, 2H), 10.37( s, 1H); MS(EI) (M–H)$^-$ m/z 309; Anal. Calc. For C$_{18}$H$_{15}$FN$_2$O$_2$: C, 69.67, H, 4.87, N, 9.03. Found: C, 68.71, H, 4.80, N, 8.54.

EXAMPLE 135

4-(4,4-Dimethyl-2-oxo-1,4-dihydro-2H-benzo[d][1,3]oxazin-6-yl)-2-fluorophenylacetonitrile Prepared according to procedure B from 4-bromo-2-fluorophenylacetonitrile (T. Alessi A. H. P. U.S. Pat. No: 4,895,862) and (1,4-dihydro-4,4-dimethyl-2-oxo-2H-3,1-benzoxazin-6-yl)boronic acid. A grey solid; mp 253–256° C. $^1$HNMR(DMSO-d6) □10.35 (s,1H) 7.67–7.49(m,5H), 6.97 (d,1H; J=8.6 Hz) 4.09 (s,2H) (s,2H) 1.67(s,6H); MS [M–H]$^-$ m/z 309. Anal. Calc. For C$_{18}$H$_{15}$N$_2$FO$_2$.0.15H20: C,69.07, H, 4.93, N, 8.95. Found C,69.27, H 5.05, N, 8.50

EXAMPLE 136

2-(4,4-Dimethyl 2-oxo-1,4-dihydro-2H-benzo[d][1,3]-oxazin-6-yl)phenylacetonitrile Prepared according to procedure B from 2-bromophenylacetonitrile and (1,4-dihydro4,4-dimethyl-2-oxo-2H-3,1-benzoxazin-6-yl)boronic acid. White solid; mp 176–179° C.; $^1$H-NMR (DMSO-d6), δ10.31 (s, 1H), 7.53 (m, 1H), 7.48(m,2H), 7.22–7.32(m,3H), 6.98(d,1H; J=8.0 Hz), 3.90(s,2H), 1.64(s,6H). MS (+)APCI [M+H]$^+$m/z =293. Anal. Calc. For C$_{18}$H$_{16}$N$_2$O$_2$: C, 73.95, H, 5.52, N, 9.58. Found: C,73.51, H, 5.70, N, 9.39.

EXAMPLE 137

N-[4-(4,4-Dimethyl-2-oxo-1,4-dihydro-2H-3,1-benzoxazin-6-yl)-2-fluoro-phenyl]-acetamide Prepared according to procedure B from 4'-bromo-2'-fluoroacetanilide and (1,4-dihydro4,4-dimethyl-2-oxo-2H-3,1-benzoxazin-6-yl)boronic acid. Off white solid ; mp 245–247° C. $^1$H-NMR (DMSO-d6) δ10.3 (s,1H), 9.79 (s, 1H), 7.95 (t,1H; J=8.4 Hz), 7.56–7.63(m,3H), 7.47(dd,1H J=1.64, 8.47 Hz), 6.95(d,1H; J=8.9 Hz), 2.1(s, 3H), 1.67(s, 6H); MS+APCI [M+H]$^+$ m/z 329. Anal. Calc. For C$_{18}$H$_{17}$N$_2$FO$_3$: C, 65.85, H, 5.22, N, 8.53. Found: C,65.46, H,5.24, N,8.12.

EXAMPLE 138

6-(3-Fluoro-4-methoxy-phenyl)4,4-dimethyl-1,4-dihydro-benzo[d][1,3]oxazin-2-one

Prepared according to procedure B from 4-bromo-2-fluoroanisole and (1, 4-dihydro-4,4-dimethyl-2-oxo-2H-3,1-benzoxazin-6-yl)boronic acid. White solid: mp 210–211° C. $^1$H-NMR (DMSO-d6), δ10.27(s,1H), 7.52–7.60 (m,3H), 7.45(d,1H, J=8.6 Hz), 7.22 (t, 1H; J=8.9 Hz), 6.94(d,1H, J=8.8 Hz), 3.87(s,3H), 1.66(s, 6H). MS [M–H]$^-$m/z –300. Anal. Calc. For C$_{17}$H$_{16}$FNO$_3$: C, 67.76, H, 5.35, N, 4.65. Found: C,67.88, H,5.39, N, 4.70.

EXAMPLE 139

3-(4,4-Dimethyl-2-oxo-1,4-dihydro-2H-benzo[d][1,3]-oxazin-6-yl)phenylacetonitrile Prepared according to the procedure B from 3-bromophenylacetonitrile and (1,4-dihydro-4,4-dimethyl-2-oxo-2H-3,1-6-yl)boronic acid. White solid: mp 188–190° C. $^1$H-NMR (DMSO-d6) δ10.33(s, 1H), 7.62(m, 2H), 7.55 (m, 2H), 7.48 (d, 1H J=8.00 Hz), 7.33 (d, 1H, J=7.57 Hz), 6.99 (d,1H, J=8.81 Hz) 4.09 (s, 2H), 1.67 (s, 6H); MS m/z 291(M–H). Anal. Calc. For C$_{18}$H$_{16}$N$_2$O$_2$)2.0.3 H20: C,72.61, H, 5.62, N, 9.41. Found: C, 73.00, H,5.43, N, 8.81

EXAMPLE 140

3-(4,4-Dimethyl-2-oxo-1,4-dihydro-2H-benzo[d][1,3]-oxazin-6-y) benzenesulfonamide Prepared according to procedure B from 3-bromobenzenesulfonamide and (1,4-dihydro-4,4-dimethyl-2-oxo-2H-3,1-6-yl)boronic acid. White solid: mp 242–244° C. (dec) $^1$H-NMR (DMSO-d6) δ10.28(s, broad 1H), 8.07(s,1H), 7.9(d, 1H, J=7.80 Hz), 7.78 (d, 1H J=7.86 Hz), 7.64 (t, 1H, J=7.79 Hz), 7,59 (m, 2H), 7.42(s, broad 2H), 7.02(d, 1H, J=8.86 Hz), 1.68(s, 6H); MS m/z 331(M+H). Anal. Calc. For C$_{16}$H$_{16}$N$_2$O$_4$S): C,57.82, H, 4.85, N, 8.43. Found: C, 57.49, H,5.08, N, 8.05.

EXAMPLE 141

5-(4,4-Dimethyl-2-oxo-1,4-dihydro-2H-benzo[d][1,3]-oxazin-6-y)-thiophene-2-sulfonamide Prepared according to procedure B from 5-bromothiophene-2-sulphonamide and (1,4-dihydro4,4-dimethyl-2-oxo-2H-3,1-6-yl)boronic acid. White solid: mp 258–260° C, $_1$H-NMR (DMSO-d6) δ10.41(s,1H), 7.71(s, 2H), 7.58(m,2H), 7.52(d, 1H, J=3.9 Hz), 7.48(d, 1H J=8.16 Hz), 6.95(d, 1H J=8.16), 1.66(s,6H); MS m/z 337(M–H). Anal. Calc. For C$_{14}$H$_{14}$N$_2$O$_4$S$_2$): C,49.69, H, 4.17, N, 8.28. Found: C, 49.90, H, 4.28 N, 8.12.

EXAMPLE 142

6-(6-Amino-pyridin-3-yl)4,4-dimethyl-1,4-dihydro-benzo[d][1,3]oxazine-2-one

Prepared according to procedure B from 2-amino-5-bromopyridine and (1,4-dihydro-4,4-dimethyl-2-oxo-2H-3, 1-6-yl)boronic acid. White crystals, mp 257–259° C. $^1$H-NMR (DMSO-d6) δ10.20 (S,1H), 8.22 (d,1H, J=2.38 Hz) 7.69,7.66 (dd, 1H, J=2.5, 2.5 Hz), 7.42 (m,2H), 6.89 (d,1H, J=8.8 Hz), 6.49(d,1H, J=8.64 Hz), 6.02(s,2H), 1.64 (s,6H); MS m/z 269 M+. Anal. Calcd. For C$_{15}$H$_{15}$N$_3$O$_2$.17 H$_2$O: C, 66.15, H, 5.68, N, 15.43. Found: C, 66.10, H,5.81, N, 15.02.

EXAMPLE 143

6-(5-Diethoxymethyl-furan-3-yl)-4,4-dimethyl-1,4-dihydro-benzo[d][1.3]oxazin-2-one Prepared according to procedure B from 4,4-dimethyl 2 oxo-1, 4-dihydro 2 H-benzo[d][1,3]oxazine-6-boronic acid and 3-bromo-5-diethoxymeyhyl furan. A brown gum: $^1$H NMR (DMSO-d$_6$) δ10.2 (s, 1H), 8.12(s, 1H), 7.54–7.49 (m, 2H), 6.93–6.88(m, 2H), 5.56(s, 1H), 3.60–3.38(m, 4H), 1.67(s,6H), 1.2–1.14 (m, 6H). MS (ESI) m/z 344 [M–H]$^-$. Anal. Calcd. For $C_{19}H_{23}NO_5 \cdot \frac{1}{2}H_2O$: C, 64.39; H, 6.77; N, 3.95. Found C, 64.90; H, 6.79; N, 3.78.

EXAMPLE 144

4-(4,4-Dimethyl-2-oxo-1,4-dihydro-2H-benzo[d][1,3]oxazin-6-yl)-furan-2-carbaldehyde A solution of 6-(5-diethoxymethyl-furan-3-yl)-4,4-dimethyl-1,4-dihydro-benzo[d][1,3]oxazin-2-one (1.1 g, 3 mmol) was stirred in THF (20 mL) and 2N HCl (2 mL) for 1 hour. The crystalline product was filtered and dried (0.52 g, 69%): mp 262–263° C.; $^1$H NMR (DMSO-d$_6$) δ10.3 (s, 1H), 9.65 (s, 1H), 8.59 (s, 1H), 8.04 (s, 1H), 7.65–7.64 (d, 1H, J=1.5 Hz),7.61–7.60 (d, 1H, J=1.8 Hz), 7.59–7.58 (d, 1H, J=1.8 Hz), 6.94–6.91 (d, 1H, J=8.2 Hz), 1.65 (s, 6H). MS (ESI) m/z 270 [M–H]$^-$.

EXAMPLE 145

4-(1,4-Dihydro-4,4-dimethyl-2-oxo-2H-3,1-benzoxazin-6-yl)-2-furancarboxaldehyde oxime A mixture of 4-(4,4-dimethyl-2-oxo-1,4-dihydro-2H-benzo[d][1,3]oxazin-6-yl)-furan-2-carbaldehyde (2.7 g, 10 mmol), hydroxylamine hydrochloride (0.75 G, 10.6 mmol) and sodium acetate ( 0.87 g, 10.6 mmol) was heated at reflux in 80% ethanol (25 mL ) for 2 hours. The title compound crystallized from the cooled reaction mixture as tan crystals (1.5 g, 52.4%): mp 236–238° C. $^1$H NMR (DMSO-d$_6$) δ11.97(s, 1H), 10.26 (s, 1H), 8.2 (s, 1H), 7.63 (s, 1H), 7.56–7.52 (m, 3H), 6.91–6.88 (d, 1H, J=8.1 Hz), 1.66 (s, 6H ). MS ESI m/z 285 [M–H]$^-$. Anal. Calcd. For $C_{15}H_{14}N_2O_4$: C, 62.93; H, 4.93; N, 9.79. Found C, 62.77; H, 5.00; N, 9.79.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A method of treating hormone neoplastic disease in a mammal, wherein the hormone-dependent neoplastic disease is selected from the group consisting of uterine myometrial fibroids, endometriosis, benign prostatic hypertrophy, carcinomas and adenocarcinomas of the endometrium, ovary, breast, colon, prostate, pituitary, and meningioma, the method comprising administering to the mammal in need thereof about 0.5 to about 50 mg/kg of said mammal's body weight of a compound of formula I:

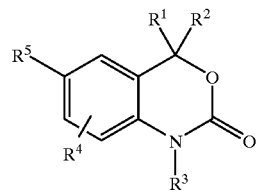

wherein:
$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$;

or $R^1$ and $R^2$ are fused to form:
  a) a carbon-based 3 to 8 membered saturated spirocyclic ring;
  b) a carbon-based 3 to 8 membered spirocyclic ring having in its backbone one or more carbon-carbon double bonds, or
  c) a carbon-based 3 to 8 membered heterocyclic ring having in its backbone one to three heteroatoms selected from the group consisting of O, S and N;
  the spirocyclic rings of a), b) and c) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl)$_2$;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is H, halogen, CN, $NO_2$, $C_1$ to $C_6$ alkyl, substituted $C_1$ to $C_6$ alkyl, alkynyl, substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is selected from the group consisting of (i) and (ii):
  (i) a substituted benzene ring having the substituents X, Y and Z as shown below:

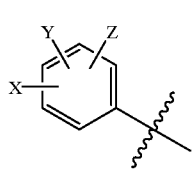

wherein:
X is selected from the group consisting of H, halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms selected from the group consisting of N, O, and S, $COR^D$, $OCOR^D$, and $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents selected from the group consisting of H, halogen, CN, $NO_2$, amino, aminoalkyl, $C_1$ to $C_3$ alkoxy, $C_1$ to $C_4$ alkyl, and $C_1$ to $C_3$ thioalkoxy;

wherein X, Y, and Z are not all H, (ii) a five or six membered ring having in its backbone 1, 2, or 3 heteroatoms selected from the group consisting of O, S, SO, $SO_2$ and $NR^6$ and containing one or two independent substituents selected from the group consisting of H, halogen, CN, $NO_2$, amino, $C_1$ to $C_4$ alkyl, $C_1$ to $C_3$ alkoxy, $C_1$ to $C_3$ aminoalkyl, $COR^F$, and $NR^GCOR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl:

$R^G$ is H, $C_1$ to $C_3$ alkyl, or substituted $C_1$ to $C_3$ alkyl;

$R^6$ is H, $C_1$ to $C_3$ alkyl, or $C_1$ to $C_4$ $CO_2$alkyl;

wherein when $R^5$ is a five-membered ring having in its backbone a $NR^6$ heteroatom, and when $R^5$ is attached at the two position of said ring, there is no CN substituent in the five position on said ring;

and wherein:

said substituted alkyl, alkenyl, and alkynyl groups have one to three substituents selected from the group consisting of halogen, CN, OH, $NO_2$, amino, aryl. heterocyclic, substituted aryl, substituted heterocyclic, alkoxy, aryloxy, substituted alkyloxy, alkylcarbonyl, alkylcarboxy, alkylamino, and arylthio;

said substituted alkoxy, aminoalkyl, and thioalkoxy groups have one to three substituents selected from the group consisting of alkyl and substituted alkyl;

said substituted aryl group has one to four substituents selected from the group consisting of halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio;

said substituted cycloalkyl group has one to three substituents selected from the group consisting of halogen, CN, OH, $NO_2$, amino, aryl, heterocyclic, aryloxy, aryl alkoxy, alkylcarbonyl, alkylcarboxy, alkylamino, and arylthio;

said substituted heterocyclic group has one to four substituents selected from the group consisting of halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio;

said substituted alkyloxy group has one to three substituents selected from the group consisting of halogen, CN, OH, $NO_2$, amino, aryl, heterocyclic, substituted aryl, substituted heterocyclic, alkoxy, aryloxy, alkylcarbonyl, alkylcarboxy, alkylamino, and arylthio;

said aryl group is selected from the group consisting of phenyl, naphthyl, biphenyl, anthryl, tetrahydronaphthyl, and phenanthryl;

said heterocyclic group is a five-membered ring, a six-membered ring. or a multicyclic ring;

said five-membered heterocyclic ring is selected from the group consisting of tetrahydrofuran, pyrrolidinyl, imidazolyl, oxazolyl, isoxazolyl, thienyl, furyl, and thiazolyl;

said six-membered heterocyclic ring is selected from the group consisting of piperidinyl, piperazinyl, 2-oxopiperidinyl, pyridyl, pyrazinyl, pyrimidinyl, pyridazinyl, thiamorpholinyl, azepinyl, and thiamorpholinyl sulfoxide;

said multicyclic heterocyclic ring is selected from the group consisting of indolyl, quinolinyl, benzofuranyl, benzothienyl, and isoquinolinyl;

or a pharmaceutically acceptable salt thereof.

2. The method according to claim 1, wherein:

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^5$ is (i) or (ii):

(i) the substituted benzene ring, wherein:

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring having in its backbone 1 to 3 heteroatoms selected from the group consisting of N, O, and S. $COR^D$, $OCOR^D$, and $NR^ECOR^D$;

Y and Z are independent substituents selected from the group consisting of H, halogen, CN, $NO_2$, $C_1$ to $C_3$ alkoxy, $C_1$ to $C_3$ alkyl, and $C_1$ to $C_3$ thioalkoxy; or (ii) the five or six membered ring, wherein said one or two independent substituents are selected from the group consisting of H, halogen, CN, $NO_2$, amino, $C_1$ to $C_3$ alkyl, and $C_1$ to $C_3$ alkoxy;

$R^6$ is H, or $C_1$ to $C_3$ alkyl.

3. The method according to claim 1, wherein:

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is (iii) or (iv):

(iii) the substituted benzene ring, wherein:

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring containing in its backbone 1 to 3 heteroatoms selected from the group consisting of N, O, and S, $COR^D$, $OCOR^D$, and $NR^E COR^D$;

Y and Z are independent substituents selected from the group consisting of H, halogen, CN, $NO_2$, $C_1$ to $C_3$ alkoxy, $C_1$ to $C_3$ alkyl, and $C_1$ to $C_3$ thioalkoxy; or (iv) the five or six membered ring, wherein said ring contains one or two independent substituents selected from the group consisting of H, halogen, CN, $NO_2$, amino, $C_1$ to $C_3$ alkyl, and $C_1$ to $C_3$ alkoxy;

$R^6$ is H, or $C_1$ to $C_3$ alkyl;

or pharmaceutically acceptable salt thereof.

4. The method according to claim 1, wherein:

$R^2$ and are selected from the group consisting of $C_1$ to $C_3$ alkyl and substituted $C_1$ to $C_3$ alkyl, or $R^1$ and $R^2$ are fused to form the carbon-based 3 to 6 membered saturated spirocyclic ring;

$R^2$ is H, OH, $NH_2$, $C_1$ to $C_6$ alkyl, substituted $C_1$ to $C_6$ alkyl, or $COR^C$;

$R^C$ is H, $C_1$ to $C_4$ alkyl, or $C_1$ to $C_4$ alkoxy;

$R^4$ is H, halogen, CN, $NO_2$, $C_1$ to $C_3$ alkyl, substituted $C_1$ to $C_3$ alkyl, $C_1$ to $C_3$ alkoxy, or substituted $C_1$ to $C_3$ alkoxy;

$R^5$ is (v), (vi), or (vii):

(v) the substituted benzene ring of the structure:

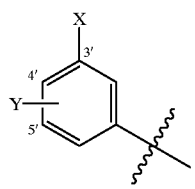

wherein:

X is halogen, CN, $C_1$ to $C_3$ alkoxy, $C_1$ to $C_3$ alkyl, $NO_2$, $C_1$ to $C_3$ perfluoroalkyl, 5 membered heterocyclic ring containing in its backbone 1 to 3 heteroatoms selected from the group consisting of N, O, and S, or $C_1$ to $C_3$ thioalkoxy;

Y is H, halogen, CN, $NO_2$, $C_1$ to $C_3$ alkoxy, $C_1$ to $C_4$ alkyl, or $C_1$ to $C_3$ thioalkoxy;

(vi) the five membered ring having the structure:

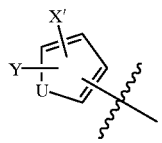

wherein:

U is O, S. or $NR^6$;

X' is selected from the group consisting of halogen, CN, $NO_2$, $C_1$ to $C_3$ alkyl, and $C_1$ to $C_3$ alkoxy;

Y' is selected from the group consisting of H and $C_1$ to $C_4$ alkyl; or (vii) the six membered ring having the structure:

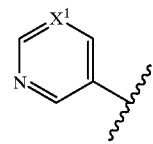

wherein:

$X^1$ is N or $CX^2$;

$X^2$ is halogen, CN, $C_1$ to $C_3$ alkoxy, or $NO_2$;

or pharmaceutically acceptable salt thereof.

5. The method according to claim 4, wherein $R^5$ is selected from the group consisting of:

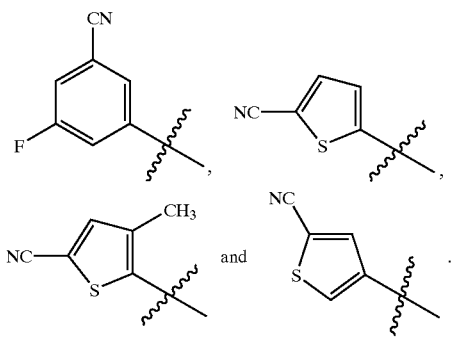

6. The method according to claim 1, wherein:

$R^1$ and $R^2$ are $CH_3$ or $R^1$ and $R^2$ are fused to form the carbon-based 6 membered saturated spirocyclic ring;

$R^3$ is H, OH, $NH_2$, $C_1$ alkyl, substituted $C_1$ alkyl, or $COR^C$;

$R^C$ is H, $C_1$ to $C_3$ alkyl, or $C_1$ to $C_4$ alkoxy;

$R^4$ is H, halogen, $NO_2$, CN, or $C_1$ to $C_3$ alkyl;

$R^5$ is the substituted benzene ring having the formula:

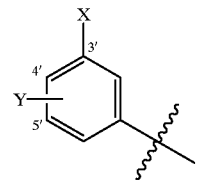

wherein:

X is selected from the group consisting of halogen, CN, methoxy, $NO_2$, and a 5-membered heterocyclic ring, wherein said ring is 2-thiazole;

Y is H or halogen, wherein said halogen is F;

or a pharmaceutically acceptable salt thereof.

7. The method according to claim 1, wherein:

$R^1$ and $R^2$ are $CH_3$ or $R^1$ and $R^2$ are fused to form the carbon-based 6 membered saturated spirocyclic ring;

$R^3$ is H, OH, $NH_2$, $C_1$ alkyl, substituted $C_1$ alkyl, or $COR^C$;

$R^C$ is H, $C_1$ to $C_3$ alkyl, or $C_1$ to $C_4$ alkoxy;

$R^4$ is H, halogen, $NO_2$, CN, or $C_1$ to $C_3$ alkyl;

$R^5$ is the five membered ring having the structure:

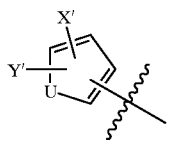

wherein:
U is O, S, or NH;
X' is halogen, CN, or $NO_2$, provided that when U is NH, then X' is not CN;
Y' is H or $C_1$ to $C_4$ alkyl;
or a pharmaceutically acceptable salt thereof.

8. The method according to claim 1, which is selected from the group consisting of:
a) 6-(3-Chlorophenyl)-4,4-dimethyl-1,4-dihydrobenzo[d][1,3]oxazin-2-one;
b) 6-(3-Methoxy-phenyl)-4,4-dimethyl-1,4-dihydro-benzo[d][1,3]-oxazin-2-one;
c) 6-(2-Chloro-phenyl)-4,4-dimethyl-1,4-dihydro-benzo[d][1,3]oxazin-2-one;
d) 6-(4-Chloro-phenyl)-4,4-dimethyl-1,4-dihydro-benzo[d][1,3]-oxazin-2-one;
e) 6-(3-Chloro-phenyl)-4-methyl-1,4-dihydro-benzo[d][1,3]oxazin-2-one;
f) 6-(3-Chloro-phenyl)-4-ethyl-1,4-dihydro-benzo[d][1,3]oxazin-2-one; and
g) 6-(3-Chloro-phenyl)-4-phenyl-1,4-dihydro-benzo[d][1,3]oxazin-2-one;
or a pharmaceutically acceptable salt thereof.

9. The method according to claim 1, which is selected from the group consisting of:
a) 3-(4,4-Dimethyl-2-oxo-1,4-dihydro-2H-benzo[d][1,3]oxazin-6-yl)-benzonitrile;
b) 4,4-Dimethyl-6-(3-nitrophenyl)-1,4-dihydrobenzo[d][1,3]oxazin-2-one;
c) 6-(3-Bromo-5-fluorophenyl)-4,4-dimethyl-1,4-dihydrobenzo[d][1,3]oxazin-2-one;
d) 3-(4,4-Dimethyl-2-oxo-1,4-dihydro-2H-benzo[d][1,3]oxazin-6-yl)-5-fluorobenzonitrile;
e) 5-(4,4-Dimethyl-2-oxo-1,4-dihydro-2H-benzo[d][1,3]oxazin-6-yl)-nicotinonitrile;
f) 4-(4,4-Dimethyl-2-oxo-1,4-dihydro-2H-benzo[d][1,3]oxazin-6-yl)-thiophene-2-carbonitrile;
g) 5-(4,4-Dimethyl-2-oxo-1,4-dihydro-2H-benzo[d][1,3]oxazin-6-yl)-thiophene-2-carbonitrile;
h) 5-(4,4-Dimethyl-2-oxo-1,4-dihydro-2H-benzo[d][1,3]oxazin-6-yl)-4-methyl-thiophene-2-carbonitrile;
i) 4-(4,4-Dimethyl-2-oxo-1,4-dihydro-2H-benzo[d][1,3]oxazin-6-yl)-furan-2-carbonitrile; and j) 4,4-Diethyl-6-(3-nitrophenyl)-1,4-dihydrobenzo[d][1,3]oxazin-2-one;
or a pharmaceutically acceptable salt thereof.

10. The method according to claim 1, which is selected from the group consisting of:
a) 6-(3-Chlorophenyl)-4,4-diethyl-1,4-dihydrobenzo[d][1,3]oxazin-2-one;
b) 6-(3-Chlorophenyl)-spiro[4H-3,1-benzoxazine-4,1'-cyclohexane]-2-(1H)-one;
c) 6-(3-Chlorophenyl)-spiro-[4H-3,1-benzoxazine-4,1'-cyclopentane]-2-(1H)-one;
d) 6-(3-Nitrophenyl)-spiro[4H-3,1-benzoxazine-4,1'-cyclohexan]-2(1H)-one;
e) 4Allyl-6-(3-chlorophenyl)-4-methyl-1,4-dihydro-benzo[d][1,3]oxazin-2-one;
f) 6-(3-Chlorophenyl)-4-methyl-4-propyn-1-yl-1,4-dihydro-benzo[d][1,3]oxazin-2-one; and
g) 6-(3-Chlorophenyl)-4-ethynyl-4-methyl-1,4-dihydro-benzo[d][1,3]oxazin-2-one;
or a pharmaceutically acceptable salt thereof.

11. The method according to claim 1, which is selected from the group consisting of:
a) 6-(3-Chlorophenyl)-4-methyl-4-phenyl-1,4-dihydro-benzo[d][1,3]oxazin-2-one;
b) 4Benzyl-6-(3-chloro-phenyl)-4-methyl-1,4-dihydro-benzo[d][1,3]oxazin-2-one;
c) 6-(3-Chloro-phenyl)-4-cyclopropyl-4-methyl-1,4-dihydro-benzo[d][1,3]oxazin-2-one;
d) 6-(3-Chloro-phenyl)-4-cyclopropyl-4-propyn-1-yl-1,4-dihydro-benzo[d][1,3]oxazin-2-one;
e) 6-(3-Chloro-phenyl)-4,4-dicyclopropyl-1,4-dihydro-benzo[d][1,3]oxazin-2-one.
f) 6-(3-Chloro-phenyl)-4,4-dipropyn-1-yl-1,4-dihydrobenzo[d][1,3]oxazin-2-one;
g) 6-(3-Bromo-5-fluorophenyl)-1,4,4-trimethyl-1,4-dihydrobenzo[d][1,3]oxazin-2-one; and
h) 6-(3-Methoxyphenyl)-4-methyl-4-trifluoromethyl-1,4-dihydro-benzo[d][1,3]oxazin-2-one;
or a pharmaceutically acceptable salt thereof.

12. The method according to claim 1, which is selected from the group consisting of:
a) 6-(3-Acetyl-phenyl)-4,4-dimethyl-1,4-dihydro-benzo[d][1,3]-oxazin-2-one:
b) 6-(3-Benzoyl-phenyl)-4,4-dimethyl-1,4-dihydro-benzo[d][1,3]-oxazin-2-one;
c) 4,4-Dimethyl-6-[3-(1H-tetrazol-5-yl)-phenyl]-1,4-dihydrobenzo[d][1,3]oxazin-2-one;
d) 4-(4,4-Dicyclopropyl-2-oxo-1,4-dihydro-2H-benzo[d][1,3]oxazin-6-yl)-thiophene-2-carbonitrile;
e) 6-(3-Bromo-5- fluoro-phenyl)-4,4-dicyclopropyl-1,4-dihydrobenzo[d][1,3]oxazin-2-one;
f) 3-(4,4-Dicyclopropyl-2-oxo-1,4-dihydro-2H-benzo[d][1,3]oxazin-6-yl)-5-fluoro-benzonitrile;
g) 6-(3-Bromo-5-methyl-phenyl)-4,4-dimethyl-1,4-dihydrobenzo-[d][1,3]oxazin-2-one;
h) 6-(3-Bromo-5-trifluoromethoxy-phenyl)-4,4-dimethyl-1,4-dihydrobenzo[d][1,3]-oxazin-2-one; and
i) 3-(4,4-Dimethyl-2-oxo-1,4-dihydro-2H-benzo[d][1,3]oxazin-6-yl)-5-methyl-benzonitrile;
or a pharmaceutically acceptable salt thereof.

13. The method according to claim 1, which is selected from the group consisting of:
a) 3-(4,4-Dimethyl-2-oxo-1,4-dihydro-2H-benzo[d][1,3]oxazin-6-yl)-5-trifluoromethoxy-benzonitrile;
b) 6-(3,5-difluoro-phenyl)-4,4-dimethyl-1,4-dihydrobenzo[d][1,3]oxazin-2-one;
c) 6-(3,5-dichloro-phenyl)-4,4-dimethyl-1,4-dihydrobenzo-[d][1,3]oxazin-2-one;
d) 6-(3,5-Bis-trifluoromethyl-phenyl)-4,4-dimethyl-1,4-dihydrobenzo[d][1,3]oxazin-2-one;
e) 3-(4,4-Dimethyl-2-oxo-1,4-dihydro-2H-benzo[d][1,3]oxazin-6-yl)-5-methoxy-benzonitrile;
f) 6-(3-Fluoro-phenyl)-4,4-dimethyl-1,4-dihydro-benzo[d][1,3]-oxazin-2-one;
g) 6-(3-Chloro-4-fluoro-phenyl)-4,4-dimethyl-1,4-dihydro-benzo[d][1,3]oxazin-2-one;

h) 3-(1-Diethoxymethyl-4,4-dimethyl-2-oxo-1,4-dihydro-2H-benzo[d][1,3]oxazin-6-yl)-5-fluoro-benzonitrile; and i) 3-Fluoro-5-(1-methoxymethyl-4,4-dimethyl-2-oxo-1,4-dihydro-2H-benzo[d][1,3]oxazin-6-yl)-benzonitrile;

or a pharmaceutically acceptable salt thereof.

14. The method according to claim 1, which is selected from the group consisting of:

a) Phosphoric acid 6-(3-cyano-5-fluoro-phenyl)-4,4-dimethyl-4H-benzo[d][1,3]oxazin-2-yl ester diethyl ether;

b) 3-(4,4-Dimethyl-2-oxo-1,4-dihydro-2H-benzo[d][1,3]oxazin-6-yl)-4-fluoro-benzontrile;

c) 6-(3-Chloro-4-fluoro-phenyl)-8-fluoro-4,4-dimethyl-1,4-dihydrobenzo[d][1,3]-oxazin-2-one;

d) 6-(3-Bromo-phenyl)-4,4-dimethyl-1,4-dihydro-benzo[d][1,3]-oxazin-2-one;

e) 4,4-Dimethyl-6-(3-trimethylsilanylethynyl-phenyl)-1,4-dihydro-benzo[d][1,3]oxazin-2-one;

f) 6-(3-Ethynyl-phenyl)-4,4-dimethyl-1,4-dihydro-benzo[d][1,3]-oxazin-2-one;

g) 3-[3-(4,4-Dimethyl-2-oxo-1,4-dihydro-2H-benzo[d][1,3]oxazin-6-yl)-phenyl]-propynenitrile;

h) 6-(3-Fluoro-5-nitro-phenyl)-4,4-dimethyl-1,4-dihydro-benzo[d][1,3]oxazin-2-one; and i) 6-(3-Chloro-5-fluoro-phenyl)-4,4-dimethyl-1,4-dihydro-benzo[d][1,3]oxazin-2-one;

or a pharmaceutically acceptable salt thereof.

15. The method according to claim 1, which is selected from the group consisting of:

a) 3-Chloro-5-(4,4-dimethyl-2-oxo-1,4-dihydro-2H-benzo[d][1,3]oxazin-6-yl)-benzonitrile;

b) 6-(3,5-Dinitro-phenyl)-4,4-dimethyl-1,4-dihydro-benzo[d][1,3]oxazin-2-one;

c) 5-(4,4-Dimethyl-2-oxo-1,4-dihydro-2H-benzo[d][1,3]oxazin-6-yl)-isophthalonitrile;

d) 4,4-Dimethyl-6-(3-thiazol-2-yl-phenyl)-1,4-dihydro-benzo[d][1,3]oxazin-2-one;

e) 6-(3-Fluoro-5-methoxy-phenyl)-4,4-dimethyl-1,4-dihydro-benzo[d][1,3]oxazin-2-one;

f) 6-(3-Fluoro-5-trifluoromethyl-phenyl)-4,4-dimethyl-1,4-dihydro-benzo[d][1,3]oxazin-2-one;

g) 6-(5-Bromo-pyridin-3-yl)-4,4-dimethyl-1,4-dihydro-benzo[d][1,3]oxazin-2-one;

h) 6-(5-Bromo-1-oxy-pyridin-3-yl)-4,4-dimethyl-1,4-dihydro-benzo[d][1,3]oxazin-2-one;

i) 6-(3-Cyano-5-fluoro-phenyl)-4,4-dimethyl-2-oxo-4H-benzo[d][1,3]oxazine-1-carboxylic acid tert-butyl ester; and j) 5-(4,4-Dimethyl-2-oxo-1,4-dihydro-2H-benzo[d][1,3]oxazin-6-yl)-2-fluoro-benzonitrile;

or a pharmaceutically acceptable salt thereof.

16. The method according to claim 1, which is selected from the group consisting of:

a) 4-(8-Fluoro-4,4-dimethyl-2-oxo-1,4-dihydro-2H-benzo[d][1,3]oxazin-6-yl)-thiophene-2-carbonitrile;

b) 3-Fluoro-5-(8-fluoro-4,4-dimethyl-2-oxo-1,4-dihydro-2H-benzo[d][1,3]oxazin-6-yl)-benzonitrile;

c) 5-(4,4-Dimethyl-2-oxo-1,4-dihydro-2H-benzo[d][1,3]oxazin-6-yl)-thiophene-3-carbonitrile;

d) 2-(4,4-Dimethyl-2-oxo-1,4-dihydro-2H-benzo[d][1,3]oxazin-6-yl)-thiophene-3-carbonitrile;

e) 6-(1,2,4-thiadiazol-3-yl-phenyl)-4,4-dimethyl-1,4-dihydro-benzo[d][1,3]oxazin-2-one;

f) 6-(3-Fluoro-5-thiophen-3-yl-phenyl)-4,4-dimethyl-1,4-dihydro-benzo[d][1,3]oxazin-2-one;

g) 2-(4,4-Dimethyl-2-oxo-1,4-dihydro-2H-benzo[d][1,3]oxazin-6-yl)-pyrrole-1-carboxylic acid tert-butyl ester;

h) 2-(4,4-Dimethyl-2-oxo-1,4-dihydro-2H-benzo[d][1,3]oxazin-6-yl)-5-nitro-pyrrole-1-carboxylic acid tert-butyl ester;

i) 4,4-Dimethyl-6-(5-nitro-1H-pyrrol-2-yl)-1,4-dihydrobenzo[d][1,3]oxazin-2-one; and j) 4,4-Dimethyl-6-(1H-pyrrol-2-yl)-1,4-dihydro-benzo[d][1,3]-oxazin-2-one;

or a pharmaceutically acceptable salt thereof.

17. The method according to claim 1, which is selected from the group consisting of:

a) 4,4-Dimethyl-6-(1-methyl-1H-pyrrol-2-yl)-1,4-dihydro-benzo[d][1,3]oxazin-2-one;

b) 4,4-Dimethyl-6-(1-methyl-5-nitro-1H-pyrrol-2-yl)-1,4-dihydro-benzo[d][1,3]oxazin-2-one;

c) 3-(1,2-Dihydro-2-oxospiro[4H-3,1-benzoxazine-4,1-cyclohexan]-6-yl)-benzonitrile;

d) 3-(1,2-Dihydro-2-oxospiro[4H-3,1-benzoxazine-4,1-cyclohexan]-6-yl)-5-fluorobenzonitrile;

e) 4-(1,2-Dihydro-2-oxospiro[4H-3,1-benzoxazine-4,1-cyclohexan]-6-yl)-2-thiophenecarbonitrile;

f) 5-(1,2-Dihydro-2-oxospiro[4H-3,1-benzoxazine-4,1-cyclohexan]-6-yl)-2-thiophenecarbonitrile;

g) 5-(1,2-Dihydro-2-oxospiro[4H-3,1-benzoxazine-4,1-cyclohexan]-6-yl)-4-methyl-2-thiophenecabonitrile;

h) 5-(4,4-Dimethyl-2-oxo-1,4-dihydro-2H-benzo[d][1,3]oxazin-6-yl)-4-ethyl-thiophene-2-carbonitrile; and i) 5-(4,4-Dimethyl-2-oxo-1,4-dihydro-2H-benzo[d][1,3]oxazin-6-yl)-4-n-propyl-thiophene-2-carbonitrile;

or a pharmaceutically acceptable salt thereof.

18. The method according to claim 1, which is selected from the group consisting of:

a) 5-(4,4-Dimethyl-2-oxo-1,4-dihydro-2H-benzo[d][1,3]oxazin-6-yl)-4-n-butyl-thiophene-2-carbonitrile;

b) 6-(4-Cyano-3-fluorophenyl)-4,4-dimethyl-1,4-dihydrobenzo[d][1,3]-oxazin-2-one;

c) 6-(4-Fluoro-phenyl)-4,4-dimethyl-1,4-dihydro-benzo[d][1,3]-oxazin-2-one;

d) 6-(3,4-Difluoro-phenyl)-4,4-dimethyl-1,4-dihydro-benzo[d][1,3]oxazin-2-one;

e) 6-(2-Fluoro-phenyl)-4,4-dimethyl-1,4-dihydro-benzo[d][1,3]-oxazin-2-one;

f) 3-(4,4-Dimethyl-2-oxo-1,4-dihydro-2H-benzo[d][1,3]-oxazin-6-yl)phenylacetonitrile;

g) 5-(4,4-Dimethyl-2-oxo-1,4-dihydro-2H-benzo[d][1,3]oxazin-6-yl)-furan-2-carbonitrile; and h) 3-(4,4-Dimethyl-2-oxo-1,4-dihydro-2H-benzo[d][1,3]oxazin-6-yl)-2-fluoro-benzonitrile;

or a pharmaceutically acceptable salt thereof.

19. The method according to claim 1, wherein $R^5$ is said five-membered ring b).

20. The method according to claim 19, wherein said five-membered ring b) is a thiophene group.

21. The method according to claim 19, wherein said five-membered ring b) is a furan group.

22. The method according to claim 19, wherein said five-membered ring b) is a pyrrole group.

23. The method according to claim 19, wherein said five-membered ring b) is a thiazole group.

24. The method according to claim 19, wherein said five-membered ring b) is an oxazole group.

25. The method according to claim 19, wherein said five-membered ring b) is an imidazole group.

26. The method according to claim 1, wherein $R^5$ is said six-membered ring b).

27. The method according to claim 26, wherein said six-membered ring b) is a pyridine group.

28. The method according to claim 1, wherein $R^5$ is said substituted benzene ring a).

29. The method according to claim 28, wherein said substituted benzene ring a) is an optionally substituted phenyl group.

30. The method according to claim 29, wherein said substituted phenyl group is a 3-chloro-4-fluoro-phenyl group.

31. The method according to claim 29, wherein said substituted phenyl group is a 3,5-dichloro-phenyl group.

32. The method according to claim 29, wherein said substituted phenyl group is a 3-cyano-4-fluoro-phenyl group.

33. The method according to claim 29, wherein said substituted phenyl group is a 3,4-difluoro-phenyl group.

34. The method according to claim 29, wherein said substituted phenyl group is a 3-cyano-5-chloro-phenyl group.

35. The method according to claim 29, wherein said substituted phenyl group is a 3-trifluoromethyl-5-fluoro-phenyl group.

36. The method according to claim 29, wherein said substituted phenyl group is a 2-fluoro-3-cyano-phenyl group.

37. The method according to claim 29, wherein said substituted phenyl group is a 2-fluoro-phenyl group.

38. The method according to claim 29, wherein said substituted phenyl group is a 4-cyano-3-furanyl-phenyl group.

39. The method according to claim 29, wherein said substituted phenyl group is a 3,4-dichloro-phenyl group.

40. The method according to claim 29, wherein said substituted phenyl group is a 3-fluoro-4-chloro-phenyl group.

41. The method according to claim 29, wherein said substituted phenyl group is a 3-bromo-4-fluoro-phenyl group.

42. The method according to claim 29, wherein said substituted phenyl group is a 3,5-dibromo-phenyl group.

43. The method according to claim 1, wherein $R^1$ and $R^2$ are $C_1$ to $C_6$ alkyl.

44. A method of treating hormone neoplastic disease in a mammal, wherein the hormone-dependent neoplastic disease is selected from the group consisting of uterine myometrial fibroids, endometriosis, benign prostatic hypertrophy, carcinomas and adenocarcinomas of the endometrium, ovary, breast, colon, prostate, pituitary, and meningioma, the method comprising administering to the mammal in need thereof about 0.5 to about 50 mg/kg of said mammal's body weight of a compound of formula I:

wherein:
$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^B COR^A$;
or $R^1$ and $R^2$ are fused to form:
  a) a carbon-based 3 to 8 membered saturated spirocyclic ring;
  b) a carbon-based 3 to 8 membered spirocyclic ring having in its backbone one or more carbon-carbon double bonds; or
  c) a carbon-based 3 to 8 membered heterocyclic ring having in its backbone one to three heteroatoms selected from the group consisting of O, S and N;
the spirocyclic rings of a), b) and c) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl$)_2$;
$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^B$ is H, $C_1$ to $C_3$ alkyl, or substituted $C_1$ to $C_3$ alkyl;
$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;
$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^4$ is H, halogen, CN, $NO_2$, $C_1$ to $C_6$ alkyl, substituted $C_1$ to $C_6$ alkyl, alkynyl, substituted alkynyl, $C_1$ to $C_6$ alkoxy, substituted $C_1$ to $C_6$ alkoxy, amino. $C_1$ to $C_6$ aminoalkyl, or substituted $C_1$ to $C_6$ amnoalkyl;
$R^5$ is selected from the group consisting of (i) and (ii):
  (i) a substituted benzene ring having the substituents X, Y and Z as shown below:

wherein:
X is selected from the group consisting of H, halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, C₁ to C₃ thioalkoxy, substituted C₁ to C₃ thioalkoxy, amino, C₁ to C₃ aminoalkyl, substituted C₁ to C₃ aminoalkyl, NO₂, C₁ to C₃ perfluoroalkyl, 5 or 6 membered heterocyclic ring having in its backbone 1 to 3 heteroatoms selected from the group consisting of N, O, and S, COR$^D$, OCOR$^D$, and NR$^E$COR$^D$:

R$^D$ is H, C₁ to C₃ alkyl, substituted C₁ to C₃ alkyl, aryl, substituted aryl, C₁ to C₃ alkoxy, substituted C₁ to C₃ alkoxy, C₁ to C₃ aminoalkyl, or substituted C₁ to C₃ aminoalkyl;

R$^E$ is H, C₁ to C₃ alkyl, or substituted C₁ to C₃ alkyl;

Y and Z are independent substituents selected from the group consisting of H, halogen, CN, NO₂, amino, aminoalkyl, C₁ to C₃ alkoxy, C₁ to C₃ alkyl, and C₁ to C₃ thioalkoxy;

wherein X, Y, and Z are not all H; and (ii) a five or six membered ring having in its backbone 1, 2, or 3 heteroatoms selected from the group consisting of O, S, SO, SO₂ and NR⁶ and containing one or two independent substituents selected from the group consisting of H, halogen, CN, NO₂, amino, C₁ to C₃ alkyl, C₁ to C₃ alkoxy. C₁ to C₃ aminoalkyl, COR$^F$, and NR$^G$COR$^F$;

RF is H, C₁ to C₃ alkyl, substituted C₁ to C₃ alkyl, aryl, substituted aryl, C₁ to C₃ alkoxy, substituted C₁ to C₃ alkoxy, C₁ to C₃ aminoalkyl, or substituted C₁ to C₃ aminoalkyl;

R$^G$ is H, C₁ to C₃ alkyl, or substituted C₁ to C₃ alkyl;

R⁶ is H or C₁ to C₃ alkyl, with the proviso that when R⁵ is a five-membered ring having in its backbone a NR⁶ heteroatom, and when R⁵ is attached at the two position of said ring, there is no CN substituent in the five position on said ring;

wherein:

said substituted alkyl, alkenyl, and alkynyl groups have one to three substituents selected from the group consisting of halogen, CN, OH, NO₂, amino, aryl, heterocyclic, substituted aryl, substituted heterocyclic, alkoxy, aryloxy, substituted alkyloxy, alkylcarbonyl, alkylcarboxy, alkylamino, and arylthio;

said substituted alkoxy, aminoalkyl, and thioalkoxy groups have one to three substituents selected from the group consisting of alkyl and substituted alkyl, said substituted axyl group has one to four substituents selected from the group consisting of halogen, CN, OH, NO₂, amino, alkyl, cycloalkyl, alkenyl, alkynyl, alkoxy, aryloxy, substituted alkyloxy, alkylcarbonyl, alkylcarboxy, alkylamino, and arylthio;

said substituted cycloalkyl group has one to three substituents selected from the group consisting of halogen, CN, OH, NO₂, amino, aryl, heterocyclic, aryloxy, aryl alkoxy, alkylcarbonyl, alkylcarboxy, alkylamino, and arylthio;

said substituted heterocyclic group has one to four substituents selected from the group consisting of halogen, CN, OH, NO₂, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio;

said substituted alkyloxy group has one to three substituents selected from the group consisting of halogen, CN, OH, NO₂, amino, aryl, heterocyclic, substituted aryl, substituted heterocyclic, alkoxy, aryloxy, alkylcarbonyl, alkylcarboxy, alkylamino, and arylthio;

said aryl group is selected from the group consisting of phenyl, naphthvl, biphenyl, anthryl, tetrahydronaphthyl, and phenanthryl;

said heterocyclic group is a five-membered ring, a six-membered ring, or a multicyclic ring;

said five-membered heterocyclic ring is selected from the group consisting of tetrahydrofuran, pyrrolidinyl, imidazolyl, oxazolyl, isoxazolyl, thienyl, furyl, and thiazolyl;

said six-membered heterocyclic ring is selected from the group consisting of piperidinyl, piperazinyl, 2-oxopiperidinyl, pyridyl, pyrazinyl. pyrimidinyl, pyridazinyl, thiamorpholinyl, azepinyl, and thiamorpholinyl sulfoxide;

said multicyclic heterocyclic ring is selected from the group consisting of indolyl, quinolinyl, benzofuranyl, benzothienyl, and isoquinolinyl, or a pharmaceutically acceptable salt thereof.

45. The method according to claim 44, wherein said compound is selected from the group consisting of 6-(3-Chlorophenyl)-4,4-dimethyl-1,4-dihydrobenzo[d][1,3]oxazin-2-one; 6-(3-Methoxy-phenyl)-4,4-dimethyl-1,4-dihydro-benzo[d][1,3]-oxazin-2-one; 6-(2-Chloro-phenyl)-4,4-dimethyl-1,4-dihydro-benzo[d][1,3]oxazin-2-one; 6-(4-Chloro-phenyl)-4,4-dimethyl-1,4-dihydro-benzo[d][1,3]-oxazin-2-one; 6-(3-Chloro-phenyl)-4-methyl-1,4-dihydro-benzo[d][1,3]oxazin-2-one; 6-(3-Chloro-phenyl)-4-ethyl-1,4-dihydro-benzo[d][1,3]oxazin-2-one; 6-(3-Chloro-phenyl)-4-phenyl-1,4-dihydro-benzo[d][1,3]oxazin-2-one; 3-(4,4-Dimethyl-2-oxo-1,4-dihydro-2H-benzo[d][1,3]oxazin-6-yl)-benzonitrile; 4,4-Dimethyl-6-(3-nitrophenyl)-1,4-dihydrobenzo[d][1,3]oxazin-2-one; 6-(3-Bromo-5-fluorophenyl)-4,4-dimethyl-1,4-dihydrobenzo[d][1,3]oxazin-2-one; 3-(4,4-Dimethyl-2-oxo-1,4-dihydro-2H-benzo[d][1,3]oxazin-6-yl)-5-fluorobenzonitrile; 5-(4,4-Dimethyl-2-oxo-1,4-dihydro-2H-benzo[d][1,3]oxazin-6-yl)-nicotinonitrile; 4-(4,4-Dimethyl-2-oxo-1,4-dihydro-2H-benzo[d][1,3]oxazin-6-yl)-thiophene-2-carbonitrile; 5-(4,4-Dimethyl-2-oxo-1,4-dihydro-2H-benzo[d][1,3]oxazin-6-yl)-thiophene-2-carbonitrile; 5-(4,4-Dimethyl-2-oxo-1,4-dihydro-2H-benzo[d][1,3]oxazin-6-yl)-4-methyl-thiophene-2-carbonitrile; 4-(4,4-Dimethyl-2-oxo-1,4-dihydro-2H-benzo[d][1,3]oxazin-6-yl)-furan-2-carbonitrile; 4,4-Diethyl-6-(3-nitrophenyl)-1,4-dihydrobenzo[d][1,3]oxazin-2-one; 6-(3-Chlorophenyl)-4,4-diethyl-1,4-dihydrobenzo[d][1,3]oxazin-2-one; 6-(3-Chlorophenyl)-spiro[4H-3,1-benzoxazine-4,1'-cyclohexane]-2-(1H)-one; 6-(3-Chlorophenyl)-spiro-[4H-3,1-benzoxazine-4,1'-cyclopentane]-2(1H)-one; 6-(3-Nitrophenyl)-spiro[4H-3,1-benzoxazine-4,1'-cyclohexan]-2(1H)-one; 4Allyl-6-(3-chlorophenyl)-4-methyl-1,4-dihydro-benzo[d][1,3]oxazin-2-one; 6-(3-Chlorophenyl)-4-methyl-4-propyn-1-yl-1,4-dihydro-benzo[d][1,3]oxazin-2-one; 6-(3-Chlorophenyl)-4-ethynyl-4-methyl-1,4-dihydro-benzo[d][1,3]oxazin-2-one; 6-(3-Chlorophenyl)-4-methyl-4-phenyl-1,4-dihydro-benzo[d][1,3]oxazin-2-one; 4Benzyl-6-(3-chloro-phenyl)-4-methyl-1,4-dihydro-benzo[d][1,3]oxazin-2-one; 6-(3-Chloro-phenyl)-4-cyclopropyl-4-methyl-1,4-dihydro-benzo[d][1,3]oxazin-2-one; 6-(3-Chloro-phenyl)-4-cyclopropyl-4-propyn-1-yl-1,4-dihydro-benzo[d][1,3]oxazin-2-one; 6-(3-Chloro-phenyl)-4,4-dicyclopropyl-1,4-dihydro-benzo[d][1,3]oxazin-2-one; 6-(3-Chloro-phenyl)-4,4-dipropyn-1-yl-1,4-dihydrobenzo[d][1,3oxazin-2-one; 6-(3-Bromo-5-fluorophenyl)-1,4,4-trimethyl-1,4-dihydrobenzo[d][1,3]oxazin-2-one; 6-(3-Methoxyphenyl)-4-methyl-4-trifluoromethyl-1,4-dihydro-benzo[d][1,3]oxazin-2-one; 6-(3-Acetyl-phenyl)-4,4-dimethyl-1,4-dihydro-benzo[d][1, 3]-oxazin-2-one; 6-(3-Benzoyl-phenyl)-4,4-dimethyl-1,4-dihydro-benzo[d][1,3]-oxazin-2-one; 4-Dimethyl-6-[3-(1H-tetrazol-5-yl)-phenyl]-1,4-dihydrobenzo[d][1,3]oxazin-2-one; 4-(4,4-Dicyclopropyl-2-oxo-1,4-dihydro-2H-benzo[d][1,3]oxazin-6-yl)-thiophene-2-carbonitrile; 6-(3-Bromo-5-fluoro-phenyl)-4,4-dicyclopropyl-1,4-dihydrobenzo[d][1,3]oxazin-2-one; 3-(4,4-Dicyclopropyl-2-oxo-1,4-dihydro-2H-benzo[d][1,3]oxazin-6-yl)-5-fluoro-benzonitrile; 6-(3-Bromo-5-methyl-phenyl)-4,4-dimethyl-1,4-dihydrobenzo-[d][1,3]oxazin-2-one; 6-(3-Bromo-5-trifluoromethoxy-phenyl)-4,4-dimethyl-1,4-dihydrobenzo[d][1,3]-oxazin-2-one; 3-(4,4-Dimethyl-2-oxo-1,4-dihydro-2H-benzo[d][1,3]oxazin-6-yl)-5-methyl-benzonitrile; 3-(4,4-Dimethyl-2-oxo-1,4-dihydro-2H-benzo[d][1,3]oxazin-6-yl)-5-trifluoromethoxy-benzonitrile; 6-(3,5-difluoro-phenyl)-4,4-dimethyl-1,4-dihydrobenzo-[d][1,3]oxazin-2-one; 6-(3,5-dichloro-phenyl)-4,4-dimethyl-1,4-dihydrobenzo-[d][1,3]oxazin-2-one; 6-(3,5-Bis-trifluoromethyl-phenyl)-4,4-dimethyl-1,4-dihydrobenzo[d][1,3]oxazin-2-one; 3-(4,4-Dimethyl-2-oxo-1,4-dihydro-2H-benzo[d][1,3]oxazin-6-yl)-5-methoxy benzonitrile; 6-(3-Fluoro-phenyl)-4,4-dimethyl-1,4-dihydro-benzo[d][1,3]-oxazin-2-one; 6-(3-Chloro-4-fluoro-phenyl)-4,4-dimethyl-1,4-dihydro-benzo[d][1,3]oxazin-2-one; 3-(1-Diethoxymethyl-4,4-dimethyl-2-oxo-1,4-dihydro-2H-benzo[d][1,3]oxazin-6-yl)-5-fluoro-benzonitrile; 3-Fluoro-5-(1-methoxymethyl-4,4-dimethyl-2-oxo-1,4-dihydro-2H-benzo[d][1,3oxazin-6-yl)-benzonitrile; Phosphoric acid 6-(3-cyano-5-fluoro-phenyl)-4,4-dimethyl-4H-benzo[d][1,3]oxazin-2-yl ester diethyl ether; 3-(4,4-Dimethyl-2-oxo-1,4-dihydro-2H-benzo[d][1,3]oxazin-6-yl)-4-fluoro-benzonitrile; 6-(3-Chloro-4-fluoro-phenyl)-8-fluoro-4,4-dimethyl-1,4-dihydrobenzo[d][1,3]-oxazin-2-one; 6-(3-Bromo-phenyl)-4,4-dimethyl-1,4-dihydro-benzo[d][1,3]-oxazin-2-one; 4,4-Dimethyl-6-(3-trimethylsilanylethynyl-phenyl)-1,4-dihydro-benzo[d][1,3]oxazin-2-one; 6-(3-Ethynyl-phenyl)-4,4-dimethyl-1,4-dihydro-benzo[d][1,3]-oxazin-2-one; 3-[3-(4,4-Dimethyl-2-oxo-1,4-dihydro-2H-benzo[d][1,3]oxazin-6-yl)-phenyl]-propynenitrile; 6-(3-Fluoro-5-nitro-phenyl)-4,4-dimethyl-1,4-dihydro-benzo[d][1,3]oxazin-2-one; 6-(3-Chloro-5-fluoro-phenyl)-4,4-dimethyl-1,4-dihydro-benzo[d][1,3]oxazin-2-one; 3-Chloro-5-(4,4-dimethyl-2-oxo-1,4-dihydro-2H-benzo[d][1,3]oxazin-6-yl)-benzonitrile; 6-(3,5-Dinitro-phenyl)-4,4-dimethyl-1,4-dihydro-benzo[d][1,3]oxazin-2-one; 5-(4,4-Dimethyl-2-oxo-1,4-dihydro-2H-benzo[d][1,3]oxazin-6-yl)-isophthalonitrile; 4,4-Dimethyl-6-(3-thiazol-2-yl-phenyl)-1,4-dihydro-benzo[d][1,3]oxazin-2-one; 6-(3-Fluoro-5-methoxy-phenyl)-4,4-dimethyl-1,4-dihydro-benzo[d][1,3]oxazin-2-one; 6-(3-Fluoro-5-trifluoromethyl-phenyl)-4,4-dimethyl-1,4-dihydro-benzo[d][1,3]oxazin-2-one; 6-(5-Bromo-pyridin-3-yl)-4,4-dimethyl-1,4-dihydro-benzo[d][1,3]oxazin-2-one; 6-(5-Bromo-1-oxy-pyridin-3-yl)-4,4-dimethyl-1,4-dihydro-benzo[d][1,3]oxazin-2-one; 5-(4,4-Dimethyl-2-oxo-1,4-dihydro-2H-benzo[d][1,3]oxazin-6-yl)-2-fluoro-benzonitrile; 4-(8-Fluoro-4,4-dimethyl-2-oxo-1,4-dihydro-2H-benzo[d][1,3]oxazin-6-yl)-thiophene-2-carbonitrile; 3-Fluoro-5-(8-fluoro-4,4-dimethyl-2-oxo-1,4-dihydro-2H-benzo[d][1,3]oxazin-6-yl)-benzonitrile; 5-(4,4-Dimethyl-2-oxo-1,4-dihydro-2H-benzo[d][1,3]oxazin-6-yl)-thiophene-3-carbonitrile; 2-(4,4-Dimethyl-2-oxo-1,4-dihydro-2H-benzo[d][1,3]oxazin-6-yl)-thiophene-3-carbonitrile; 6-(1,2,4-thiadiazol-3-yl-phenyl)-4,4-dimethyl-1,4-dihydro-benzo[d][1,3]oxazin-2-one; 6-(3-Fluoro-5-thiophen-3-yl-phenyl)-4,4-dimethyl-1,4-dihydro-benzo[d][1,3]oxazin-2-one; 4,4-Dimethyl-6-(5-nitro-1H-pyrrol-2-yl)-1,4-dihydrobenzo[d][1,3]oxazin-2-one; 4,4-Dimethyl-6-(1H-pyrrol-2-yl)-1,4-dihydro-benzo[d][1,3]-oxazin-2-one; 4,4-Dimethyl-6-(1-methyl-1H-pyrrol-2-yl)-1,4-dihydro-benzo[d][1,3]oxazin-2-one; 4,4-Dimethyl-6-(1-methyl-5-nitro-1H-pyrrol-2-yl)-1,4-dihydro-benzo[d][1,3]oxazin-2-one; 3-(1,2-Dihydro-2-oxospiro[4H-3,1-benzoxazine-4,1-cyclohexan]-6-yl)-benzonitrile; 3-(1,2-Dihydro-2-oxospiro[4H-3,1-benzoxazine-4,1-cyclohexan]-6-yl)-5-fluorobenzonitrile; 4-(1,2-Dihydro-2-oxospiro[4H-3,1-benzoxazine-4,1-cyclohexan]-6-yl)-2-thiophenecarbonitrile; 5-(1,2-Dihydro-2-oxospiro[4H-3,1-benzoxazine-4,1-cyclohexan]-6-yl)-2-thiophenecarbonitrile; 5-(1,2-Dihydro-2-oxospiro[4H-3,1-benzoxazine-4,1-cyclohexan]-6-yl)-4-methyl-2-thiophenecabonitrile; 5-(4,4-Dimethyl-2-oxo-1,4-dihydro-2H-benzo[d][1,3]oxazin-6-yl)-4-ethyl-thiophene-2-carbonitrile; 5-(4,4-Dimethyl-2-oxo-1,4-dihydro-2H-benzo[d][1,3]oxazin-6-yl)-4-n-propyl-thiophene-2-carbonitrile; 6-(4-Cyano-3-fluorophenyl)-4,4-dimethyl-1,4-dihydrobenzo[d][1,3-oxazin-2-one; 6-(4-Fluoro-phenyl)-4,4-dimethyl-1,4-dihydro-benzo[d][1,3-oxazin-2-one; 6-(3,4-Difluoro-phenyl)-4,4-dimethyl-1,4-dihydro-benzo[d][1,3]oxazin-2-one; 6-(2-Fluoro-phenyl)-4,4-dimethyl-1,4-dihydro-benzo[d][1,3]-oxazin-2-one; 3-(4,4-Dimethyl-2-oxo-1,4-dihydro-2H-benzo[d][1,3]-oxazin-6-yl)phenylacetonitrile; 5-(4,4-Dimethyl-2-oxo-1,4-dihydro-2H-benzo[d][1,3]oxazin-6-yl)-furan-2-carbonitrile; and 3-(4,4-Dimethyl-2-oxo-1,4-dihydro-2H-benzo[d][1,3]oxazin-6-yl)-2-fluoro-benzonitrile;

or a pharmaceutically acceptable salt thereof.

46. A method of treating hormone neoplastic disease in a mammal, wherein the hormone-dependent neoplastic disease is selected from the group consisting of uterine myometrial fibroids, endometriosis, benign prostatic hypertrophy, carcinomas and adenocarcinomas of the endometrium, ovary, breast, colon, prostate, pituitary, and meningioma, the method comprising administering to the mammal in need thereof about 0.5 to about 50 mg/kg of said mammal's body weight of a compound of formula I:

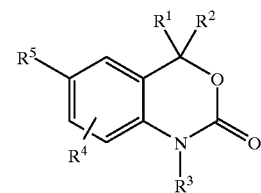

I wherein:
$R^1$ and $R^2$ are independent substituents selected from the group consisting of H and $C_1$ to $C_6$ alkyl;
$R^3$ is H;
$R^4$ is H;
$R^5$ is selected from the group consisting of (i) and (ii):
(i) a substituted benzene ring having the substituents X, Y and Z as shown below:

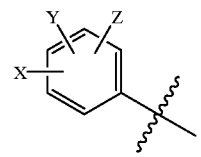

wherein:
X is selected from the group consisting of halogen, CN, $C_1$ to $C_3$ alkyl, and substituted $C_1$ to $C_3$ alkyl;

Y and Z are independent substituents selected from the group consisting of H, halogen, CN, $NO_2$, and $C_1$ to $C_3$ alkyl;

(ii) a five or six membered ring having in its backbone 1, 2, or 3 heteroatoms selected from the group consisting of O, S, SO, $SO_2$ and $NR^6$ and containing one or two independent substituents selected from the group consisting of H, halogen, and CN;

with the proviso that wherein when $R^5$ is a five-membered ring having in its backbone a $NR^6$ heteroatom, and when $R^5$ is attached at the two position of said ring, there is no CN substituent in the five position on said ring;

wherein:

said five-membered heterocyclic ring is selected from the group consisting of tetrahydrofuran, pyrrolidinyl, imidazolyl, oxazolyl, isoxazolyl, thienyl, furyl, and thiazolyl; and said six-membered heterocyclic ring is selected from the group consisting of piperidinyl, piperazinyl, 2-oxopiperidinyl, pyridyl, pyrazinyl, pyrimidinyl, pyridazinyl, thiamorpholinyl, azepinyl, and thiamorpholinyl sulfoxide;

or a pharmaceutically acceptable salt thereof.

* * * * *

UNITED STATES PATENT AND TRADEMARK OFFICE
CERTIFICATE OF CORRECTION

PATENT NO. : 6,566,358 B2
DATED : May 20, 2003
INVENTOR(S) : Zhang et al.

It is certified that error appears in the above-identified patent and that said Letters Patent is hereby corrected as shown below:

Title page,
Item [57], ABSTRACT,
Line 9, replace "alky" with -- alkyl --.

Column 7,
Line 30, replace "$C_1$" with -- $C_8$ --.
Line 60, replace "alky" with -- alkyl --.

Column 20,
Line 35, replace "161" with -- 1.61 --.
Line 45, replace "158" with -- 1.58 --.

Column 23,
Line 14, replace "/1;1" with -- /1:1 --.
Line 32, replace "$([M-H]^{31}$" with -- $([M-H]^-$ --.

Column 24,
Line 33, replace "J'8.2" with -- J=8.2 --.
Line 42, replace "(11.9 g" with -- (111.9g --.

Column 26,
Lines 41 and 65, replace "cyclohexane-2" with -- cyclohexane]-2 --.

Column 27,
Line 11, replace "cyclopentane-2" with -- cyclopentane]2 --.

Column 29,
Line 18, replace "=8.2," with -- J=8.2, --.
Line 52, replace "[11,3]" with -- [1,3] --.

UNITED STATES PATENT AND TRADEMARK OFFICE
CERTIFICATE OF CORRECTION

PATENT NO.   : 6,566,358 B2
DATED        : May 20, 2003
INVENTOR(S)  : Zhang et al.

It is certified that error appears in the above-identified patent and that said Letters Patent is hereby corrected as shown below:

<u>Column 32,</u>
Line 50, replace "([M-H]$^{31}$" with -- ([M-H]$^-$ --.

<u>Column 41,</u>
Line 61, replace "acetate/I:1)" with -- acetate/1:1) --.

<u>Column 44,</u>
Line 60, replace "4,4-dimehtyl" with -- 4,4-dimethyl --.

<u>Column 48,</u>
Line 17, replace "H,N, 8.22" with -- H,5.81, N, 8.22 --.

<u>Column 49,</u>
Line 42, replace "(4.1-" with -- (4,1'- --.

<u>Column 52,</u>
Table 1, under column CV-1 IC$_{50}$ (mg/kg), replace "6.96 ±10.84" with -- 6.96±0.84 --.

<u>Column 62,</u>
Line 65, replace "[M+H]$_{30}$" with -- [M+H]$^+$ --.

<u>Column 64,</u>
Line 25, replace "d$_6$) δ4.50" with -- d$_6$) □4.50 --.
Line 60, replace "(M-H)_" with -- (M-H)$^-$ --.

<u>Column 66,</u>
Line 10, replace "m/z -300." with -- m/z =300 --.
Line 36, replace "7,59" with -- 7.59 --.
Line 49, replace "$_1$H-NMR" with -- $^1$H-NMR --.

UNITED STATES PATENT AND TRADEMARK OFFICE
CERTIFICATE OF CORRECTION

PATENT NO. : 6,566,358 B2
DATED : May 20, 2003
INVENTOR(S) : Zhang et al.

It is certified that error appears in the above-identified patent and that said Letters Patent is hereby corrected as shown below:

Column 67,
Line 8, replace "5-diethoxymeyhyl" with -- 5-diethoxymethyl --.

Column 79,
Line 24, replace "RF" with -- $R^F$ --.
Line 45, replace "axyl" with -- aryl --.

Column 80,
Line 2, replace "naphthvl" with -- naphthyl --.

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,566,358 B2
DATED : May 20, 2003
INVENTOR(S) : Zhang et al.

It is certified that error appears in the above-identified patent and that said Letters Patent is hereby corrected as shown below:

<u>Title page,</u>
Item [62], Related U.S. Application Data, replace "now abandoned" with -- US Patent No. 6,509,334 --.

Signed and Sealed this

Twenty-seventh Day of July, 2004

JON W. DUDAS
*Acting Director of the United States Patent and Trademark Office*